(12) United States Patent
Thullier et al.

(10) Patent No.: US 8,535,668 B2
(45) Date of Patent: Sep. 17, 2013

(54) CHIMERIC ANTI-RICIN ANTIBODY

(75) Inventors: Philippe Thullier, Bernin (FR); Alexandre Fontayne, La Madeleine (FR)

(73) Assignees: Etat Francais Represente par le Delegue General pour l'Armement, Bagneux (FR); LFB Biotechnologies, Courtaboeuf (FR)

( * ) Notice: Subject to any disclaimer, the term of this patent is extended or adjusted under 35 U.S.C. 154(b) by 0 days.

(21) Appl. No.: 13/508,108

(22) PCT Filed: Nov. 4, 2010

(86) PCT No.: PCT/FR2010/052375
§ 371 (c)(1),
(2), (4) Date: Jun. 27, 2012

(87) PCT Pub. No.: WO2011/055088
PCT Pub. Date: May 12, 2011

(65) Prior Publication Data
US 2012/0258100 A1    Oct. 11, 2012

(30) Foreign Application Priority Data

Nov. 4, 2009    (FR) .................................... 09 57786

(51) Int. Cl.
*A61K 39/395* (2006.01)
*C07K 16/16* (2006.01)
*C07K 16/40* (2006.01)

(52) U.S. Cl.
USPC .................. 424/133.1; 424/146.1; 530/387.3; 530/388.26; 530/388.5

(58) Field of Classification Search
None
See application file for complete search history.

(56) References Cited

U.S. PATENT DOCUMENTS

| 5,626,844 A | 5/1997 | Lemley et al. |
| 2002/0150580 A1* | 10/2002 | Newman et al. ........... 424/154.1 |
| 2011/0182878 A1 | 7/2011 | Thullier et al. |

FOREIGN PATENT DOCUMENTS

WO    2009/053637 A2    4/2009

OTHER PUBLICATIONS

GenBank Accession No. AC12547, submitted Oct. 6, 2008.*
GenBank Accession No. AC12548, submitted Oct. 6, 2008.*
International Search Report, dated Feb. 18, 2011, from corresponding PCT application.
Yugang Wang et al., "Novel chimeric anti-ricin antibody C4C13 with neutralizing activity against ricin toxicity", Biotechnology Letters, Jul. 27, 2007, pp. 1811-1816, vol. 29, No. 12.
Carolyn R. McGuinness et al., "Characterization of a novel high-affinity monoclonal immunoglobulin G antibody against the ricin B subunit", Infection and Immunity, Jun. 1, 2006, pp. 3463-3470, vol. 74, No. 6.
Thibaut Pelat et al., "Isolation of a human-like antibody fragment (scFv) that neutralizes ricin biological activity", BMC Biotechnology, Jun. 30, 2009, pp. 1-13, vol. 9, No. 60.
Paul V. Lemley et al., "Identification and Characterization of a Monoclonal Antibody that Neutralizes Ricin Toxicity in Vitro and in Vivo", Hybridoma, Oct. 1, 1994, pp. 417-421, vol. 13, No. 5.
Emmanuelle Laffly et al., "Selection of a macaque Fab with framework regions like those in humans, high affrinity, and ability to neutralize the protective antigen (PA) of *Bacillus anthracis* by binding to the segment of PA between residues 686 and 694", Antimicrobial Agents and Chemotherapy, Aug. 1, 2005, pp. 3414-3420, vol. 49, No. 8.

* cited by examiner

*Primary Examiner* — Sheela J Huff
*Assistant Examiner* — Jessica H Roark
(74) *Attorney, Agent, or Firm* — Young & Thompson

(57) ABSTRACT

A chimeric monoclonal antibody targeted at ricin, in which the light chain and heavy chain are such that:
  the constant region of the light chain and the constant region of the heavy chain are essentially made up respectively of the constant region of the light chain and the constant region of the heavy chain of human immunoglobulin,
  the variable region of the light chain and the variable region of the heavy chain include respectively the variable region of the light chain and the variable region of the heavy chain of macaque immunoglobulin,
the monoclonal antibody not substantially inducing an immune response against chimeric antibodies.

12 Claims, 12 Drawing Sheets

CHIMERIC ANTI-RICIN ANTIBODY

FIELD OF THE INVENTION

This invention concerns a chimeric antibody directed against Ricin.

BACKGROUND OF THE INVENTION

Ricin is a toxalbumin produced by a shrub belonging to the Euphorbiaceae family, the Castor Oil Plant (*Ricinus communis*). Ricin is a highly toxic glycoprotein with a molecular weight of 66 kDa formed by two polypeptide chains A and B connected together by a disulphide bridge. Chain B allows the toxin to attach itself to the cell wall while Chain B, which is responsible for its toxic properties, is capable of inhibiting protein synthesis by inhibiting 28S ribosomal RNA, causing cell death. It is present in the castor oil seed in concentrations of between 1% and 10%.

It may be extracted from incompletely purified castor oil.

As a toxin, ricin is extremely toxic. However, its toxicity varies according to the means by which it penetrates the organism.

When ricin is absorbed through digestion, it is largely destroyed by proteolytic digestive enzymes but its perlingual absorption may increase the quantity absorbed.

In contrast, when ricin is inhaled (pulmonary route) or administered via the parenteral route its toxicity is multiplied 1000-fold.

Symptoms are fairly non-specific and vary according to the route by which the ricin is absorbed. They generally become evident within a period of 2 to 24 hours and rarely take longer than 2 days to appear. Absorption through ingestion causes vomiting, feelings of faintness, abdominal pain, bloody diarrhoea (stools resembling rice water), a painful need to defecate or urinate (anuria), dehydration, drowsiness, muscle weakness, cramps, vasomotor paralysis and tachycardia. Absorption via inhalation causes weakness, fever, dizziness, dyspnoea, coughing, pulmonary oedemas and pain in the limbs.

After an apparent improvement, infection may have a fatal outcome.

In humans, the dose of ricin estimated to be lethal is between 1 and 10 μg/kg.

In view of these varied symptoms and the danger caused by ricin at a very low dose, there is a real need for protection against ricin contamination, including in response to its potential use in the context of bioterrorist attacks.

A rapid diagnostic test for ricin poisoning via the pulmonary route has recently been developed (Guglielmo-Viret et al. 2007). After ricin exposure, the following antidotes may be used: sugar analogues to prevent the ricin from connecting to its target, or catalytic subunit inhibitors such as Azidothymidine.

Vaccination might constitute another ricin poisoning treatment strategy. For example, antibodies have been developed that are designed to interfer with the connection that the anthrax toxin makes with cell surface receptors or to inhibit the assembly of the toxin.

However, no ricin-specific therapy is currently available.

Wang et al. (Wang et al., 2007, Biotechnol Lett 29: 1811-1816) recently developed a human-mouse chimeric antibody against ricin. However, although this first-generation chimeric antibody is ricin-specific, it is capable of generating a Human Anti-Chimeric Antibody (HACA) immune response and of inducing low patient tolerance.

The international application WO 2009/053637 describes single-chain Fv (scFv) fragments from constant regions of macaque antibodies that are capable of effectively neutralising ricin, as well as humanized or super-humanized scFv fragments.

However, such fragments are small in size, have a very short half-life, are rapidly eliminated by the kidneys and are incapable of providing long-term protection. Furthermore, given the lack of a constant region, these fragments are relatively ineffective at stimulating the immune system (recruitment of immune effectors).

Thus, there is a real need to provide ricin-specific antibodies that are stable after administration and that possess a very high toxin neutralization rate.

It is also important to provide antibodies that do not contribute to a HACA-type immune response in the host when they are administered.

SUMMARY OF THE INVENTION

Thus, the object of the invention is to provide ricin-neutralising antibodies.

The invention is also intended to provide the means of producing these ricin-specific antibodies.

Another object of the invention concerns the use of these antibodies as medication or as decontamination agents in response to ricin contamination.

The invention concerns a chimeric monoclonal antibody against ricin, in which the light chain and the heavy chain are such that:
- the constant region of the light chain essentially comprises the constant region of the light chain of a human immunoglobulin;
- the constant region of the heavy chain essentially comprises the constant region of the heavy chain of a human immunoglobulin;
- the variable region of the light chain includes the variable region of the light chain of a macaque immunoglobulin; and
- the variable region of the heavy chain includes the variable region of the heavy chain of a macaque immunoglobulin;

the said monoclonal antibody not substantially inducing a Human Anti-Chimeric Antibody immune response.

The invention relies on the discovery made by the Inventors that chimeric macaque/human antibodies under the invention display improved ricin neutralisation, compared to the antibodies or antibody fragments used previously, and that the said antibodies are similar to human antibodies and therefore should not cause a Human Anti-Chimeric Antibody immune response.

DETAILED DESCRIPTION OF THE INVENTION

Under the invention, the term "antibody" refers to an immunoglobulin, an oligomeric protein comprising 4 chains that contribute to acquired immune response.

Immunoglobulins are familiar to professionals and they consist of a combination of two dimers each comprising a heavy chain and a light chain. The oligomeric complex is assembled through the connection of a light chain and a heavy chain via a disulphide bridge between two cysteines, the two heavy chains in turn being connected to one another by two disulphide bridges.

Each heavy chain and each light chain comprises a constant region and a variable region. The assembly of the constituent chains of an antibody allow for the definition of a characteristically Y-shaped three-dimensional structure, where:

the base of the Y corresponds to the constant region Fc, which is recognised by the Fc receptors and complement; and the ends of the arms of the Y correspond to the corresponding assembly of the variable regions of the light chain and of the heavy chain.

More specifically, each light chain comprises a variable region ($V_L$) and a constant region ($C_L$). Each heavy chain comprises a variable region ($V_H$) and a constant region composed of three constant domains $C_{H1}$, $C_{H2}$ and $C_{H3}$. The domains $C_{H2}$ and $C_{H3}$ make up the area Fc.

The structure of an antibody is depicted diagrammatically in FIG. 1.

The variable region of the light chain comprises three antigen recognition determining domains (CDRs) surrounded by four structural domains. The three-dimensional folding of the variable region is such that the 3 CDRs are exposed on the same side of the protein and allow for the formation of a special structure to recognise a specific antigen.

The pearl-necklace structure of a variable region of a light or heavy chain of an antibody is depicted in FIG. 2.

The antibodies described in the invention are isolated and purified and they are different from natural antibodies as they are chimeric. These antibodies are mature, meaning that they possess a three-dimensional ad hoc structure allowing them to recognise the antigen and they possess all the post-translational modifications essential to their antigen recognition.

They are monoclonal antibodies, meaning that they only recognise a single antigenic determinant in ricin, unlike polyclonal antibodies, which correspond to a mixture of monoclonal antibodies and can therefore recognise multiple antigenic determinants within a single protein.

For the purposes of the invention, "chimeric monoclonal antibody" is defined as an isolated antibody in which the sequence of each constituent light chain and/or heavy chain includes or consists of a hybrid sequence derived from at least two different animals. More specifically, the chimeric antibodies in the invention are human/macaque hybrids, meaning that a region of the sequence of the light chains and heavy chains derives from the sequence of a macaque immunoglobulin while the rest of the sequence of those heavy chains and light chains derives from the sequence of one, or potentially several human immunoglobulins.

"The constant region of the light chain essentially comprises the constant region of the light chain of a human immunoglobulin" means that the constant region of the light chain may comprise the sequence of the constant region of a human immunoglobulin light chain, but may also comprise a sequence corresponding to the fusion of several sequences from several constant regions of several human immunoglobulins. In other words, the constant region of the light chain may comprise a sequence corresponding to a mosaic of sequences from constant regions of light chains, provided that this mosaic sequence reconstitutes a sequence of a constant region of a light chain.

"The constant region of the heavy chain essentially comprises the constant region of the heavy chain of a human immunoglobulin" means that the constant region of the heavy chain may comprise the sequence of the constant region of a human immunoglobulin heavy chain, but may also comprise a sequence corresponding to the fusion of several sequences from several constant regions of several human immunoglobulins. In other words, the constant region of the heavy chain may comprise a sequence corresponding to a mosaic of sequences from constant regions of heavy chains, provided that this mosaic sequence reconstitutes a sequence of a constant region of a heavy chain.

"The variable region of the light chain includes the variable region of the light chain of a macaque immunoglobulin" means that the sequence of the variable region of the light chain corresponds to the sequence of the variable region of a macaque immunoglobulin light chain. This variable region of the light chain may be merged into its N-terminal region, in the C-terminal region of a sequence allowing for the excretion of the antibody. This sequence allowing for the excretion of the antibody is called the signal peptide or leader sequence.

"The variable region of the heavy chain includes the variable region of the heavy chain of a macaque immunoglobulin" means that the sequence of the variable region of the heavy chain corresponds to the sequence of the variable region of a macaque immunoglobulin heavy chain. This variable region of the heavy chain may be merged into its N-terminal region, in the C-terminal region of a sequence allowing for the excretion of the antibody.

Thus, the definition of the monoclonal antibody under the invention covers both:

The precursor of the chimeric human/macaque antibody as defined above; and

The chimeric human/macaque antibody as defined above.

Within the cell that produces the monoclonal antibody covered by the invention, the said monoclonal antibody against ricin is produced in the form of a precursor. Thus, in the N-terminal region of the light chain and heavy chain, this precursor possesses a leader sequence or signal peptide. This precursor therefore undergoes various stages of maturation, and in particular its leader sequences are cleaved so as to allow the antibody to be secreted in the extra-cellular environment. The secreted antibody is therefore a mature antibody.

The monoclonal antibodies under the invention "do not substantially induce a Human Anti-Chimeric Antibody immune response". This means that when the monoclonal antibodies under the invention are administered to an individual, including a human being, the immune system of the said individual is not substantially stimulated or undergoes little stimulation, and so the said individual does not produce any antibodies against the antibodies covered by the invention.

One beneficial method of producing the invention concerns a monoclonal antibody as defined above that is capable of neutralising ricin in vitro and in vivo, specifically yielding a ricin neutralisation rate higher than the neutralisation rate of an scFv fragment against ricin.

The Inventors have demonstrated that the antibody according to the invention is capable of inhibiting ricin more effectively and at a lower dose than a single-chain fragment of an immunoglobulin (scFv), including a chimeric human/macaque scFv fragment as defined under the invention One beneficial method of producing the invention concerns a monoclonal antibody as defined above that is capable of neutralising ricin, specifically yielding a ricin neutralisation rate of at least 40%, 50%, 60%, 70% and preferably at least 80%.

The monoclonal antibodies under the invention are "capable of neutralising ricin". This means that the monoclonal antibodies according to the invention are capable of preventing the action of ricin, or in other words of inhibiting the toxicity of ricin on subunit 28S of ribosomes. This inhibition is due to ricin sequestration or to masking of the ricin domain or domains responsible for its toxicity.

Consequently, the monoclonal antibodies under the invention neutralise ricin toxicity.

The antibody neutralisation activity may be measured with the assistance of the routine protocol in regular use among professionals. Among these tests, we can cite the neutralisation test based on cell survival.

This test measures the capacity of the antibodies under the invention to protect J774A.1 cells put in contact with ricin against death.

In short, J774A.1 cells (ATCC-LGC, Molsheim, France) are cultured at a density of 14,000 cells/well (200 μl/well) in a culture dish and cultivated at 37° C. with 5% $CO_2$ for 24 hours in some DMEM to which 10% foetal calf serum is added. The antibodies under the invention are incubated with 480 ng/ml of ricin or with control serum (irrelevant antibodies) for 1 hour. The mixture is then added to the cells. 24 hours later, cell viability is measured via techniques known to professionals (Trypan blue exclusion, Cytotox (Promega), apoptosis measurement etc). Each test is corrected in relation to cell controls that are "100% viable" (no ricin and no antibodies) and "0% viable" (ricin without antibodies).

Another test can be used to measure the neutralising activity of the monoclonal antibodies of the invention, which involves measuring the inhibition of protein translation. For this, one measures the translation of a marker protein (e.g. luciferase translation) under an acellular in vitro translation system [Hale M L *Pharmacol Toxicol* 2001, 88(5):255-260].

In short, the luciferase messenger RNA translation assay is as follows:

The monoclonal antibodies are deposited in some Phosphate Buffered Saline (PBS) in 96-well dishes and ricin is added at a final concentration of 4 mM. Rabbit reticulocyte lysate complemented with RNAsin®, amino acids and luciferase messenger RNA is then added into each well. The reaction lasts for 1 hr 30 mins.

5 μL of the reaction is then sampled and added to 45 μL of reaction buffer allowing luciferase activity to be detected (Luciferase assay reagent, Promega, Inc.). Light emission (luminescence) is measured in counts per second (CPS) using a Victor multi-plate reader (PerkinElmer Wallac, Boston Mass.). The data is expressed as a percentage in relation to the control (% control=(CPS processed/control CPS)×100)).

Another beneficial method of producing the invention concerns a monoclonal antibody defined above, wherein:

The constant region of the light chain includes or consists of the constant region of the light chain of a kappa type human immunoglobulin; and The constant region of the heavy chain includes or consists of the constant region of the heavy chain of a type IgG1 human immunoglobulin;

the said light chain of a kappa type human immunoglobulin and the said heavy chain of a type IgG1 human immunoglobulin being, in particular, the constant region of a light chain and the constant region of a heavy chain of a human immunoglobulin obtained through immunisation with the Rhesus D antigen.

Thus, the monoclonal antibody under the invention is not only capable of neutralising ricin via its variable regions, but also of facilitating ricin degradation by promoting its degradation by macrophages.

More specifically, the constant regions of the light chains and heavy chains of the monoclonal antibody under the invention derive from the IgG1s of an individual immunised with a Rhesus D antigen. Under another beneficial method of producing the invention, the monoclonal antibody described above and below possesses a light chain and, in particular, a constant region of the said light chain of the kappa (κ) type.

Under another beneficial method of production, the invention concerns a monoclonal antibody against ricin as described above, wherein:

The light chain of the said monoclonal antibody includes at least the complementarity-determining regions ($CDR_{Lm}$) of the variable region of a macaque immunoglobulin light chain; and The heavy chain of the said monoclonal antibody includes at least the complementarity-determining regions ($CDR_{Hm}$) of the variable region of a macaque immunoglobulin heavy chain.

The variable region of the light chain of the monoclonal antibody under the invention therefore includes at least the 3 CDRs of a macaque immunoglobulin, while the remainder of the variable region of the light chain may come from a macaque or from any other mammalian species, including humans.

The variable region of the heavy chain of the monoclonal antibody under the invention therefore includes at least the 3 CDRs of a macaque immunoglobulin, while the remainder of the variable region of the heavy chain may come from a macaque or from any other mammalian species, including humans.

When the variable region of the light chain of the monoclonal antibody only possesses the CDRs of the light chain of a macaque immunoglobulin, and the variable region of the heavy chain only possesses CDRs from the heavy chain of a macaque immunoglobulin, and all the remainder of the two variable regions derives from a human immunoglobulin, the antibody is then described as a humanized chimeric antibody.

Another beneficial method of producing the invention concerns a monoclonal antibody as defined above, wherein:

The variable region of the light chain of the said monoclonal antibody includes or comprises the following SEQ ID No 2 sequence:

```
                                          (SEQ ID NO 2)
Nter-ELQMTQSPSSLSASVGDRVTITCRASQSIRSYLAWYQQKPGKAPK

LLIYDAAHLQSGVPSRFSGSGSGTEFSLTISSLQPEDFAVYYCQQRNSYP

LTFGGGTKVEIK-Cter;
``` and

The variable region of the heavy chain of the said monoclonal antibody includes or comprises the following SEQ ID No 4 sequence:

```
                                          (SEQ ID NO 4)
Nter-QVQLVESGGGLVKPGGSLRLSCAASGFTFTDYYMDWVRQAPGKGL

EWVSRISPGGDVTWYADSVKGRFTISRDNAQNTLYLQMNSLRAEDTAVYF

CARDDIVVSRIFDDWGQGVLVTVSS-Cter.
```

Another beneficial method of producing the invention concerns a monoclonal antibody as defined above, wherein:

The variable region of the light chain of the said monoclonal antibody comprises the following SEQ ID No 2 sequence:

```
                                          (SEQ ID NO 2)
Nter-ELQMTQSPSSLSASVGDRVTITCRASQSIRSYLAWYQQKPGKAPK

LLIYDAAHLQSGVPSRFSGSGSGTEFSLTISSLQPEDFAVYYCQQRNSYP

LTFGGGTKVEIK-Cter;
``` and

The variable region of the heavy chain of the said monoclonal antibody comprises the following SEQ ID NO 4 sequence:

(SEQ ID NO 4)
Nter-QVQLVESGGGLVKPGGSLRLSCAASGFTFTDYYMDWVRQAPGKGL

EWVSRISPGGDVTWYADSVKGRFTISRDNAQNTLYLQMNSLRAEDTAVYF

CARDDIVVSRIFDDWGQGVLVTVSS-Cter.

REV8

Another beneficial method of producing the invention concerns a monoclonal antibody as defined above, including:
A light chain including or consisting of the following SEQ ID No 6 sequence:

Nter-ELQMTQSPSSLSASVGDRVTITCRASQSIRSYLAWYQQKPGKAPK

LLIYDAAHLQSGVPSRFSGSGSGTEFSLTISSLQPEDFAVYYCQQRNSYP

LTFGGGTKVEIKRTVAAPSVFIFPPSDEQLKSGTASVVCLLNNFYPREAK

VQWKVDNALQSGNSQESVTEQDSKDSTYSLSSTLTLSKADYEKHKVYACE

VTHQGLSSPVTKSFNRGEC-Cter;

and
A heavy chain including or consisting of the following SEQ ID No 8 sequence:

Nter-QVQLVESGGGLVKPGGSLRLSCAASGFTFTDYYMDWVRQAPGKGL

EWVSRISPGGDVTWYADSVKGRFTISRDNAQNTLYLQMNSLRAEDTAVYF

CARDDIVVSRIFDDWGQGVLVTVSSASTKGPSVFPLAPSSKSTSGGTAAL

GCLVKDYFPEPVTVSWNSGALTSGVHTFPAVLQSSGLYSLSSVVTVPSSS

LGTQTYICNVNHKPSNTKVDKKVEPKSCDKTHTCPPCPAPELLGGPSVFL

FPPKPKDTLMISRTPEVTCVVVDVSHEDPEVKFNWYVDGVEVHNAKTKPR

EEQYNSTYRVVSVLTVLHQDWLNGKEYKCKVSNKALPAPIEKTISKAKGQ

PREPQVYTLPPSRDELTKNQVSLTCLVKGFYPSDIAVEWESNGQPENNYK

TTPPVLDSDGSFFLYSKLTVDKSRWQQGNVFSCSVMHEALHNHYTQKSLS

LSPGK-Cter.

REV7

The invention also concerns a monoclonal antibody against ricin, as defined above, wherein:
The light chain of the said monoclonal antibody includes the leader region of the variable region of a human immunoglobulin light chain (LV$_{Lh}$),
The heavy chain of the said monoclonal antibody includes the leader region of the variable region of a human immunoglobulin heavy chain (LV$_{Hh}$).

Another beneficial method of producing the invention concerns a monoclonal antibody against ricin, as defined above, wherein:
The N-terminal region of the variable region of the light chain includes a signal sequence, particularly the leader region of the variable region of the light chain of a second immunoglobulin, specifically a human one; and
The N-terminal region of the variable region of the heavy chain includes a signal sequence, particularly the leader region of the variable region of the heavy chain of a third immunoglobulin, specifically a human one;
whereby the second and third immunoglobulins may be identical or different.

As stated above, the leader region or signal peptide, which is located in the N-terminal region of the variable region of the light chain and of the heavy chain, corresponds to a protein secretion sequence. During protein synthesis of the light chain and heavy chain, the said leader sequence means that the protein undergoing synthesis must remain in the light of the Rough Endoplasmic Reticulum (RER). This sequence is then eliminated from the mature light chain and from the mature heavy chain, so that the mature monoclonal antibody capable of interacting with ricin no longer possesses this sequence.

In addition, the invention concerns a precursor of an aforementioned monoclonal antibody, wherein:
The leader region LV$_{Lh}$ includes or consists of the following SEQ ID No 17 sequence:

Nter-MDMRVPAQLLGLLLLWLPGARC-Cter;

and
The leader region LV$_{Hh}$ includes or consists of the following SEQ ID No 18 sequence:

Nter-MKHLWFFLLLVAAPRWVLS-Cter . . .

Under another preferred means of production, the invention concerns a precursor of the monoclonal antibody described above, wherein:
The variable region of the light chain of the said monoclonal antibody includes or consists of the following SEQ ID No 10 sequence:

Nter-<u>MDMRVPAQLLGLLLLWLPGARC</u>ELQMTQSPSSLSASVGDRVTITC

RASQSIRSYLAWYQQKPGKAPKLLIYDAAHLQSGVPSRFSGSGSGTEFSL

TISSLQPEDFAVYYCQQRNSYPLTFGGGTKVEIK-Cter;

and
The variable region of the heavy chain of the said monoclonal antibody includes or consists of the following SEQ ID No 12 sequence:

Nter-<u>mkhlwfflllvaaprwvls</u>QVQLVESGGGLVKPGGSLRLSCAASG

FTFTDYYMDWVRQAPGKGLEWVSRISPGGDVTWYADSVKGRFTISRDNAQ

NTLYLQMNSLRAEDTAVYFCARDDIVVSRIFDDWGQGVLVTVSS-Cter.

In the aforementioned sequences (the sequences SEQ ID No 10 and SEQ ID No 12) those amino acids underlined whose "single-letter" coding symbol is in lower case correspond to the leader sequence amino acids. Those amino acids whose "single-letter" coding symbol is in upper case correspond to the variable region.

Under one beneficial method of production, the invention concerns a monoclonal antibody defined above, including:
A light chain consisting of the following SEQ ID No 14 sequence:

Nter-<u>MDMRVPAQLLGLLLLWLPGARC</u>ELQMTQSPSSLSASVGDRVTITC

RASQSIRSYLAWYQQKPGKAPKLLIYDAAHLQSGVPSRFSGSGSGTEFSL

TISSLQPEDFAVYYCQQRNSYPLTFGGGTKVEIKRTVAAPSVFIFPPSDE

QLKSGTASVVCLLNNFYPREAKVQWKVDNALQSGNSQESVTEQDSKDSTY

SLSSTLTLSKADYEKHKVYACEVTHQGLSSPVTKSFNRGEC-Cter;

and
A heavy chain consisting of the following SEQ ID No 16 sequence:

Nter-MKHLWFFLLLVAAPRWVLSQVQLVESGGGLVKPGGSLRLSCAAS

GFTFTDYYMDWVRQAPGKGLEWVSRISPGGDVTWYADSVKGRFTISRDN

AQNTLYLQMNSLRAEDTAVYFCARDDIVVSRIFDDWGQGVLVTVSSAST

KGPSVFPLAPSSKSTSGGTAALGCLVKDYFPEPVTVSWNSGALTSGVHT

FPAVLQSSGLYSLSSVVTVPSSSLGTQTYICNVNHKPSNTKVDKKVEPK

SCDKTHTCPPCPAPELLGGPSVFLFPPKPKDTLMISRTPEVTCVVVDVS

HEDPEVKFNWYVDGVEVHNAKTKPREEQYNSTYRVVSVLTVLHQDWLNG

KEYKCKVSNKALPAPIEKTISKAKGQPREPQVYTLPPSRDELTKNQVSL

TCLVKGFYPSDIAVEWESNGQPENNYKTTPPVLDSDGSFFLYSKLTVDK

SRWQQGNVFSCSVMHEALHNHYTQKSLSLSPGK-Cter

The invention also concerns the light chain of the monoclonal antibody defined above, specifically including the sequence SEQ ID No 6, and more particularly consisting of the sequence SEQ ID No 6 or SEQ ID No 14.

The invention also concerns the heavy chain defined above, specifically including the sequence SEQ ID No 8, and more particularly consisting of the sequence SEQ ID No 8 or SEQ ID No 16.

The invention also concerns a monoclonal antibody fragment as defined above, the said fragment being a Fab or F(ab)'2 fragment.

scFv fragments are excluded from the invention.

Thus, Fab and F(ab)'2 fragments are constituted of:

For Fab: a light chain including a constant region of a human immunoglobulin light chain and a variable region of a macaque immunoglobulin, and a heavy chain comprising a constant region of a human immunoglobulin heavy chain and a variable region of a macaque immunoglobulin;

For F(ab)'2, of the combination of the two Fabs described above via a disulphide bridge.

The object of the invention is also a nucleic acid including a sequence coding the light chain of the monoclonal antibody defined above, and specifically including the sequence SEQ ID No 1 or 5

Thus, under the invention the nucleic acid sequences are such that the sequence SEQ ID No 1 codes for the protein SEQ ID No 2, SEQ ID No 3 codes for the protein SEQ ID No 4, SEQ ID No 5 codes for the protein SEQ ID No 6, SEQ ID No 7 codes for the protein SEQ ID No 8, SEQ ID No 9 codes for the protein SEQ ID No 10, SEQ ID No 11 codes for the protein SEQ ID No 12, SEQ ID No 13 codes for the protein SEQ ID No 14 and SEQ ID No 15 codes for the protein SEQ ID No 16.

The object of the invention is also a nucleic acid including or constituted of a sequence coding the light chain of the monoclonal antibody defined above, and specifically including the sequence SEQ ID No 9 or 13.

Another beneficial method of production concerns a nucleic acid including or constituted of a sequence coding the heavy chain of the monoclonal antibody as defined above, specifically including the sequence SEQ ID 7.

Another beneficial method of production concerns a nucleic acid including or constituted of a sequence coding the heavy chain of the monoclonal antibody as defined above, specifically including the sequence SEQ ID 15.

Another beneficial method of producing the invention concerns a nucleic acid as defined above, including:

A nucleic acid, coding the light chain of the monoclonal antibody defined above, including or constituted of a sequence selected from among the nucleic acids SEQ ID No 1, 5, 9 and 13; and/or A nucleic acid, coding the heavy chain of the monoclonal antibody defined above, including or constituted of a sequence selected from among the nucleic acids SEQ ID No 3, 7, 11 and 15.

Another beneficial method of producing the invention concerns a nucleic acid including or constituted of a sequence coding the light chain of the monoclonal antibody as defined above, specifically including or constituted of any one of the sequences SEQ ID No 1, 5, 9 or 13.

Another beneficial method of producing the invention concerns a nucleic acid including a sequence coding the heavy chain of the monoclonal antibody defined above, specifically including or constituted of any one of the sequences SEQ ID No 3, 7, 11 or 15.

Another beneficial method of producing the invention concerns a nucleic acid as defined above, including:

A nucleic acid including or constituted of a sequence selected from among the nucleic acids SEQ ID No 1, 5, 9 and 13; and A nucleic acid including or constituted of a sequence selected from among the nucleic acids SEQ ID No 3, 7, 11 and 15.

Another beneficial method of producing the invention concerns a nucleic acid as defined above, including:

A nucleic acid including or constituted of the sequence SEQ ID No 5 or 13; and

A nucleic acid including or constituted of the sequence SEQ ID No 7 or 15.

Another beneficial method of producing the invention concerns a nucleic acid as defined above, including:

A nucleic acid including or constituted of the sequence SEQ ID No 13; and

A nucleic acid including or constituted of the sequence SEQ ID No 15.

Under another beneficial method of production, the invention concerns a nucleic acid including a sequence coding the light chain of the monoclonal antibody defined above and including a sequence coding the heavy chain of the monoclonal antibody defined above.

In other words, the aforementioned sequence includes, within a single molecule, or more specifically in the same strand, a sequence coding the light chain of the monoclonal antibody defined above followed by a sequence coding the heavy chain of the monoclonal antibody defined above. This also means that the aforementioned sequence includes, within a single molecule, a sequence coding the heavy chain of the monoclonal antibody defined above followed by a sequence coding the heavy chain of the monoclonal antibody defined above.

The invention also concerns an expression vector including at least one nucleic acid defined above, the said nucleic acid being under the control of elements allowing its expression.

Under the invention, "expression vector" is defined to mean a molecule of DNA that possesses elements allowing for its replication (duplication) in at least one living organism. In particular, these elements allowing for replication originate from the replication of yeast or bacteria, or from elements controlling the replication of a virus.

In particular, according to the invention, the vectors are plasmids, phages, yeast artificial chromosomes (YAC), bacterial artificial chromosomes (BAC), modified genomes of replicative or integrative viruses etc.

These are known as "expression" vectors because they possess nucleotide sequences that allow expression, namely the transcription into RNA of the nucleotide sequences that they control. Under the invention, the said nucleic acid sequence contained in the said vector is placed "under the control of elements allowing its expression". This means that the said expression vector possesses at least one transcription initiation sequence such as a virus promoter like the early promoter of the Simian Virus SV40 or of the Cytomegalovirus (CMV), or sequences promoting Rous Sarcoma Virus (RSV), and in particular a sequence or promoter including a TATA box. Furthermore, the said vector also possesses at least one transcription termination sequence, and in particular a polyadenylation sequence deriving from a mammalian, or more specifically a human gene.

Other sequences allowing for the regulation or modulation of the expression of the nucleotide sequence contained in the said vector may be added to those sequences indispensable to the expression of the said sequence. A non-exhaustive list includes: introns from mammalian, and particularly human genes, enhancement-type transcription regulation sequences ("enhancers") or sequences transcribed but not translated from mammalian, and particularly human genes.

One beneficial method of producing the invention concerns an expression vector as defined above, including at least one nucleic acid selected from among those nucleic acids including the following sequences SEQ ID No 1, 3, 5, 7, 9, 11, 13 and 15.

Another beneficial method of producing the invention concerns a combination comprising two expression vectors;
the first expression vector including a nucleic acid that includes a sequence selected from among the nucleic acids SEQ ID No 1, 5, 9 and 13; and
the second expression vector including a nucleic acid that includes a sequence selected from among the nucleic acids SEQ ID No 3, 7, 11 and 15.

Another beneficial method of producing the invention concerns a combination comprising two expression vectors, as above, wherein:
The first expression vector includes a nucleic acid that includes the sequence SEQ ID No 13; and
The second expression vector includes a nucleic acid that includes the sequence SEQ ID No 15.

Another beneficial method of producing the invention concerns an expression vector, as above, including:
A first nucleic acid selected from among the nucleic acids from the following sequences: SEQ ID No 1, 5, 9 and 13, the said first nucleic acid being under the control of elements allowing its expression; and
A second nucleic acid selected from among the nucleic acids from the following sequences: SEQ ID No 3, 7, 11 and 15, the said second nucleic acid being under the control of elements allowing its expression.

Another beneficial method of producing the invention concerns an expression vector, as above, including:
A first nucleic acid including or constituted of the sequence SEQ ID No 13, the said first nucleic acid being under the control of elements allowing its expression; and
A second nucleic acid including or constituted of the sequence SEQ ID No 15, the said second nucleic acid being under the control of elements allowing its expression.

This expression vector therefore includes two nucleic acid sequences, as above, and more specifically it includes a nucleic acid sequence coding the light chain of the monoclonal antibody defined above, and a nucleic acid sequence coding the heavy chain of the monoclonal antibody defined above.

By preference, the said expression vector contains a first element allowing the expression of the nucleic acid sequence coding the light chain of the monoclonal antibody defined above and a second element allowing the expression of the nucleic acid sequence coding the heavy chain of the monoclonal antibody defined above, the said first and the said second element allowing the expression of the said nucleic acid sequences being identical or different, and preferably identical. In particular, these control elements are the long terminal repeat (LTR) sequences of the RSV virus.

Another means of producing the invention concerns an expression vector defined above, including at least one antibiotic resistance gene.

Under the invention, "at least one [ . . . ] resistance gene" is defined to mean that the said expression vector may contain 1 or 2, or 3 or 4 or 5 or 6 antibiotic resistance genes.

Under the invention, "antibiotic resistance gene" is defined to mean a gene whose expression output exerts a cytostatic (growth inhibiting) or cytolytic (cell death) effect on cells. In particular, the antibiotics concerned by the invention have an effect on prokaryotic cells, but may also have an effect on eukaryotic cells, whether these are yeasts, plants, insects, amphibians or mammals.

More specifically, the aforementioned expression vector possesses an antibiotic resistance gene specific to prokaryotic cells and at least one or preferably 2 antibiotic resistance genes specific to eukaryotic cells.

The following can be cited as antibiotics specific to prokaryotic cells: Ampicillin, Tetracycline and its derivatives, Hygromycin, Kanamycin etc. The following can be cited as antibiotics specific to eukaryotic cells: G418, Geneticin (G418 salts), Puromycin, Methotrexate, Blasticidin etc.

More particularly, a mode of embodiment of the invention concerns an expression vector such as previously defined, comprising or consisting of the sequence SEQ ID No 21.

The transcriptional units (TU) of interest coding for the heavy chain and the light chain are cloned under the form of cDNA and under the dependence of the RSV promoter. This promoter corresponds to the LTR (Long Terminal Repeat) of the Rous sarcoma virus which contains an enhancer element in its region 5'.

An artificial intron optimised for alternate splicing is cloned immediately in region 3' of the promoter and is composed of a donor sequence in 5' isolated from the human beta-globin and in region 3' of the acceptor sequence derived from the variable gene of the immunoglobulin heavy chain. The TU's of interest end by sequences of polyadenylation derived from the growth hormone gene (GH) of human origin (hGH) for the heavy chain and bovine (bGH) for the light chain. This difference of origin in the choice of polyA is carried out with the aim of limiting the combinations between the genes of interest. This promoter association LTRRSV, chimeric intron, cDNA and polyA sequence has been selected because it confers a high transcriptional and translational activity in the cell line YB2/0.

In addition to the UT's of interest the expression vector contains several UT's resistant to some chemical molecules:

Bla gene: This gene (named Amp in the vector restriction maps) expresses the enzyme beta-lactamase in the bacteria (prokaryotic promoter) and confers a resistance to ampicillin.

Neo gene: This gene codes for the nptII enzyme (neomycin-phosphotransferase II) under the control of the SV40 promoter and confers a resistance to various antibiotics such as neomycin, kanamycin or G418 to the transfected mammalian cells expressing this gene.

Dhfr gene: This gene codes for the DHFR enzyme (DiHydroFolate Reductase) under the control of the SV40 promoter and confers a resistance to methotrexate (MTX). This process can be used to carry out gene amplification by increasing the concentration of MTX resulting from the increase in production of antibodies by the transfected cells.

The invention also seeks to have a cell, or several cells, or a cell line consisting of at least one expression vector such as previously defined.

The cells "consisting of at least one vector "correspond to the cells in which at least one expression vector mentioned above has been introduced.

Experts in this area of work know perfectly the techniques of molecular biology which allow the introduction of a DNA sequence or an expression vector to the interior of a cell, and notably with reference for example to (Sambrook, J et al. in Molecular Cloning: A Laboratory Manual. Cold Spring Harbor Laboratory Press, NY, Vol. 1, 2, 3 (1989). Thereafter the term "transfection" will be commonly used to describe the action of the introduction of a vector in a cell.

For example, the techniques of calcium phosphate transfection, by the use of lipidic particles or "lipofectants", or by techniques which allow the generation of holes in the cellular membrane by means of an electric shock (electroporation). This list is not exhaustive.

The cells or cellular lines utilised in the invention are cells from prokaryotes or eukaryotes such as bacteria, yeast or other mushrooms, insect cells, amphibian cells, mammalian cells and notably rodents, human cells . . . .

The cell is distinguished from the cellular line by the fact that the cellular line is a cellular population in an established culture, that is to say it has acquired the characteristics which allow their proliferation in vitro, and notably a characteristic of immortalisation.

A beneficial method of the invention concerns a cell or a cell line previously mentioned, presenting a substantially reduced fucosylation activity compared with a normal cell, the aforementioned cell or cell line being notably a mammalian cell, and in particular the YB2/0 line.

The favourable cell line of the invention is line YB2/0 available at the ATCC under number CRL 1662.

In another beneficial method, the invention concerns a cell or a cell line consisting of an expression vector defined above, permitting the expression of:
  a monoclonal antibody previously defined
  or of a light chain of a monoclonal antibody such as that previously described
  or of a heavy chain of a monoclonal antibody such as that previously described In another beneficial method, the invention concerns a cell or a cell line obtained by the cloning of an aforementioned cell.

The techniques of cellular cloning are largely known to experts in this field, and are based on the principle of the isolation of cells from a cellular population in order that each individual cell generates daughter cells (or clones) isolated from the daughter cells from the division of other cells of the population.

The general principal of cellular cloning is the limit dilution of cells.

Also, another beneficial method of the invention concerns a cell or a cell line from the aforementioned cloning, the said cells or cell line characterised by the fact that they:
  present an apoptosis of below 25%, and
  secrete at least cloning
  20 µg/ml of monoclonal antibody previously defined The measure of apoptosis, or programmed cell death, is made by techniques routinely employed by experts in this field which involve the evaluation of at least one of the stages characteristic of apoptosis: modification of the plasma membrane, modification of the proteins from the Caspase family, modification of the factors of transactions and fragmentation of DNA. Among the cells or cell lines obtained by cloning, the advantage of the invention is that the cells conserved are only those which produce a significant quantity of monoclonal antibody, and notably those which produce at least 20 µg/ml of monoclonal antibody. The measure of the quantity of antibody is easily achievable by the experts, using simple protein dosage techniques.

Another embodiment of the invention concerns a cell or a cell line obtained by the cloning of the aforementioned cell, notably characterised by the fact that:
  it presents an apoptosis of below 25%
  it is stable throughout cellular divisions, and
  it secretes at least 14 µg/ml of monoclonal antibody previously defined.

The notion of cellular stability implies that the cells from the cloning of cells cloned from cells containing at least one vector permitting the expression of a monoclonal antibody in accordance with the invention are capable during the different divisions of conserving their properties of resistance to antibiotics and of producing the monoclonal antibodies.

A further aspect of the invention concerns the pharmaceutical composition, in particular vaccinal, comprising at least
  one monoclonal antibody defined above, or
  one nucleic acid defined above, or
  one expression vector defined above, or
  one fragment of the said monoclonal antibody defined above,
combined with a vehicle pharmaceutically acceptable.

Advantageously, the invention involves a pharmaceutical composition, in particular vaccinal, consisting of at least one monoclonal antibody defined above, combined with an acceptable pharmaceutical vehicle.

The dosage of the active substance depends in particular on the mode of administration, and can be easily determined by an expert.

"A pharmaceutically acceptable vehicle" refers to a non-toxic material which is compatible with a biological system such as a cell, a cellular culture, a tissue or an organism. An effective therapeutic quantity can vary between 0.01 mg/kg and 50 mg/kg, preferably between 0.1 mg/kg and 20 mg/kg, and more preferably between 0.1 mg/kg and 2 mg/kg, in one or several daily administrations, over one or several days.

The pharmaceutical composition of the product can be administered intravenously, notably by injection or by gradual drip, subcutaneously, by systemic route, locally by means of infiltration, by bone, or by respiratory or pulmonary route by means of aerosol.

The preparations for parenteral administration can include sterile aqueous or non-aqueous solutions, suspensions or emulsions. Examples of non-aqueous solutions are propylene glycol, polyethylene glycol, vegetable oils, such as olive oil, or injectable organic esters such as ethyl oleate. Aqueous vehicles include water, alcohol/water solutions, emulsions or suspensions.

The favourable formulation for the pharmaceutical composition of the invention is an aerosol comprising
  a monoclonal antibody defined above, or
  a nucleic acid defined above, or an expression vector defined above, or a fragment of the said monoclonal antibody defined above, combined with an excipient, with or without a propulsion agent.

In one embodiment of the product, the aerosol presents in the form of a liquid containing the anti-ricin antibody and an excipient. Usually the excipient is alcohol, but any other excipient known by the experts could be utilised within the framework of the invention. A liquid form aerosol can be linked to a gas propellant such as chlorofluorocarbon (CFC) or hydro fluorocarbon (HFA).

The aerosol in liquid form can also be made up of lipidic micro particles and an excipient. In this case the excipients can be chosen from synthetic dipalmitoylphosphatidylcholine (DPPC), lactose or hydroxyethylamidon (HES). The micro particles are then administered with the aid of an insufflator.

In another embodiment of the invention the aerosol presents in powder form. The powder is composed of particles of sizes of between 1 and 10 µm and preferably smaller than 9 µm, or smaller than 5 µm. As a non-exhaustive guide, the following methods can be used to obtain a dry powder: pulverisation together with desiccation by freezing or crystallisation by ultrasound, controlled precipitation.

The administration of the aerosol will be carried out according to whether it presents in liquid or solid form with the aid of a nebuliser which can be pneumatic, ultrasonic or sieved or with the aid of a metered dose inhaler (pressurised liquid, mechanic, electrodynamic, thermic) for liquid formulations or with the aid of an inhaler for solid formulations. (Reychler G., Dessanges J F and Vecellio L, Respiratory Journal, 2007; 24:1013-1023).

The invention also includes the utilisation of at least:
one monoclonal antibody defined above, or
one fragment of the said monoclonal antibody defined above,
one nucleic acid defined above, or
one expression vector defined above, or
one cell defined above,
for the preparation of a drug for the treatment or prevention of a pathology linked to ricin contamination.

By treatment, we mean the method of treatment for a manifested pathology, whose symptoms are visible. By prevention, we mean the method of stopping the said pathology from manifesting.

Pathologies associated with ricin correspond to symptoms linked to ricin contamination, in particular diarrhoea, changes in electrolytes, dehydration, swelling, and respiratory, hepatic and renal problems . . . .

Equally the invention aims to achieve in vitro dosage of ricin in a biological sample taken from an individual susceptible to ricin contamination, the aforementioned method comprising:
placing the said sample in contact with at least one monoclonal antibody as previously defined, and
the determination of the presence or absence of ricin in the said sample by the detection of the formulation of an eventual immune complex between ricin and the said monoclonal antibody.

The monoclonal antibodies of the invention can therefore be utilised to detect the presence of ricin in a biological sample.

In particular, the said antibodies can be utilised for the implementation of detection techniques known by experts such as ELISA, RIE, immunoprecipitation or immunolabelling. (Western blot).

The invention also concerns an in vitro decontamination procedure, for a sample vulnerable to contamination by ricin, particularly a biological sample, which involves:
the placement of the said sample in contact with at least one of the above monoclonal antibodies, and
the elimination from the said sample of the immune complexes formed between ricin and the said monoclonal antibody.

A means of implementing the said decontamination procedure consists, for example, in the use of the invention's monoclonal antibodies, upon which magnetic spheres are grafted to the constant region of the said antibody.

Once the aforementioned antibodies, coupled with magnetic spheres, are placed in contact with the sample to be decontaminated, the ricin is eliminated from the sample by capturing the antibodies according to the invention, with magnets.

Another means to implement the said decontamination procedure consists, for example, in the use of monoclonal antibodies that have been immobilised on a column on which *Staphylococcus aureus* protein A or G is present. The sample to decontaminate is then passed through the column in order to capture, on the antibodies, according to the immobilised invention, any ricin which may be contained in the said sample.

One beneficial method of producing the invention concerns a procedure for the preparation of an aforementioned anti-ricin monoclonal antibody, which involves:
a. the transformation of a cell, particularly that of a mammal, specifically the YB2/0 line, with at least one vector defined above;
b. the selection of the transformed cells;
c. the evaluation of the production of the said antibody by the clones selected in the preceding stage, by determining the presence or absence of the formation of any immune complexes between the ricin and the said monoclonal antibody.

One beneficial method of producing the invention concerns a procedure defined above, in which the selection of transformed cells is achieved by determining their resistance to at least one antibiotic.

One beneficial method of producing the invention concerns a procedure defined above, in which the cells producing a quantity of the said monoclonal antibody greater than 22 µg/mL are selected.

One beneficial method of producing the invention concerns a procedure defined above, in which the cells selected in Step C are cloned.

One beneficial method of producing the invention concerns a procedure defined above, in which the cells selected in Step C are re-cloned for:
their resistance to at least one antibiotic, and
their capacity to produce at least 11 µg/mL of the said monoclonal antibody.

The invention is better illustrated by the following examples and figures. The examples below aim to clarify the object of the invention, and to illustrate beneficial methods of realising it, but in no way limit the scope of the invention.

BRIEF DESCRITION OF THE DRAWINGS

FIG. 1 corresponds to a schematic representation of an antibody. The black parts correspond to the constant regions of the heavy chains, the dark grey parts correspond to the constant region of the light chain, the parts in light grey correspond to the variable region of the heavy chain, and the white parts correspond to the variable region of the light chain. —S—S— represents the disulphide bridges between two cysteines. The CDR regions and structures are indicated by arrows. The Fab and Fc fragments are also represented.

FIG. 2 corresponds to a schematic pearl-necklace representation of the amino acid sequence of a variable section of the light chain or heavy chain of immunoglobulin. The black circles correspond to the amino acids forming the structured regions, and the grey circles correspond to the amino acids representing the CDRs.

FIG. 3 corresponds to a schematic representation of the bond between the leader peptide of the variable section of the heavy chain of a human immunoglobulin and the variable section of the heavy chain of a macaque immunoglobulin. The oligonucleotides which have served as PCRs are drawn on the schematic. The unique restriction sites are also indicated.

FIG. 4 corresponds to a schematic representation of the bond between the leader peptide of the variable region of the heavy chain of a human immunoglobulin and the variable region of the light chain of macaque immunoglobulin. The oligonucleotides which have served as PCRs are drawn on the schematic. The unique restriction sites are also indicated.

FIG. 5 corresponds to the schematic representation of the intermediate cloning vector H622-26 containing the 'double hybrid' heavy chain, in which the human leader is bound to the variable region of the macaque heavy chain (VH 43RCA), which is itself bound to the constant region of the human immunoglobulin (CH T125).

The different regulation elements (promoters, chimeric introns, polyadenylation sites, etc.), as well as the genes for resistance to antibiotics and the origins of replication, are also represented.

FIG. 6 corresponds to the schematic representation of the final cloning vector HK622-26 (SEQ ID No. 21) containing the 'double hybrid' heavy chain in which the human leader is bound to the variable region of the macaque heavy chain (VH 43RCA), which is itself bound to the constant region of the human immunoglobulin (CH T125), and the 'double hybrid' light chain in which the human leader is bound to the variable region of the macaque light chain (VK 43RCA), which itself is bound to the constant region of the human immunoglobulin (CK T125).

The different regulation elements (promoters, chimeric introns, polyadenylation sites, etc.), as well as the genes for resistance to antibiotics and the origins of replication, are also represented.

FIG. 7 corresponds to a 2% agarose gel on which the PCR products allowing the detection of the mycoplasms have been separated.

Bands 3 and 22 correspond to the migration of the molecular weight marker; bands 1 and 20 correspond to the migration of the PCR products made from a negative control, and bands 2 and 21 correspond to the migration of PCR products made from a positive control.

Bands 4, 6, 8, 10, 12, 14, 16, 18, 23, and 25 correspond to the migration of the PCR products made respectively from the cloid bases GG3, IF2, EE9, EG11, JB3, ED9, EC2, GF2, 1A1 and KC9.

Bands 5, 7, 9, 11, 13, 15, 17, 19, 24, and 26 correspond to the migration of the PCR products made respectively from the cloid bases GG3, IF2, EE9, EG11, JB3, ED9, EC2, GF2, 1A1 and KC9.

FIG. 8 represents in graph form the stability of antibody production for the three cloids EE9, GG3 and IF2. The grey bars represent measurements taken during the first dosage, and the black bars represent measurements taken during the second dosage.

The abscissa or x-axis represents time, in days, and the ordinate or y-axis represents the quantity of antibodies produced in ng/mL.

FIG. 9 corresponds to a 2% agarose gel on which the PCR products allowing the detection of the mycoplasms have been separated.

Bands 4, 17, 30 and 33 correspond to the migration of the molecular weight markers; bands 3 and 31 correspond to the migration of the PCR products made from a negative control, and bands 2 and 32 correspond to the migration of PCR products made from a positive control. Bands 5, 7, 9, 11, 13, 15, 18, 20, 22, 24, 26 and 28 correspond to the migration of the PCR products made respectively from the clone bases GG9-4B2, GG9-2F8, GG9-5D8, GG9-2G10, IF2-2F2, IF2-2E3, GG3-2G4, GG3-EC2, GG3-1G9, GG3-2G2, GG3-5G11, GG3-1D8 and EE9-5G7.

Bands 6, 8, 10, 12, 14, 16, 19, 21, 23, 25, 27 and 29 correspond to the migration of the PCR products made respectively from the clone bases GG9-4B2, GG9-2F8, GG9-5D8, GG9-2G10, IF2-2F2, IF2-2E3, GG3-2G4, GG3-EC2, GG3-1G9, GG3-2G2, GG3-5G11, GG3-1D8 and EE9-5G7.

FIG. 10 represents in graph form the stability of antibody production for the clones EE9-2G10, EE9-5D8, EE9-5G7, GG3-1G9, GG3-2G4, IF2-1C7, IF2-2D8 and IF2-2E9 over 8 days. The grey bars represent measurements taken during the first dosage, and the black bars represent measurements taken during the second dosage.

The abscissa or x-axis represents time, in days, and the ordinate or y-axis represents the quantity of antibodies produced in ng/mL.

Figure 13:
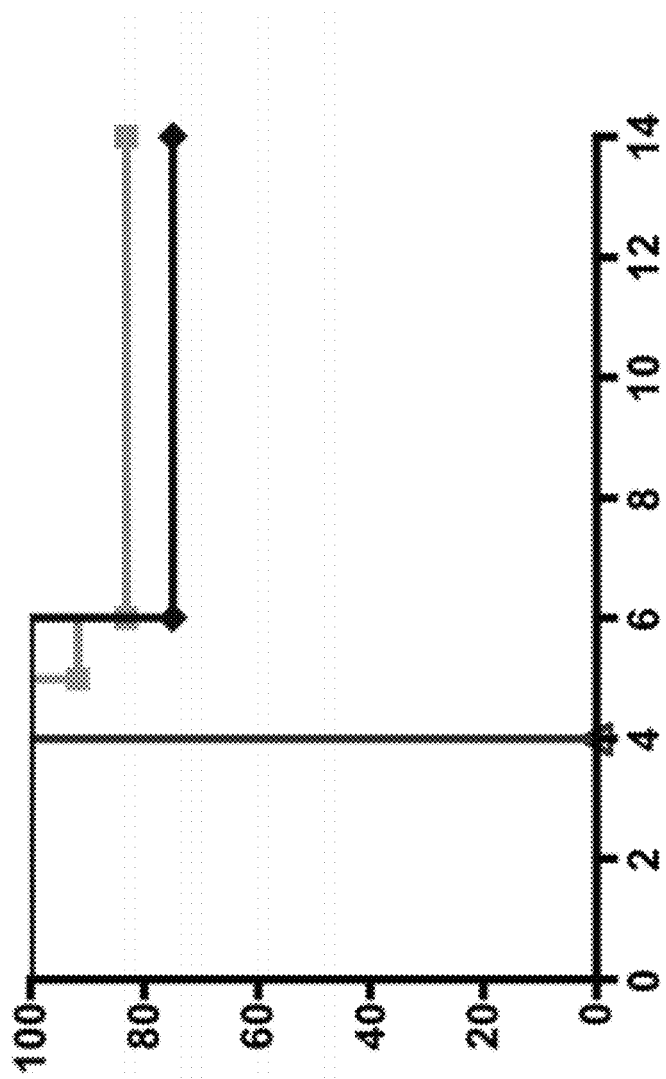

FIG. 13 represents the cumulative Kaplan-Meier survival curve for mice having received 50 µg of ricin by pulmonary instillation as well as 150 µg of the antibody according to the invention (43RCA), 44 hours (curve with squares), 54 hours (curve with diamonds) after the instillation of the ricin. A control (the curve with triangles) indicates the survival rate of mice treated with the ricin and a non-relevant immunoglobulin.

EXAMPLES

Example 1

Construction and Sequencing of an HK622-26 Expression Vector for the Expression of Antibodies According to the Invention The expression vector HK622-26 (SEQ ID No 21) was constructed for the expression of the chimeric macaque-human (IgG) anti-ricin monoclonal antibody.

The HK622-26 vector was constructed from the CHK622-05 vector by 'double chimerization,' meaning the addition by PCR of assemblies from human leader regions, and by a cloning addition of the constant CK and CH human regions to the VH and VK macaque variable sequences.

The variable heavy and light chain VH and VK regions are extracted from a coding vector for an anti-ricin ScFv, ScFv43RCA/H2-V116, and are introduced into the 'generic' CHK622-08 vector, after adding leader sequences to ensure a good synthesis of the chimerical antibody. The CK and CH constant regions are of human origin, and are derived from clone T125-A2, directed against the Rhesus D antigen.

A—Synthesis of the VH43RCA Region by PCR Assembly

The VH43RCA region corresponds to the chimerization of:

the leader VH sequence of the human M29812 sequence (in groups VH4, VH4-59), contained in the vector HK588-12, where the said leader VH sequence has been constituted in the following manner:

(SEQ ID NO 19)
5'-ATGAAACATCTGTGGTTCTTCCTTCTCCTGGTGGCAGCTCCCAGAT

GGGTCCTGTCC-3', and the macaque VH anti-ricin region contained in the plasmid phAil4 containing the fragment ScFv43RCA/H2-V116, where the said VH macaque sequence has been constituted from the SEQ ID No 3 sequence.

The chimerization is performed in the following manner:

the leader VH sequence (SEQ ID No 19) is amplified by PCR using the following initiator pair:

VH1-Ricin sense initiator:

(SEQ ID NO 22)
5'-CTCAGTGCTAGCGCCGCCACCATGAAACATCTGTGGT-3'

VH2-Ricin antisense initiator:

(SEQ ID NO 23)
5'-CCAGCTGCACCTGGGACAGGACCCAT-3' starting from a plasmidic HK558-12 DNA matrix.

The PCR reaction is performed according to the following protocol:

denaturation: 5 min. at 95° C.
denaturation: 0.5 min. at 95° C.⎤
hybridisation: 0.5 min at 50° C.} 10 repetitions
elongation: 0.5 min. at 72° C. ⎦
elongation: 10 min. at 72° C.

This pair of initiators allows the creation of an amplicon (amplicon 1) of 91 bases containing the site Nhe I (GCTAGC), the Kozak sequence (bold) and the human leader sequence SEQ ID No 17).

the macaque VH sequence (SEQ ID No 3) is amplified by PCR using the following initiator pair:

VH3-Ricin sense initiator:

(SEQ ID NO 24)
5'-ATGGGTCCTGTCCCAGGTGCAGCTGG-3'

VH4-Ricin antisense initiator:

(SEQ ID NO 25)
5'-ACCGATGGGCCCTTGGTGGAGGCTGAGGAGACGGTGACCA-3', starting with a plasmidic phAil4 DNA matrix.

The PCR reaction is performed according to the following protocol:

denaturation: 5 min. at 95° C.
denaturation: 0.5 min. at 95° C.⎤
hybridisation: 0.5 min at 50° C.}10 repetitions
elongation: 0.5 min. at 72° C.⎦
elongation: 10 min. at 72° C.

This initiator pair allows the creation of an amplicon (amplicon 2) of 396 bases containing the macaque VH sequence and the site Apa I (GGGCCCC).

Amplicons 1 and 2, previously obtained, are then combined to give the final amplicon 3 by PCR assembly using the aforementioned VH1 and VH4 initiators.

The PCR reaction is performed according to the following protocol:

denaturation: 5 min. at 95° C.
denaturation: 0.5 min. at 95° C. ⎤
hybridisation: 0.5 min at 50° C.} 15 repetitions
elongation: 1 min. at 72° C.⎦
elongation: 10 min. at 72° C.

FIG. 3 shows the VH43RCA region with the different initiator pairs having served in the preparation of the final chimerical VH fragment (amplicon 3) of 461 bp.

B-Synthesis of the VK43RCA Region by PCR Assembly

The VK43RCA region corresponds to the chimerization of:

the leader VK sequence of the human Z0006 sequence (in groups VK1, VK1-13), contained in the vector HK588-12, where the said leader VK sequence has been constituted in the following manner:

(SEQ ID NO 17)
5'-ATGGACATGAGGGTCCCCGCTCAGCTCCTGGGGCTTCTGCTGCTCT

GGCTCCCAGGTGCCAGATGT-3', and the macaque VK anti-ricin region contained in the plasmid phAil4 containing the fragment ScFv43RCA/H2-V116, where the said VH macaque sequence has been constituted from the SEQ ID No 1 sequence.

The chimerization is performed in the following manner:

the leader VK sequence (SEQ ID No 17) is amplified by PCR using the following initiator pair:

VK1-Ricin sense initiator:

(SEQ ID NO 26)
5'-CTCAGTACTAGTGCCGCCACCATGGACATGAGGGTCCCCG-3'

VK2-Ricin antisense initiator:

(SEQ ID NO 27)
5'-TGTCATCTGGAGCTCACATCTGGCACCTGG-3' starting from a plasmidic HK558-12 DNA matrix.

The PCR reaction is performed according to the following protocol:

denaturation: 5 min. at 95° C.
denaturation: 0.5 min. at 95° C.⎤
hybridisation: 0.5 min at 50° C.} 10 repetitions
elongation: 0.5 min. at 72° C.⎦
elongation: 10 min. at 72° C.

This pair of initiators allows the creation of an amplicon (amplicon 1') of 102 bases containing the site Spe I (ACTAGT), the Kozak sequence (bold) and the human leader sequence (SEQ ID No 19).

the macaque VK sequence (SEQ ID No 1) is amplified by PCR using the following initiator pair:

VK3-Ricin sense initiator:

(SEQ ID NO 28)
5'-CCAGGTGCCAGATGTGAGCTCCAGATGACA-3'

VK4-Ricin antisense initiator:

(SEQ ID NO 29)
5'-TGAAGA<u>CACTTGGTG</u>CAGCCACAGTTCGTTTGATCTCCACCTTGG
TCC-3' starting from a plasmidic phAil4 DNA matrix.

The PCR reaction is performed according to the following protocol:
denaturation: 5 min. at 95° C.
denaturation: 0.5 min. at 95° C.]
hybridisation: 0.5 min at 50° C.} 15 repetitions
elongation: 1 min. at 72° C.]
elongation: 10 min. at 72° C.

This initiator pair allows the creation of an amplicon (amplicon 2') of 364 bases containing the macaque VK sequence and the Dra III site (CACTTGGTG).

Amplicons 1' and 2', previously obtained, are then combined to give the final amplicon 3' by PCR assembly using the aforementioned VK1 and VK4 initiators.

The PCR reaction is performed according to the following protocol:
denaturation: 5 min. at 95° C.
denaturation: 0.5 min. at 95° C.]
hybridisation: 0.5 min at 50° C.} 15 repetitions
elongation: 1 min. at 72° C.]
elongation: 10 min. at 72° C.

Figure 1:
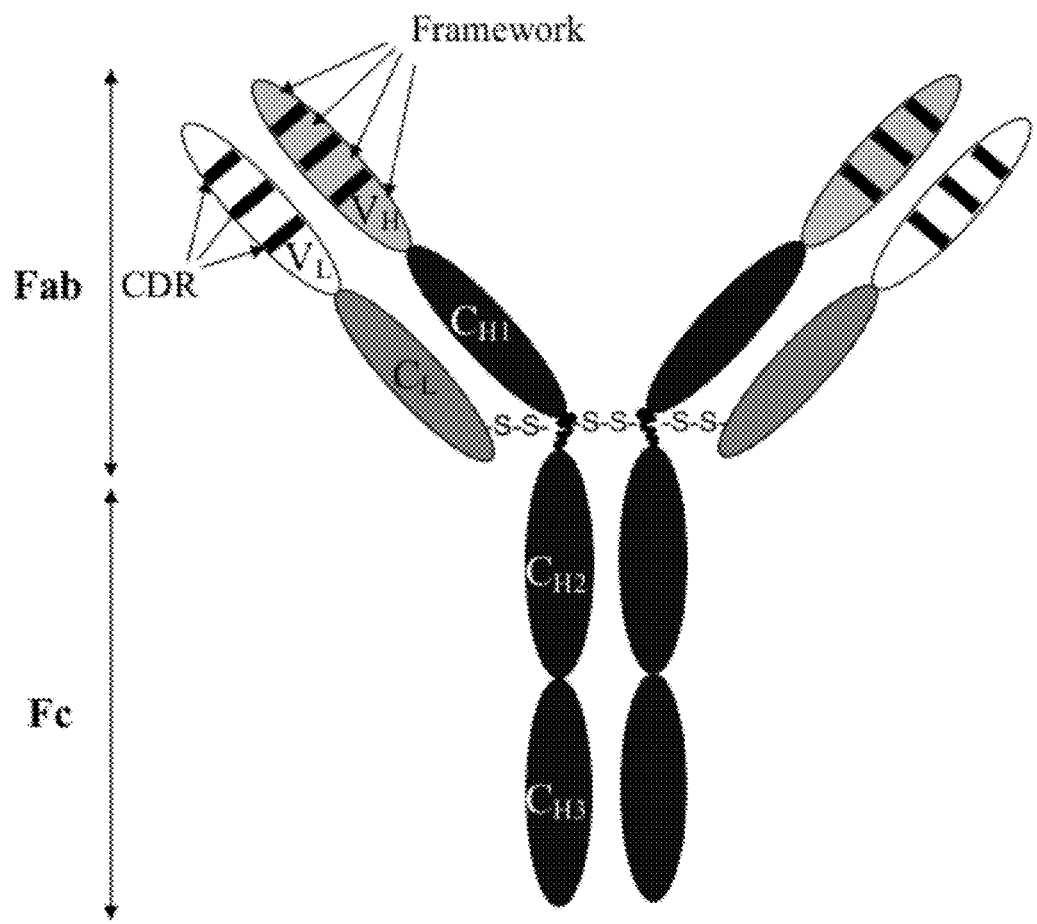
Figure 2:
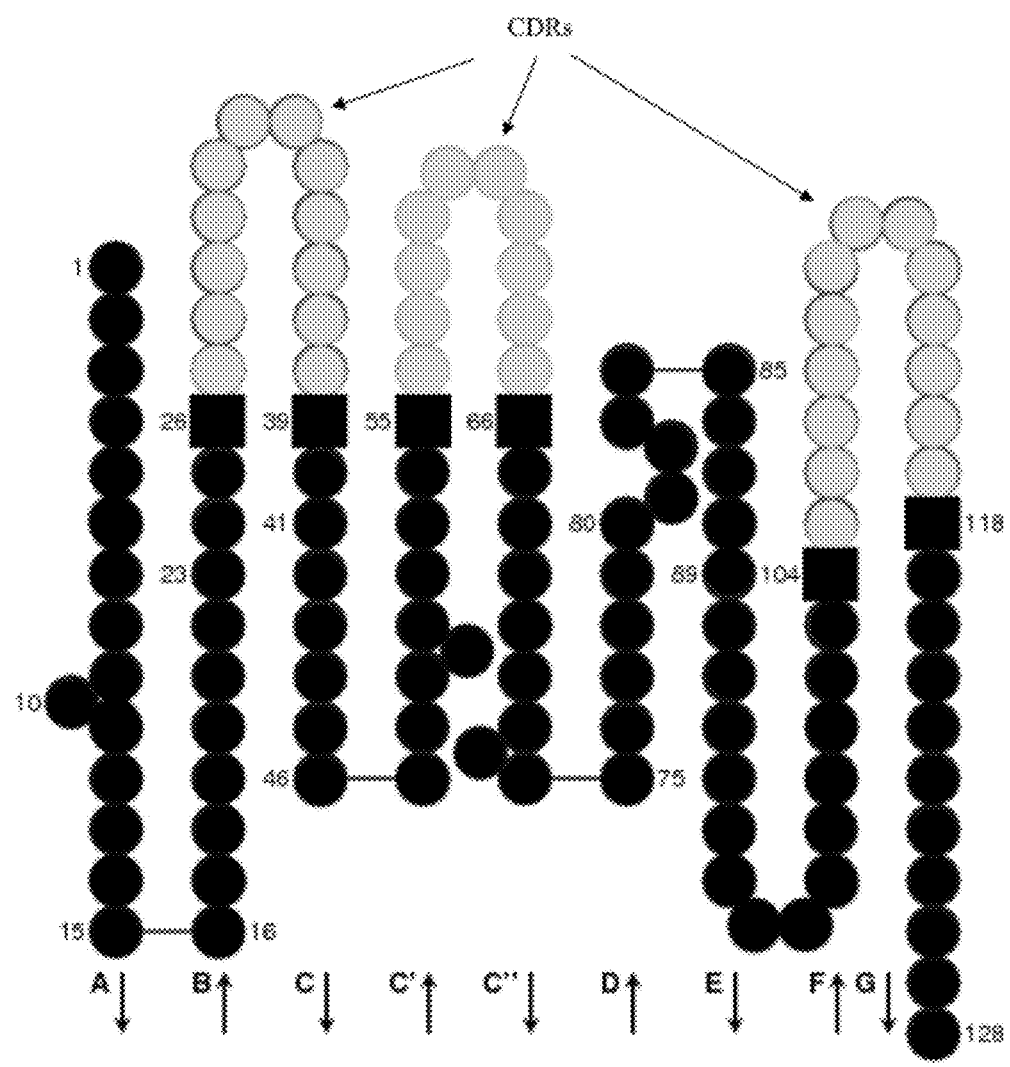
Figure 3:
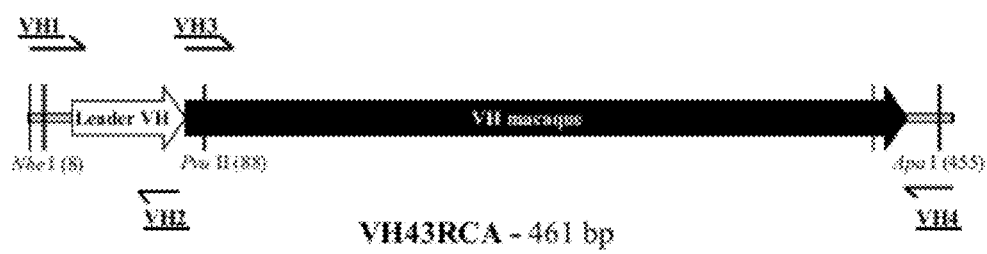
Figure 4:

FIG. 4 shows the VK43RCA region with the different initiator pairs having served in the preparation of the final chimeric VH fragment (amplicon 3') of 436 bp.

C-Construction of Vector H622-26

Amplicons 3 and 3' are introduced into the 'generic' vector CHK622-08 containing the constant CH heavy and CK light chain sequences from the IgG1 of the clone T125-A2 directed against the Rhesus D antigen.

The cloning of amplicons 3 and 3' is performed sequentially in the following way:

1—Amplicon 3 and the vector CHK622-08 are subjected to a double digestion by the restriction enzymes Nhe I–Apa I.

The digestion fragments are then purified, and a vector/amplicon 3 mixture is subjected to a cohesive ligation.

The products of the ligation are then used to transform bacteria, and the transformers are selected on an LB medium with an ampicillin complement.

The resistant clones are then tested by PCR by using the initiators SPRSVBIS and GSP2ANP: a fragment of 783 bp is expected for the positive clones.

⇒ 6 positive clones in PCR were selected for a screening via enzymatic digestion:
by Nhe I+Apa I control digestion (verification of the insert and junctions): The expected profile consists of 2 strips, 447+9917 bp, and
by Hind III digestion (verification of the entire vector): The expected profile consists of 4 strips, 3759+2894+2559+1152 bp.

Figure 5:
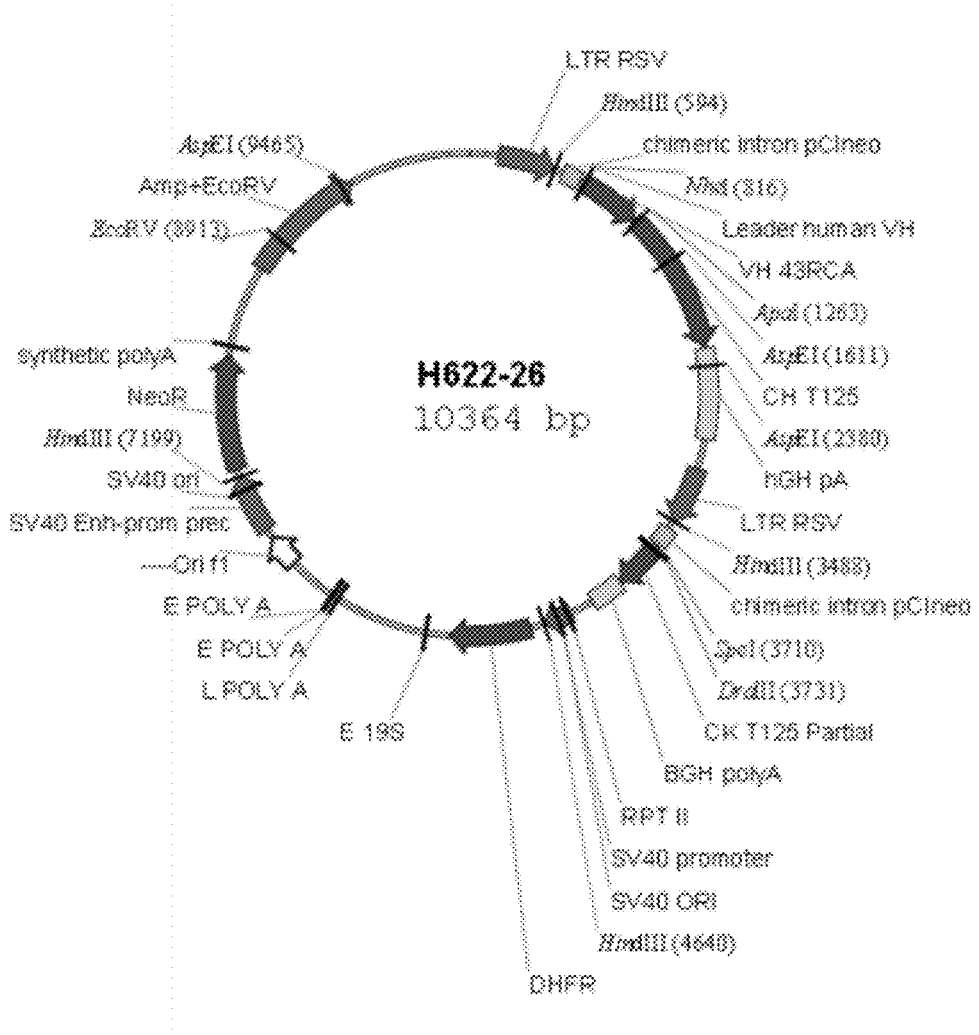

All of the clones are positive, and the H622-26 clone, whose restriction map is represented in FIG. 5, is chosen for the second step.

2—Amplicon 3' and the vector H622-26 are subjected to a double digestion by the restriction enzymes Spe I–Dra III.

The digestion fragments are then purified, and a vector/amplicon 3' mixture is subjected to a cohesive ligation.

The products of the ligation are then used to transform bacteria, and the transformers are selected on an LB medium with an ampicillin complement.

The resistant clones are then tested by PCR by using the initiators 5'1PLC and CK4: a fragment of 539 bp is expected for the positive clones.

⇒ 6 positive clones in PCR were selected for a screening via enzymatic digestion:
by Spe I+Dra III control digestion (verification of the insert and junctions): The expected profile consists of 2 strips, 420+10344 bp, and
by Hind III digestion (verification of the entire vector): The expected profile consists of 4 strips, 3759+2894+2559+1151 bp.

Figure 6:
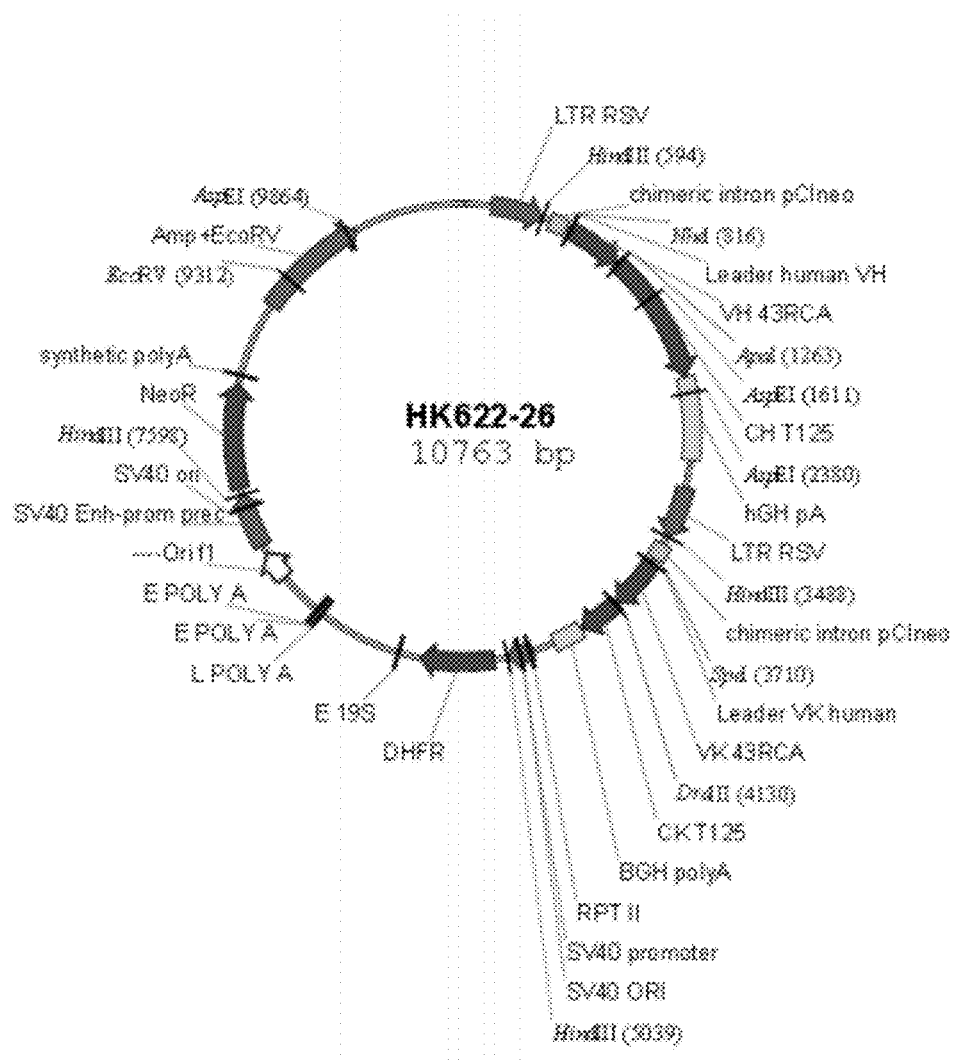

All of the clones are positive. After sequencing, only 4 clones possess a correct sequence. Clone 2 was chosen, and corresponds to vector H622-26. The restriction map of the vector H622-26 is represented in FIG. 6.

The vector is thus ready for the transformation of cells.

Example 2

Obtaining Anti-Ricin-Producing Clones in the YB2/0 Line by Direct Double Transfection This study has the aim of obtaining clones producing anti-ricin in the YB2/0 line by direct double transfection.

The YB2/0 cells were maintained (by re-treatment with $1 \times 10^5$ cell/ml twice per week) in light of transfection at $10^5$ cells/ml in an EMS medium, 5% SVF.

The vectors utilised for the transfection are as follows: HK622-26/EcoRV, H416-24 (T+) et K416-23 (T+). HK622-26/EcoRV signifies that the vector obtained in example 1 was linearised by digestion with the Eco RV enzyme in order to promote its integration into the transformed cells.

Transfection

The cells are transfected according to the following protocol:

4 cuvettes containing 500 μL of cells are prepared in the following manner:
Cuvettes 1 and 2: 42.8 μg of vector HK622-26/EcoRV
Positive control cuvette: 25.2 μg of vector H416-24, linearised;
23.2 μg of vector H416-23, linearised;
Negative control cuvette: no vectors.

The cells are then subjected to electrophoresis at a voltage of 230 V and a capacitance of 960 μF for 17.9 ms.

Once the electrophoresis is complete, the cells are carefully removed from the cuvettes and placed in a selective medium, RPMI, 5% dialysed SVF, 1 g/L geneticin for the P24 (25,000 cells/ml) and P96 at 100 cells/well (geneticin being applied only at J+3, once the resistance gene has been expressed) and in RPMI, 5% dialysed SVF, 0.5 g/L geneticin, 50 nM methotrexate (MTX) and seeded in culturing dishes in the following manner:
Cuvettes 1 and 2 (per cuvette): 1 plate, 24 wells, at 25,000 cells/well
5 plates, 96 wells, at 2500 cells/well
1 plate, 96 wells, at 100 cells/well
T+ Control cuvette: 1 plate, 96 wells, at 2500 cells/well
1 plate, 96 wells, at 100 cells/well
T– Control cuvette: 1 plate, 96 wells, at 2500 cells/well
1 plate, 96 wells, at 100 cells/well The cells are then cultivated in the presence of antibiotic for 4 weeks.

For the 96 well plates, the medium is changed twice per week.

The rest of the transformed cells are spread over 6 wells for each of cuvettes 1 and 2.

Selection of Transformers

Evaluation of the Production of Antibodies

In an initial step, the mean rate of antibody production is evaluated over 3 pools from each of the transfections of cuvettes 1 and 2, after 13 days in a selective culture medium.

In total 6 pools were tested, and the mean concentration of monoclonal antibodies was measured in µg/mL. The cellular density and cellular viability were also determined The results obtained are presented in Table 1 below:

TABLE 1

Viability and dosage of antibody production from the various pools.

| Cuvette | Pool | Cellular Density (10⁶ cells/ml) | Viability (%) | Antibody Concentration (µg/ml) |
|---|---|---|---|---|
| 1 | 1 | 0.62 | 82 | 5.6 |
|   | 2 | 0.52 | 74 | 5.1 |
|   | 3 | 0.44 | 88 | 4.2 |
| 2 | 1 | 0.62 | 84 | 3.6 |
|   | 2 | 0.72 | 86 | 5.8 |
|   | 3 | 0.52 | 72 | 6 |

We observe that the two transfections allow the production of anti-ricin monoclonal antibodies.

First Clonal Selection

After 22 days of culture in a selective medium, the appearance of clones resistant to G418 and to methotrexate was evaluated.

The results of the clones appearing are described in Table 2 below:

TABLE 2

Number of clones having emerged.

| Cuvette No. | Selection | Number of cells seeded per well | Number of P96 | Number of wells where clones emerged (total) | Number of wells where clones emerged/P96 |
|---|---|---|---|---|---|
| 1 | RPMI + 5% SVF dialysed + G418 0.5 g/L + 25 nM MTX | 2500 | 5 | 34 | 6.8 |
| 2 | RPMI + 5% SVF dialysed + G418 0.5 g/L + 25 nM MTX | 2500 | 5 | 42 | 8.4 |
| T+ | RPMI + 5% SVF dialysed + G418 0.5 g/L + 25 nM MTX | 2500 | 1 | 1 | 1 |

P96 = 96-well plates

In total 76 double resistant (G418 and methotrexate) pseudo-clones (wells) emerged following the double selection, for a transfection efficiency of 7.9% (76 positive wells for 960 seeded wells).

The cells which had been grown in the wells are considered as not being pure clones, as 2500 cells per well were seeded.

For each of the pseudo clones, or cloids, the quantity of immunoglobulin secreted was measured.

The results of the measurements from the best 24 clones are shown in Table 3 below:

TABLE 3 quantities of antibodies produced for the different cloids tested.

| Name of the cloid | 1 IgG ng/ml quantity | 2 IgG ng/mL quantity | 3 IgG ng/mL quantity | Average of the 3 IgG ng/mL quantities measured |
|---|---|---|---|---|
| BA1 | 4800 | 5862 | 5843 | 5502 |
| CB8 | 1700 | 1978 | 2253 | 1977 |
| CE10 | 1100 | 1283 | 1413 | 1265 |
| DH6 | 700 | 1405 | 2809 | 1638 |
| EC2 | 12300 | 13153 | 21402 | 15618 |
| EC9 | 9300 | 10638 | 11428 | 10455 |
| ED9 | 12300 | 13734 | 15564 | 13866 |
| EE9 | 22000 | 21738 | 24161 | 22633 |
| EG11 | 16800 | 15716 | 18330 | 16949 |
| GF11 | 6100 | 5529 | 6125 | 5918 |
| GF2 | 11000 | 11715 | 13187 | 11967 |
| GG3 | 27000 | 27371 | 28737 | 27703 |
| HC9 | 5200 | 6386 | 7151 | 6246 |
| HE7 | 8000 | 11015 | 13036 | 10684 |
| HE8 | 1400 | 1492 | 1764 | 1552 |
| IA1 | 10000 | 11779 | 12322 | 11367 |
| IA6 | 6300 | 4978 | 7044 | 6107 |
| IA7 | 3800 | 4887 | 5493 | 4727 |
| IF2 | 26000 | 29707 | 31385 | 29031 |
| JB3 | 16500 | 14736 | 17530 | 16255 |
| JB9 | 6600 | 6973 | 7970 | 7181 |
| JE6 | 8200 | 8626 | 9557 | 8794 |
| KB6 | 400 | 899 | 1165 | 821 |
| KC9 | 9900 | 7996 | 8832 | 8909 |

Of the 24 cloids tested, 10 had a monoclonal antibody production of more than 8.9 ng/mL. All these cloids (EC2, ED9, EE9, EG11, GF2, CG3, IA1, IF2, JB3 and KC9) were deep frozen in a medium without antibiotic, in the presence of 10% DMSO, and kept at −195° C. in liquid nitrogen.

Figure 7:
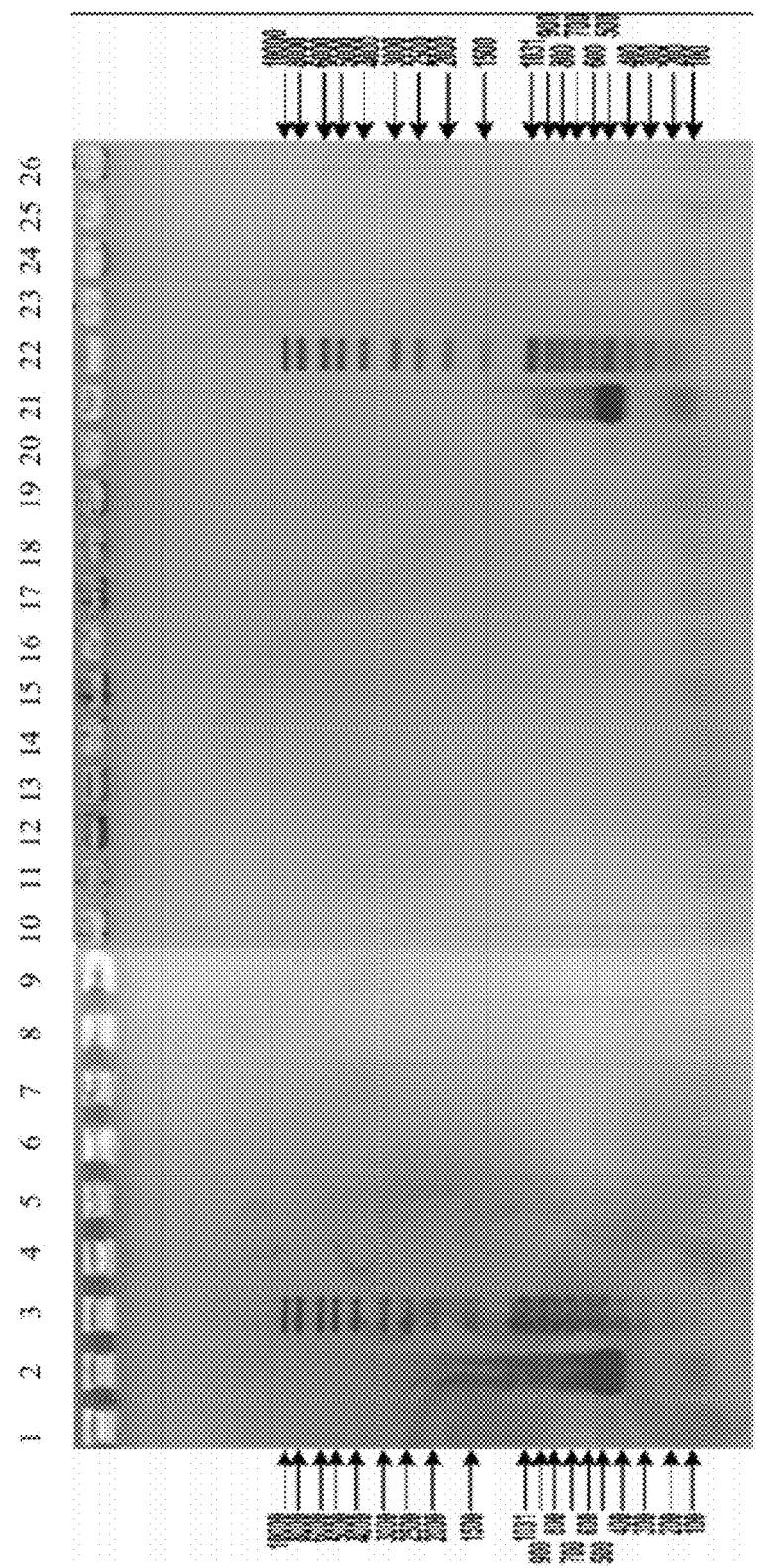

A cell viability test was conducted for each of these 10 cloids before freezing (Table 4) and they were screened for the possible presence of mycoplasma (FIG. 7).

All the clones had a satisfactory survival rate (>85%) and no clone was contaminated by mycoplasma.

TABLE 4 viability of the cloids

| Cloid | Viability (%) |
|---|---|
| GF2 | 89 |
| EE9 | 97 |
| IF2 | 89 |
| EG11 | 89 |
| KC9 | 85 |
| EC2 | 95 |
| ED9 | 95 |
| GG3 | 100 |
| IA1 | 100 |
| JB3 | 100 |

The 3 cloids (EE9, CG3 and IF2) whose production of antibodies was highest (more than 22 µg/mL) were selected for further cell cloning.

The stability of the monoclonal antibody production was also tested for each of the cloids selected.

The three cloids EE9, GG3 and IF2 were kept for 6 weeks by cascade dilution in 24 well plates in a DMEM medium+ 5% dialysed SVF and subcultured every 7 days. The production of monoclonal antibodies was evaluated in two independent ELISA assays and the results are shown in Table 5 below:

TABLE 5 antibody production over time.

| Name of the cloid | Week | Quantity 1 (ng/ml) | Quantity 2 ng/mL |
|---|---|---|---|
| EE9 | 1 | 13800 | 18415 |
| EE9 | 2 | 17000 | 22901.5 |
| EE9 | 3 | 17500 | 25188.5 |
| EE9 | 4 | 14400 | 23695 |
| EE9 | 5 | 16100 | 23878.5 |
| EE9 | 6 | 15000 | 19890.5 |
| GG3 | 1 | 14600 | 19131 |
| GG3 | 2 | 12500 | 18022 |
| GG3 | 3 | 9500 | 13153.5 |
| GG3 | 4 | 7200 | 9257.5 |
| GG3 | 5 | 5800 | 7270.5 |
| GG3 | 6 | 3000 | 4433.5 |
| IF2 | 1 | 12700 | 19743.5 |
| IF2 | 2 | 16300 | 21009.5 |
| IF2 | 3 | 12800 | 15733.5 |
| IF2 | 4 | 7800 | 12186.5 |
| IF2 | 5 | 10700 | 11822.5 |
| IF2 | 6 | 7100 | 10581.5 |

Figure 8:
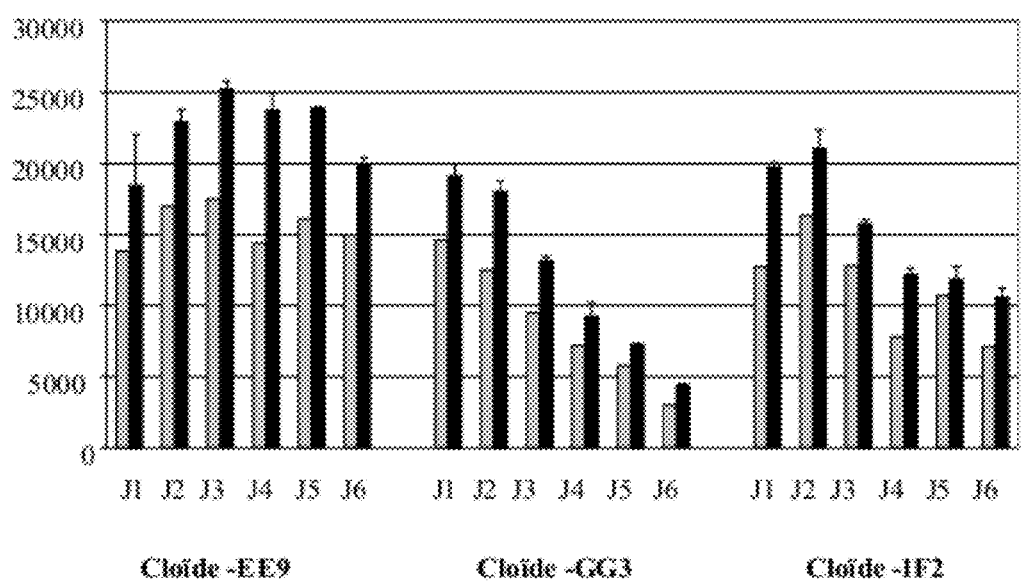

The stability of the cloids over time is also represented in graphic form in FIG. 8.

Of the 3 cloids selected, the GG3 cloid saw its production of antibodies go down very significantly during the various stages.

On the basis of this information, the cloids selected were recloned in order to achieve "pure" clones.

Second Clonal Selection

A second cloning of the cloids EE9, CG3 and IF2 was conducted in DMEM 5% dialysed SVF medium. 5×96 well plates, with 40 cells per well, were seeded in a DMEM 5% dialysed SVF medium. There was no clone for this cloning.

A second cloning was carried out in a DMEM and EMS 5% dialysed SVF medium.

The cells were unfrozen in a RPMI 5% dialysed SVF medium then passed into an EMS 5% dialysed SVF and DMEM 5% SVF medium. The cells were subcultured to $4.5 \cdot 10^5$ cellules/mL on the eve of cloning.

5×96 well plates, with 40 cells per well, were seeded per cloid and per medium, namely a total of 30 plates, or 2880 wells. The numbers of clones which appeared are shown in Table 6.

TABLE 6

Number of clones appearing

| Cloids | Medium | |
|---|---|---|
|  | DMEM | EMS |
| IF2 | 22 | 1 |
| GG3 | 30 | 0 |
| EE9 | 2 | 25 |

Table 6: number of clones which emerged after cloning the 3 cloids, as a function of the culture medium.

Two siftings using ELISA allowed the 10 best clones to be selected from the 80 cloid clones which emerged.

The ELISA results from the 11 clones produced from cloid EE9, the 11 clones produced from cloid GG3 and the 10 clones produced from cloid IF2, are shown in Table 7 below:

TABLE 7 quantities of antibodies produced for the different cloids tested.

| Culture Stage | Quantity 1 ng/mL | Quantity 2 ng/mL | Average E-IgG ng/mL |
|---|---|---|---|
| EE9 - 5G7 | 17 536 | 21 002 | 19 269 |
| EE9 - 5D8 | 14 572 | 14 647 | 14 610 |
| EE9 - 2G10 | 14 901 | 15 642 | 15 272 |
| EE9 - 2F8 | 4 198 | 5 433 | 4 816 |
| EE9 - 4B1 | 2 637 | 6 475 | 4 556 |
| EE9 - 1B6 | 3 773 | 4 865 | 4 319 |
| EE9 - 1G5 | 3 571 | 2 807 | 3 189 |
| EE9 - 3G4 | 1 715 | 2 255 | 1 985 |
| EE9 - 3G2 | 793 | 1 544 | 1 543 |
| EE9 - 4H3 | <1600 | 1 031 | 1 031 |
| EE9 - 4G9 | <1600 | 910 | 910 |
| GG3 - 2G4 | 21227 | 26174 | 23 701 |
| GG3 - 1G9 | 15816 | 18720 | 17 268 |
| GG3 - 2G2 | 11445 | 10988 | 11 217 |
| GG3 - 1D8 | 10 631 | 9 854 | 10 243 |
| GG3 - 5G11 | 6251 | 7283 | 6 767 |
| GG3 - 1F3 | 5 553 | 6 343 | 5 948 |
| GG3 - 2E7 | 6782 | 8059 | 7 421 |
| GG3 - 4F3 | 6060 | 5568 | 5 814 |
| GG3 - 1F7 | 3 340 | 5 158 | 4 249 |
| GG3 - 2B8 | 3898 | 5048 | 4 473 |
| GG3 - 4B9 | 1785 | 2933 | 2 359 |
| IF2 - 2E9 | 33267 | 42379 | 37 823 |
| IF2 - 2D8 | 28917 | 32700 | 30 809 |
| IF2 - 1C7 | 15770 | 18316 | 17 043 |
| IF2 - 1D5 | 11990 | 13224 | 12 607 |
| IF2 - 2F7 | 8386 | 8024 | 8 205 |
| IF2 - 4B7 | 4688 | 5222 | 4 955 |
| IF2 - 3D11 | 3147 | 6179 | 4 663 |
| IF2 - 3B6 | <1600 | 975 | 975 |
| IF2 - 2E10 | <1600 | 1234 | 1 234 |
| IF2 - 2C4 | <1600 | 761 | 761 |

5 clones were kept for each cloid. The 5 clones produced from cloid EE9 (EE9-5G7, EE9-5D8, EE9-2F8, EE9-4B1 and EE8-2G10) on average secrete more than 4.5 µg/mL monoclonal antibodies, the 5 clones from the cloid GG3 (GG3-2G4, GG3-1G9, GG3-2G2, GG3-1D8 and GG3-5G11) on average secrete more than 6.5 µg/mL monoclonal antibody and the 5 clones from the cloid IF2 (IF2-2E9, IF2-2D8, IF2-1C7, IF2-1D5 and IF2-2F7) secrete more than 8 µg/mL monoclonal antibody.

Figure 9:
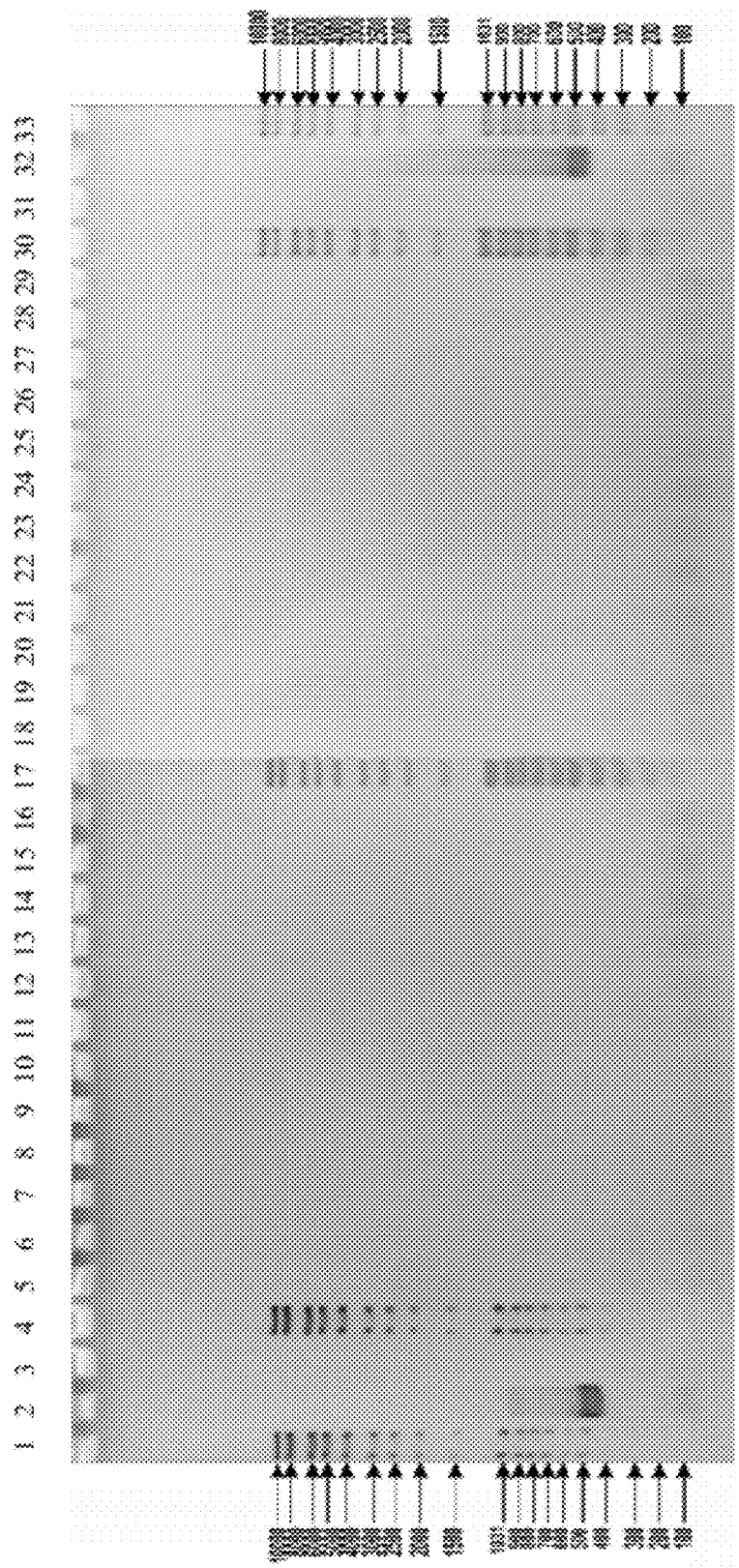

A cell viability test was conducted for each of these 15 cloids before freezing (Table 7) and they were screened for the possible presence of mycoplasma (FIG. 9).

All the clones had a satisfactory survival rate (>70%) and no clone was contaminated by mycoplasma.

TABLE 7 viability of the clones selected

| Clone | Viability (%) |
|---|---|
| GG3-2G4 | 78 |
| GG3-2G2 | 83 |
| GG3-1D8 | 86 |
| GG3-1G9 | 89 |
| GG3-5G11 | 78 |
| IF2-2F7 | 79 |
| IF2-1C7 | 75 |
| IF2-2D8 | 90 |
| IF2-2E9 | 71 |
| IF2-1D5 | 95 |
| EE9-2F8 | 80 |
| EE9-4B1 | 84 |
| EE9-5D8 | 85 |
| EE9-2G10 | 90 |
| EE9-5G7 | 93 |

Finally 8 clones were selected, based on the following criteria:

their production of monoclonal antibodies was ≧14 µg/mL
their viability was ≧70%

The clones selected were thus the following: EE9-5G7, EE9-5D8, EE9-2G10, GG3-2G4, GG3-1G9, IF2-2E9, IF2-2D8 and IF2-1C7.

Stability of the Clones

The aim of these experiments is to verify that the various clones secrete substantially the same quantity of monoclonal antibody through the different stages.

The eight clones selected were kept for 8 weeks by cascade dilution in 24 well plates and subcultured every 7 days. The clones from cloid EE9 were kept in a EMS+5% dialysed SVF medium and the clones from cloids GG3 and IF2 in a DMEM=5% dialysed SVF medium.

The production of monoclonal antibodies was evaluated in two independent ELISA assays and the results are shown in Table 8 below:

TABLE 8 antibody production over time.

| Name of the clones | Number of weeks | Average ng/mL | Average µg/mL |
| --- | --- | --- | --- |
| EE9-2G10 | 1 | 29592 | 30 |
|  | 2 | 4577 | 5 |
|  | 3 | 9019 | 9 |
|  | 4 | 20163 | 20 |
|  | 5 | 10908 | 11 |
|  | 6 | 10965 | 11 |
|  | 7 | 7848 | 8 |
|  | 8 | 5191 | 5 |
| EE9-5G7 | 1 | 31003 | 31 |
|  | 2 | 17087 | 17 |
|  | 3 | 21407 | 21 |
|  | 4 | 15508 | 16 |
|  | 5 | 12454 | 12 |
|  | 6 | 14053 | 14 |
|  | 7 | 13466 | 13 |
|  | 8 | 12404 | 12 |
| GG3-2G4 | 1 | 23966 | 24 |
|  | 2 | 22002 | 22 |
|  | 3 | 23668 | 24 |
|  | 4 | 23469 | 23 |
|  | 5 | 32319 | 32 |
|  | 6 | 32727 | 33 |
|  | 7 | 41491 | 41 |
|  | 8 | 47648 | 48 |
| IF2-2D8 | 1 | 39692 | 40 |
|  | 2 | 41974 | 42 |
|  | 3 | 33515 | 34 |
|  | 4 | 30602 | 31 |
|  | 5 | 29631 | 30 |
|  | 6 | 31373 | 31 |
|  | 7 | 35701 | 36 |
|  | 8 | 35279 | 35 |
| EE9-5D8 | 1 | 0 | 0 |
|  | 2 | 17072 | 17 |
|  | 3 | 21419 | 21 |
|  | 4 | 18034 | 18 |
|  | 5 | 13317 | 13 |
|  | 6 | 15010 | 15 |
|  | 7 | 14607 | 15 |
|  | 8 | 8543 | 9 |
| GG3-1G9 | 1 | 22030 | 22 |
|  | 2 | 18223 | 18 |
|  | 3 | 20848 | 21 |
|  | 4 | 26141 | 26 |
|  | 5 | 29579 | 30 |
|  | 6 | 31577 | 32 |
|  | 7 | 39374 | 39 |
|  | 8 | 60901 | 61 |
| IF2-1C7 | 1 | 18266 | 18 |
|  | 2 | 16667 | 17 |
|  | 3 | 18738 | 19 |
|  | 4 | 10165 | 10 |
|  | 5 | 7717 | 8 |
|  | 6 | 6852 | 7 |
|  | 7 | 8158 | 8 |
|  | 8 | 8675 | 9 |
| IF2-2E9 | 1 | 29219 | 29 |
|  | 2 | 30861 | 31 |
|  | 3 | 33623 | 34 |
|  | 4 | 28549 | 29 |
|  | 5 | 27918 | 28 |
|  | 6 | 36222 | 36 |
|  | 7 | 34909 | 35 |
|  | 8 | 38246 | 38 |

Figure 10:
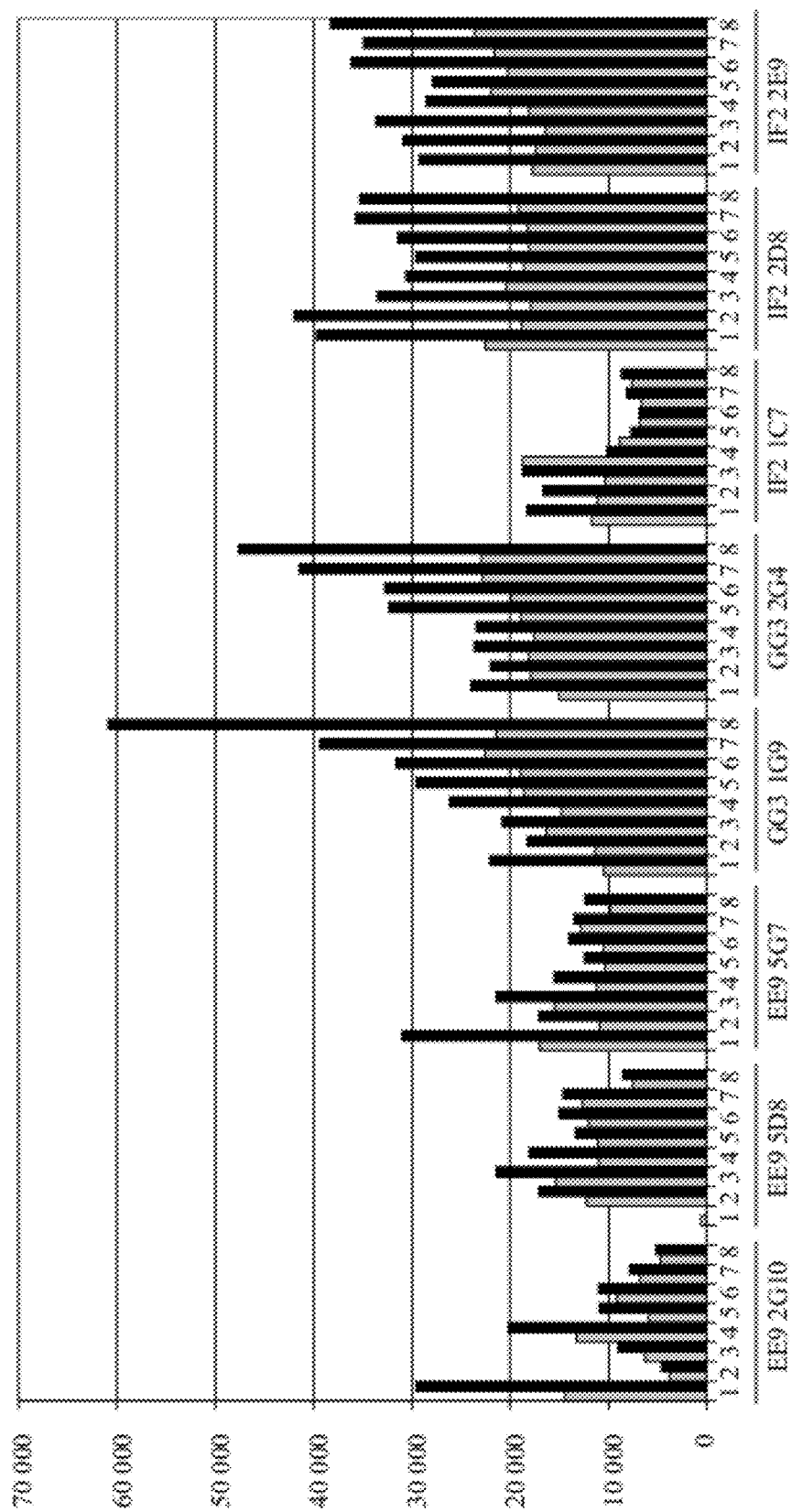

The stability of the cloids over time is also represented in graphic form in FIG. 10.

In the end, 3 clones were selected for their stability of monoclonal antibody production: clone EE9-5G7, clone IF2-2D8 and clone IF2-2E9.

Example 3

Production of Antibodies in Roller Bottles According to the Invention

The EE9-5G7 clone was selected for the production of 500 mg of antibodies on the basis of the dosages of maximum static pseudo production which established its level of production as 19 mg/L and also based on the results of the stability study conducted on the parental EE9 cloid, whose production level was stable for six weeks.

On the basis of these data, clone EE9-5G7 was amplified in such a way as to achieve two successive productions of 30 roller bottles in batch mode. Production was stopped when the cell viability dropped below 50%. As the supernatant measured at the end of production was only 12 mg/L, namely 648 mg antibody produced. This supernatant was measured, centrifuged, filtered before being concentrated 15 times. The concentrate was purified by affinity chromatography and this allowed 468 mg purified antibody to be obtained.

The production of anti-ricin monoclonal antibody by clones IF2-2D8 and IF2-2E9 was achieved by roller bottle production in an RPMI and EMS medium.

The cells were unfrozen and seeded to $2 \cdot 10^5$ cells/ml in a DMEM, 5% SVF medium depleted in Ig, 0.5 g/l geneticine. The viability from unfreezing was 91% for clone IF2-2D8 and 93% for clone IF2-2E9.

The progress of culture and roller production is shown in Table 9 for clone IF2-2D8 and in Table 10 for clone IF2-2E9.

TABLE 9

Follow-up of the culture and roller production of clone IF2-2D8

| Date | Concentration (×10⁶/ml) | Viability (%) | Subculture density (×10E6/ml) | Type of container | Volume of medium (ml) | Flask number | Medium |
|---|---|---|---|---|---|---|---|
| J0 | Change of medium | | | T75 | 30 | 2 | DMEM |
| J3 | −10 ml +10 ml medium | | | T75 | 30 | 2 | DMEM |
| J7 | 0.64 | 86 | 0.1 | T75 | 30 | 1 | DMEM |
| J10 | 1.1 | 95 | 0.1 | T75 | 30 | 1 | DMEM |
| J14 | 1.38 | 96 | 0.1 | T75 | 30 | 1 | DMEM |
| | | | | T75 | 30 | 1 | RPMI |
| | | | | T75 | 30 | 1 | EMS |
| J17 | 0.9 | 100 | 0.2 | T175 | 100 | 1 | RPMI |
| | 0.88 | 98 | 0.2 | T175 | 100 | 1 | EMS |
| J20 | 1.48 | 97 | 0.3 | Roller | 500 | 1 | EMS |
| | 1.12 | 100 | 0.3 | Roller | 400 | 1 | RPMI |
| J22 | 0.8 | 95 | 0.44 | Roller | 900 | Production Start | EMS |
| | 0.74 | 95 | 0.32 | Roller | 900 | Production Start | RPMI |
| J24 | 2.12 | 93 | | Roller | 900 | | EMS |
| | 0.92 | 96 | | Roller | 900 | | RPMI |
| J27 | | | Viability <50% Stop Roller | | | | EMS |
| | | | Viability <50% Stop Roller | | | | RPMI |

TABLE 10

Progress of culture and roller production of clone IF2-2E9

| Date | Concentration (×10⁶/ml) | Viability (%) | Cell density (×1E6/ml) | Type of container | Volume of medium (ml) | Flask Number | Medium |
|---|---|---|---|---|---|---|---|
| J0 | 0.56 | 82 | 0.1 | T75 | 30 | 1 | DMEM |
| J3 | 0.76 | 95 | 0.1 | T75 | 30 | 1 | DMEM |
| J7 | 1.4 | 91 | 0.1 | T75 | 30 | 1 | DMEM |
| | | | | | | 1 | EMS |
| | | | | | | 1 | RPMI |
| J10 | 0.68 | 100 | 0.1 | T75 | 30 | 1 | RPMI |
| | 0.9 | 100 | 0.1 | T75 | 30 | 1 | EMS |
| J14 | 0.98 | 98 | 0.2 | T175 | 100 | 1 | RPMI |
| | 1.2 | 91 | 0.2 | T175 | 100 | 1 | EMS |
| J17 | 1.26 | 95 | 0.25 | Roller | 500 | 1 | RPMI |
| | 1.12 | 96 | 0.22 | Roller | 500 | 1 | EMS |
| J20 | 1.74 | 92 | 0.9 | Roller | 900 | Production Start | RPMI |
| | 1.84 | 98 | 0.9 | Roller | 900 | Production Start | EMS |
| J22 | 1.54 | 90 | | Roller | 900 | 1 | RPMI |
| | 2.1 | 88 | | Roller | 900 | 1 | EMS |
| J24 | | | Viability <50% Stop roller | | | | RPMI |
| | | | Viability <50% Stop roller | | | | EMS |

The supernatants for these rollers were quantified by ELISA (Table 11), in order to measure the quantity of antibody produced.

TABLE 11

Doses of roller supernatants.

| Clones | Medium | Concentration (μg/ml) |
|---|---|---|
| IF2-2D8 | EMS | 39 |
| IF2-2D8 | RPMI | 32 |
| IF2-2E9 | EMS | 47 |
| IF2-2E9 | RPMI | 34 |

The supernatants were filtered through a 0.22 μm filter and the antibodies were purified by affinity chromatography on a HiTrap protein A FF column.

Purification assessment of the anti-ricin antibodies IF2-2D8 and IF2-2E9

| Name of clone | Culture medium | Culture supernatant Vol. (ml) | Culture supernatant IgG (mg) | Antibodies purified Vol. (ml) | Antibodies purified IgG (mg) | Yield (%) |
|---|---|---|---|---|---|---|
| IF2-2D8 | EMS | 1094 | 27.7 | 57.2 | 21.1 | 76.2 |
| IF2-2D8 | RPMI | 1096 | 21.7 | 11.6 | 16.1 | 74.2 |
| IF2-2E9 | EMS | 1095 | 38 | 17.2 | 32.8 | 86.3 |
| IF2-2E9 | RPMI | 1095 | 24.3 | 24.3 | 22 | 90.5 |

The concentrates allowed between 16 and 32.8 mg purified antibody to be obtained for each of the clones.

Clones IF2-2D8 and IF2-2E9 proved to be stable during the different stages (unlike their parental cloid) produce [sic]

twice as many monoclonal antibodies as clone EE9-5G7. The physico-chemical characterisation of the antibodies showed that it is clone IF2-2E9 which produced the antibody most like the antibody produced by clone EE9-5G7. For this reason, it was clone IF2-2E9 which was chosen for the next productions of anti-ricin antibodies Production and Purification of a Batch of 500 mg Anti-Ricin Antibody.

The culture supernatant for clone IF2-2E9 was concentrated, filtered, then the antibodies were purified in a first stage by affinity chromatography on Sepharose protein A followed by two stages of ion exchange. The quantity of antibody purified is 642 mg.

Example 4

In Vitro Test of Ricin Neutralisation by the Human/Macaque Chimeric Monoclonal Antibody—Survival Test This test measures the capacity of the antibodies forming the subject of the invention to protect J774A.1 cells which have come into contact with Ricin from dying.

Briefly, J774A.1 cells (ATCC-LGC, Molsheim, France) were seeded at a density of 14.000 cells/well (200 µl/well), in a culture plate and cultivated at 37° C. in the presence of 5% $CO_2$ for 24 hours in a DMEM medium complemented by 10% fcetal vole serum. The antibodies forming the subject of the invention were incubated with 480 ng/ml ricin or with control serum (antibodies not relevant) for one hour. The mixture was then added to the cells. 24 hours afterwards, cell viability was measured by techniques known to the expert in the field (Trypan Blue Exclusion Test, Cytox (Promega), measurement of apoptosis . . . ). Each test was corrected in relation to the "100% cell viability" controls (no ricin and no antibodies) and "0%" viability (ricin without antibodies).

Example 5

In Vitro Test of Ricin Neutralisation by the Human/Macaque Chimeric Monoclonal Antibody—Translation Inhibition Test Another test may be used for measuring the neutralising activity of the monoclonal antibodies forming the subject of the invention, this means measuring protein translation inhibition. To do this, the translation of a marker protein is measured, for example the translation of luciferase, in an acellular in vitro translation system [Hale M L *Pharmacol Toxicol* 2001, 88(5):255-260]. Briefly, the test for measuring the translation of the luciferase messenger RNA is the following: The monoclonal antibodies are placed in 96 well plates in phosphate buffered saline (PBS) and ricin is added at a final concentration of 4 mM. Rabbit reticulocyte lysate complemented by RNAsin®, amino acids of the luciferase messenger RNA is then added to each well. The reaction is achieved over 1.5 hours.

5 µL of the reaction are then taken and added to 45 µL of reactional buffer solution, allowing luciferase activity to be detected (Luciferase assay reagent, Promega, Inc.). The light emitted (luminescence) is measured in counts per second (CPS) with the aid of a Victor multi-plate reader (PerkinElmer Wallac, Boston Mass.). The data are expressed as a percentage compared to a control (% control=(CPS treated/CPS control)×100)).

In the two tests (Example 4 and Example 5), the comparison between the 50% protecting dose of scFv (1 µg/ml) and that of the IgG (0.5 µg/ml) shows a net benefit of the expression in the form of IgG.

Example 6

In Vivo Test of Ricin Neutralisation by the Human/Macaque Chimeric Monoclonal Antibody In order to test the neutralising effect of the anti-ricin antibody in vivo, Fisher rats (Charles River Laboratories L'Arbresle, France) received a dose of 16 µg/kg by weight of ricin and 50 µg anti-ricin antibody, following an adjustment of the protocol described by Ezzell et al. (Ezzell, et al. 1984. Infect. Immun 45:761-767)

The tests were carried out by measuring the viability of the animals as a function of the doses of ricin and of anti-ricin antibodies injected.

As a control, the viability of the rats treated solely with the ricin (positive test) and the rats treated solely with the anti-ricin antibody (negative test) was also evaluated.

Example 7

Affinity Assay of the Human/Macaque Chimeric Monoclonal Antibody for Ricin

The affinity assay of the anti-ricin antibody for its antigen, that is to say ricin, was measured by surface plasmon resonance by means of a BIAcore X instrument (Biacore, Uppsala, Sweden). The ricin was immobilised on a CM5 chip (Biacore), by means of an amine coupling, in accordance with the manufacturer's instructions.

For each measurement, a minimum of six dilutions, in an HBS-EP (Biacore) buffer of anti-ricin antibody was tested for 900s (dilutions from 10 to 0.1 µg/mL). After each dilution of the antibody, the chip was regenerated with 1.5 glycin (Biacore) at a flow of 10 µl/min for 30s. The affinity constants were calculating by using the method described by Karlsson et al. (Karlsson et al. 1991, J. Immunol. Methods 145:229-240) and checked using internal tests as described by Schuck, et al. (Schuck, P., and A. P. Minton. 1996. Anal. Biochem. 240:262-272).

Example 8

Administration of the Human/Macaque Chimeric Monoclonal Antibody to Mice by Instillation and Determination of Survival BALb/c mice (20-22 g) were exposed to ricin by pulmonary instillation at the level of 16 µg/kg body weight and survival was checked 10 days after administration of the ricin.

The anti-chain A IgG 43RCA type of ricin antibody or a human IgG control were administered by pulmonary instillation at a level of 50 µg. The protective effect of the anti-chain A IgG 43RCA type of ricin antibody was measured by the percentage of mice which survived and by the ratio of wet weight over dry weight in the lungs, taking account of the fact that ricin induces pulmonary oedema.

Figure 11:
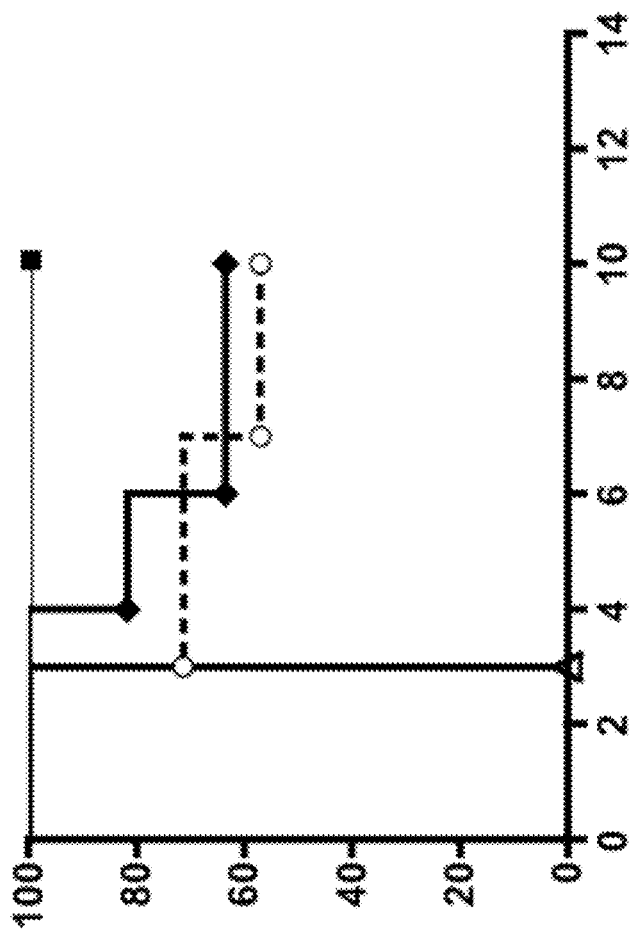
FIG. 11 represents the cumulative Kaplan-Meier curve for mice having received 50 µg of ricin by pulmonary instillation as well as a control human IgG (curve with triangles), or the antibody according to the invention (43RCA), 6 hours (curve with squares), 22 hours (curve with diamonds) or 24 hours (dashed curve with circles) after the instillation of the ricin.

The mice exposed to the ricin who had received the human control IgG were all dead by Day 3 3 (0% survival) (n=4). 100% survival was observed in the mice which had received the ricin and the 43RCA antibody in the same injection (n=2, not represented in FIG. 11)

The mice which had received the 43RCA antibody 6 hours after administration of the ricin also revealed 100% survival (n=7)

Among the mice which had received the 43RCA antibody 22 hours after the administration of the ricin (n=7), 2 died on day 4, 1 died on Day 8 and the other 4 mice survived. The survival percentage is equal to 57.1% when the antibody is administered 22 hours after the administration of the ricin by the pulmonary route. Among the mice which had received the 43RCA antibody 24 hours after the administration of the ricin (n=11), 2 died on day 4, 2 died on Day 6. On Day 10, 7 of the 11 mice had survived. The survival rate is equal to 63.6%

The ratio of wet weight to dry weight of the lungs was measured 3 days after administration of the ricin to the mice, whether or not they received the 43RCA antibody. As shown in the table below, the ratio goes down if the mice receive the ricin pre-mixed with the 43RCA antibody, demonstrating that this 43RCA antibody neutralises the toxicity of the toxin and limits oedema of the lungs.

|  | Ratio wet weight/dry weight of the lungs | SD |
| --- | --- | --- |
| Saline Solution | 4.47 | 0.31 |
| Ricin | 6.56 | 0.655 |
| Ricin + 43RCA IgG | 5.36 | 0.607 |

Example 9

Administration of the Human/Macaque Chimeric Monoclonal Antibody to Mice by Instillation and Determination of Minimum Doses BALb/c mice were exposed to ricin by pulmonary instillation at a level of 16 µg/kg body weight and received an administration of 43RCA 6 hours afterwards, as 1, 5, 10, 20 µg.

Figure 12:
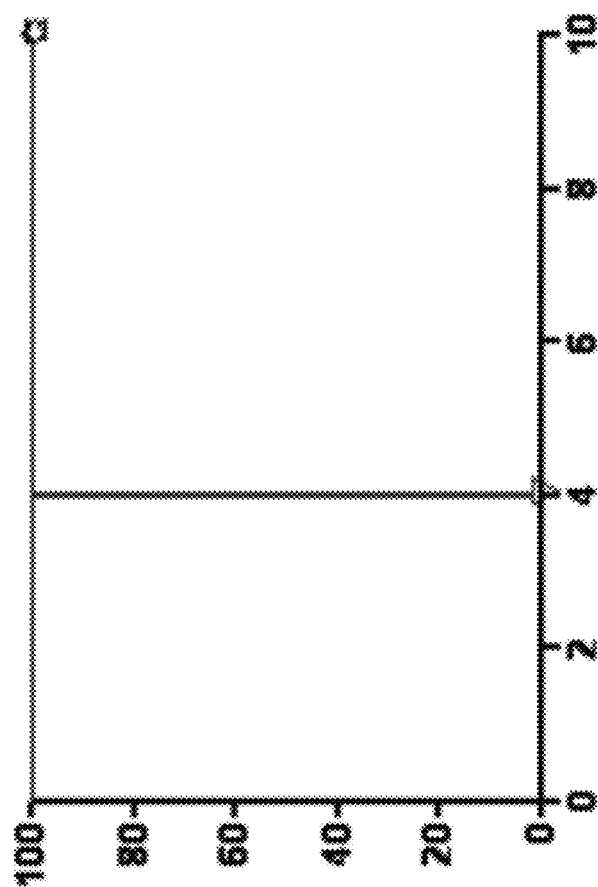
FIG. 12 represents the cumulative Kaplan-Meier survival curve for mice having received 50 µg of ricin by pulmonary instillation as well as 20 µg of control human IgG (curve with triangles), or the antibody according to the invention (43RCA) at a concentration of 20, 10, 5 and 1 µg.

FIG. 12 shows that whatever the dose administered, 100% survival rate is observed in the mice. The 43RCA antibody proved to be therapeutically effective from 1 µg upwards when it is administered 6 hours after intoxication by ricin.

BALb/c mice were exposed to ricin by pulmonary instillation at a level of 16 µg/kg body weight and survival was checked for 10 days after administration of the ricin. The anti-chain A IgG 43RCA type of ricin antibody or a human IgG control were administered by pulmonary instillation at a level of 150 mg.

As shown in FIG. 13, the mice which had received the ricin and an IgG control all died on Day 4. The mice which had received the 43RCA antibody 44 hours after the pulmonary administration of ricin had a survival rate of 83% (n=12). The mice which had received the 43RCA antibody 54 hours after the pulmonary administration of ricin had a survival rate of 75% (n=8). The 43RCA antibody therefore has a therapeutic effect even when it is administered more than two days after intoxication by ricin.

Example 10

Administration of the Human/Macaque Chimeric Monoclonal Antibody by Aerosol

The mice were exposed to aerosols containing ricin and the anti-ricin antibody obtained by a Collison nebuliser (mass median aerodynamic diameter [MMAD]=1.2 um).

The concentrations of ricin and antibody were identical for each exposure (ricin=1 mg/ml, antibody=14 mg/ml); the aerosol concentration being determined by the exposure time.

The aerosols were continually measured during exposure by means of a glass impact tester (AGI). The concentration of protein collected in the impact tester was measured by using the BCA micro protein assay kit (Pierce Co., Rockford, Ill., U.S.A.)

The diffusion conditions for the aerosols and their recovery remained constant throughout the study. The aerosol concentration (µg/L) was calculated and the dose of ricin inhale [sic] (µg/mouse) was estimated by using the Guyton formula.

---

The invention claimed is:

1. A chimeric anti-ricin monoclonal antibody, comprising the light chain variable region as set forth in SEQ ID NO: 2 and the heavy chain variable region as set forth in SEQ ID NO: 4, or an Fab or F(ab')$_2$ fragment thereof.

2. The antibody of claim 1, comprising human heavy chain and light chain constant regions.

3. The antibody of claim 2, wherein the heavy chain constant region is an IgG$_1$ constant region and the light chain constant region is a kappa constant region.

4. The antibody of claim 1, wherein the light chain comprises SEQ ID NO: 6 and the heavy chain comprises SEQ ID NO: 8.

5. The antibody of claim 1, comprising the light chain variable region as set forth in SEQ ID NO: 10 and the heavy chain variable region as set forth in SEQ ID NO: 12, or an Fab or F(ab')$_2$ fragment thereof.

6. The antibody of claim 1, comprising the light chain as set forth in SEQ ID NO: 14 and the heavy chain as set forth in SEQ ID NO: 16, or an Fab or F(ab')$_2$ fragment thereof.

7. A pharmaceutical composition comprising the antibody of claim 1, or an Fab or F(ab')$_2$ fragment thereof, and a pharmaceutically acceptable vehicle.

8. The pharmaceutical composition of claim 7, wherein the composition is a vaccinal composition.

9. The pharmaceutical composition of claim 7, formulated as an intravenous, parenteral or aerosol composition to treat ricin contamination.

10. A method of treating ricin contamination, comprising administering a therapeutically effective amount of the composition of claim 7 to a subject in need thereof.

11. The method of claim 10, wherein the therapeutically effective amount of the composition is 0.1-2 mg/kg.

12. The antibody of claim 1, capable of inhibiting ricin toxicity.

* * * * *

SEQUENCE LISTING

<160> NUMBER OF SEQ ID NOS: 29

<210> SEQ ID NO 1
<211> LENGTH: 321
<212> TYPE: DNA
<213> ORGANISM: Macaca fascicularis
<220> FEATURE:
<221> NAME/KEY: CDS
<222> LOCATION: (1)..(321)

<400> SEQUENCE: 1

```
gag ctc cag atg aca cag tct cca tcc tcc ctg tct gca tct gta gga      48
Glu Leu Gln Met Thr Gln Ser Pro Ser Ser Leu Ser Ala Ser Val Gly
1               5                   10                  15 gac aga gtc acc atc act tgt cgg gca agt cag agc att aga agt tat      96
Asp Arg Val Thr Ile Thr Cys Arg Ala Ser Gln Ser Ile Arg Ser Tyr
            20                  25                  30 tta gcc tgg tat cag cag aaa cca ggg aaa gcc cct aag ctc ctg atc     144
Leu Ala Trp Tyr Gln Gln Lys Pro Gly Lys Ala Pro Lys Leu Leu Ile
        35                  40                  45 tat gat gca gcc cat ttg caa agt ggg gtc cca tca agg ttc agc ggc     192
Tyr Asp Ala Ala His Leu Gln Ser Gly Val Pro Ser Arg Phe Ser Gly
    50                  55                  60
```

```
agt gga tct ggg aca gaa ttc agt ctc acc atc agc agc ctg caa cct      240
Ser Gly Ser Gly Thr Glu Phe Ser Leu Thr Ile Ser Ser Leu Gln Pro
65                  70                  75                  80 gaa gat ttt gca gtt tat tac tgt caa cag cgt aat agt tat cct ctg      288
Glu Asp Phe Ala Val Tyr Tyr Cys Gln Gln Arg Asn Ser Tyr Pro Leu
                85                  90                  95 act ttc ggc gga ggg acc aag gtg gag atc aaa                          321
Thr Phe Gly Gly Gly Thr Lys Val Glu Ile Lys
            100                 105

<210> SEQ ID NO 2
<211> LENGTH: 107
<212> TYPE: PRT
<213> ORGANISM: Macaca fascicularis

<400> SEQUENCE: 2

Glu Leu Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Arg Ser Tyr
            20                  25                  30

Leu Ala Trp Tyr Gln Gln Lys Pro Gly Lys Ala Pro Lys Leu Leu Ile
        35                  40                  45

Tyr Asp Ala Ala His Leu Gln Ser Gly Val Pro Ser Arg Phe Ser Gly
    50                  55                  60

Ser Gly Ser Gly Thr Glu Phe Ser Leu Thr Ile Ser Ser Leu Gln Pro
65                  70                  75                  80

Glu Asp Phe Ala Val Tyr Tyr Cys Gln Gln Arg Asn Ser Tyr Pro Leu
                85                  90                  95

Thr Phe Gly Gly Gly Thr Lys Val Glu Ile Lys
            100                 105

<210> SEQ ID NO 3
<211> LENGTH: 360
<212> TYPE: DNA
<213> ORGANISM: Macaca fascicularis
<220> FEATURE:
<221> NAME/KEY: CDS
<222> LOCATION: (1)..(360)

<400> SEQUENCE: 3 cag gtg cag ctg gtg gag tcg ggg ggc ggc ttg gta aag cct ggg ggg       48
Gln Val Gln Leu Val Glu Ser Gly Gly Gly Leu Val Lys Pro Gly Gly
1               5                   10                  15 tcc ctg aga ctc tcc tgc gca gcc tcc gga ttc acc ttc act gac tac       96
Ser Leu Arg Leu Ser Cys Ala Ala Ser Gly Phe Thr Phe Thr Asp Tyr
            20                  25                  30 tac atg gac tgg gtc cgc cag gct cca ggg aag ggg ctg gag tgg gtc      144
Tyr Met Asp Trp Val Arg Gln Ala Pro Gly Lys Gly Leu Glu Trp Val
        35                  40                  45 tca cgt att agc cct ggt ggt gat gtc aca tgg tac gca gac tcc gtg      192
Ser Arg Ile Ser Pro Gly Gly Asp Val Thr Trp Tyr Ala Asp Ser Val
    50                  55                  60 aag ggc aga ttt acc atc tcc aga gac aac gcc cag aac aca ctg tat      240
Lys Gly Arg Phe Thr Ile Ser Arg Asp Asn Ala Gln Asn Thr Leu Tyr
65                  70                  75                  80 ctt caa atg aac agc ctg aga gct gag gac acg gct gtc tat ttc tgt      288
Leu Gln Met Asn Ser Leu Arg Ala Glu Asp Thr Ala Val Tyr Phe Cys
                85                  90                  95 gcg aga gat gat ata gtg gtg tcc aga att ttt gat gac tgg ggc cag      336
Ala Arg Asp Asp Ile Val Val Ser Arg Ile Phe Asp Asp Trp Gly Gln
            100                 105                 110
```

```
gga gtc ctg gtc acc gtc tcc tca                                          360
Gly Val Leu Val Thr Val Ser Ser
        115                 120

<210> SEQ ID NO 4
<211> LENGTH: 120
<212> TYPE: PRT
<213> ORGANISM: Macaca fascicularis

<400> SEQUENCE: 4

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Thr Asp Tyr
            20                  25                  30

Tyr Met Asp Trp Val Arg Gln Ala Pro Gly Lys Gly Leu Glu Trp Val
        35                  40                  45

Ser Arg Ile Ser Pro Gly Gly Asp Val Thr Trp Tyr Ala Asp Ser Val
    50                  55                  60

Lys Gly Arg Phe Thr Ile Ser Arg Asp Asn Ala Gln Asn Thr Leu Tyr
65                  70                  75                  80

Leu Gln Met Asn Ser Leu Arg Ala Glu Asp Thr Ala Val Tyr Phe Cys
                85                  90                  95

Ala Arg Asp Asp Ile Val Val Ser Arg Ile Phe Asp Trp Gly Gln
            100                 105                 110

Gly Val Leu Val Thr Val Ser Ser
        115                 120

<210> SEQ ID NO 5
<211> LENGTH: 642
<212> TYPE: DNA
<213> ORGANISM: Artificial sequence
<220> FEATURE:
<223> OTHER INFORMATION: Hybride homme/macaque
<220> FEATURE:
<221> NAME/KEY: CDS
<222> LOCATION: (1)..(642)

<400> SEQUENCE: 5 gag ctc cag atg aca cag tct cca tcc tcc ctg tct gca tct gta gga    48
Glu Leu Gln Met Thr Gln Ser Pro Ser Ser Leu Ser Ala Ser Val Gly
1               5                   10                  15 gac aga gtc acc atc act tgt cgg gca agt cag agc att aga agt tat    96
Asp Arg Val Thr Ile Thr Cys Arg Ala Ser Gln Ser Ile Arg Ser Tyr
            20                  25                  30 tta gcc tgg tat cag cag aaa cca ggg aaa gcc cct aag ctc ctg atc    144
Leu Ala Trp Tyr Gln Gln Lys Pro Gly Lys Ala Pro Lys Leu Leu Ile
        35                  40                  45 tat gat gca gcc cat ttg caa agt ggg gtc cca tca agg ttc agc ggc    192
Tyr Asp Ala Ala His Leu Gln Ser Gly Val Pro Ser Arg Phe Ser Gly
    50                  55                  60 agt gga tct ggg aca gaa ttc agt ctc acc atc agc agc ctg caa cct    240
Ser Gly Ser Gly Thr Glu Phe Ser Leu Thr Ile Ser Ser Leu Gln Pro
65                  70                  75                  80 gaa gat ttt gca gtt tat tac tgt caa cag cgt aat agt tat cct ctg    288
Glu Asp Phe Ala Val Tyr Tyr Cys Gln Gln Arg Asn Ser Tyr Pro Leu
                85                  90                  95 act ttc ggc gga ggg acc aag gtg gag atc aaa cga act gtg gct gca    336
Thr Phe Gly Gly Gly Thr Lys Val Glu Ile Lys Arg Thr Val Ala Ala
            100                 105                 110 cca agt gtc ttc atc ttc ccg cca tct gat gag cag ttg aaa tct gga    384
Pro Ser Val Phe Ile Phe Pro Pro Ser Asp Glu Gln Leu Lys Ser Gly
```

```
                   115                 120                 125
act gcc tct gtt gtg tgc ctg ctg aat aac ttc tat ccc aga gag gcc        432
Thr Ala Ser Val Val Cys Leu Leu Asn Asn Phe Tyr Pro Arg Glu Ala
    130                 135                 140 aaa gta cag tgg aag gtg gat aac gcc ctc caa tcg ggt aac tcc cag        480
Lys Val Gln Trp Lys Val Asp Asn Ala Leu Gln Ser Gly Asn Ser Gln
145                 150                 155                 160 gag agt gtc aca gag cag gac agc aag gac agc acc tac agc ctc agc        528
Glu Ser Val Thr Glu Gln Asp Ser Lys Asp Ser Thr Tyr Ser Leu Ser
                165                 170                 175 agc acc ctg acg ctg agc aaa gca gac tac gag aaa cac aaa gtc tac        576
Ser Thr Leu Thr Leu Ser Lys Ala Asp Tyr Glu Lys His Lys Val Tyr
            180                 185                 190 gcc tgc gaa gtc acc cat cag ggc ctg agc tcg ccc gtc aca aag agc        624
Ala Cys Glu Val Thr His Gln Gly Leu Ser Ser Pro Val Thr Lys Ser
        195                 200                 205 ttc aac agg gga gag tgt                                                642
Phe Asn Arg Gly Glu Cys
    210

<210> SEQ ID NO 6
<211> LENGTH: 214
<212> TYPE: PRT
<213> ORGANISM: Artificial sequence
<220> FEATURE:
<223> OTHER INFORMATION: Synthetic Construct

<400> SEQUENCE: 6

Glu Leu Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Arg Ser Tyr
            20                  25                  30

Leu Ala Trp Tyr Gln Gln Lys Pro Gly Lys Ala Pro Lys Leu Leu Ile
        35                  40                  45

Tyr Asp Ala Ala His Leu Gln Ser Gly Val Pro Ser Arg Phe Ser Gly
    50                  55                  60

Ser Gly Ser Gly Thr Glu Phe Ser Leu Thr Ile Ser Ser Leu Gln Pro
65                  70                  75                  80

Glu Asp Phe Ala Val Tyr Tyr Cys Gln Gln Arg Asn Ser Tyr Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 7
```

<211> LENGTH: 1350
<212> TYPE: DNA
<213> ORGANISM: Artificial sequence
<220> FEATURE:
<223> OTHER INFORMATION: Hybride homme/macaque
<220> FEATURE:
<221> NAME/KEY: CDS
<222> LOCATION: (1)..(1350)

<400> SEQUENCE: 7

| | | | | | | | | | | | | | | | | |
|---|---|---|---|---|---|---|---|---|---|---|---|---|---|---|---|---|
| cag | gtg | cag | ctg | gtg | gag | tcg | ggg | ggc | ggc | ttg | gta | aag | cct | ggg | ggg | 48 |
| Gln | Val | Gln | Leu | Val | Glu | Ser | Gly | Gly | Gly | Leu | Val | Lys | Pro | Gly | Gly | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| tcc | ctg | aga | ctc | tcc | tgc | gca | gcc | tcc | gga | ttc | acc | ttc | act | gac | tac | 96 |
| Ser | Leu | Arg | Leu | Ser | Cys | Ala | Ala | Ser | Gly | Phe | Thr | Phe | Thr | Asp | Tyr | |
| | | 20 | | | | | 25 | | | | | 30 | | | | |

| | | | | | | | | | | | | | | | | |
|---|---|---|---|---|---|---|---|---|---|---|---|---|---|---|---|---|
| tac | atg | gac | tgg | gtc | cgc | cag | gct | cca | ggg | aag | ggg | ctg | gag | tgg | gtc | 144 |
| Tyr | Met | Asp | Trp | Val | Arg | Gln | Ala | Pro | Gly | Lys | Gly | Leu | Glu | Trp | Val | |
| | 35 | | | | | 40 | | | | | 45 | | | | | |

| | | | | | | | | | | | | | | | | |
|---|---|---|---|---|---|---|---|---|---|---|---|---|---|---|---|---|
| tca | cgt | att | agc | cct | ggt | ggt | gat | gtc | aca | tgg | tac | gca | gac | tcc | gtg | 192 |
| Ser | Arg | Ile | Ser | Pro | Gly | Gly | Asp | Val | Thr | Trp | Tyr | Ala | Asp | Ser | Val | |
| 50 | | | | | 55 | | | | | 60 | | | | | | |

| | | | | | | | | | | | | | | | | |
|---|---|---|---|---|---|---|---|---|---|---|---|---|---|---|---|---|
| aag | ggc | aga | ttt | acc | atc | tcc | aga | gac | aac | gcc | cag | aac | aca | ctg | tat | 240 |
| Lys | Gly | Arg | Phe | Thr | Ile | Ser | Arg | Asp | Asn | Ala | Gln | Asn | Thr | Leu | Tyr | |
| 65 | | | | 70 | | | | | 75 | | | | | 80 | | |

| | | | | | | | | | | | | | | | | |
|---|---|---|---|---|---|---|---|---|---|---|---|---|---|---|---|---|
| ctt | caa | atg | aac | agc | ctg | aga | gct | gag | gac | acg | gct | gtc | tat | ttc | tgt | 288 |
| Leu | Gln | Met | Asn | Ser | Leu | Arg | Ala | Glu | Asp | Thr | Ala | Val | Tyr | Phe | Cys | |
| | | | | 85 | | | | | 90 | | | | | 95 | | |

| | | | | | | | | | | | | | | | | |
|---|---|---|---|---|---|---|---|---|---|---|---|---|---|---|---|---|
| gcg | aga | gat | gat | ata | gtg | gtg | tcc | aga | att | ttt | gat | gac | tgg | ggc | cag | 336 |
| Ala | Arg | Asp | Asp | Ile | Val | Val | Ser | Arg | Ile | Phe | Asp | Asp | Trp | Gly | Gln | |
| | | | 100 | | | | | 105 | | | | | 110 | | | |

| | | | | | | | | | | | | | | | | |
|---|---|---|---|---|---|---|---|---|---|---|---|---|---|---|---|---|
| gga | gtc | ctg | gtc | acc | gtc | tcc | tca | gcc | tcc | acc | aag | ggc | cca | tcg | gtc | 384 |
| Gly | Val | Leu | Val | Thr | Val | Ser | Ser | Ala | Ser | Thr | Lys | Gly | Pro | Ser | Val | |
| | | 115 | | | | | 120 | | | | | 125 | | | | |

| | | | | | | | | | | | | | | | | |
|---|---|---|---|---|---|---|---|---|---|---|---|---|---|---|---|---|
| ttc | ccc | ctg | gca | ccc | tcc | tcc | aag | agc | acc | tct | ggg | ggc | aca | gcg | gcc | 432 |
| Phe | Pro | Leu | Ala | Pro | Ser | Ser | Lys | Ser | Thr | Ser | Gly | Gly | Thr | Ala | Ala | |
| | 130 | | | | | 135 | | | | | 140 | | | | | |

| | | | | | | | | | | | | | | | | |
|---|---|---|---|---|---|---|---|---|---|---|---|---|---|---|---|---|
| ctg | ggc | tgc | ctg | gtc | aag | gac | tac | ttc | ccc | gaa | ccg | gtg | acg | gtg | tcg | 480 |
| Leu | Gly | Cys | Leu | Val | Lys | Asp | Tyr | Phe | Pro | Glu | Pro | Val | Thr | Val | Ser | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| tgg | aac | tca | ggc | gcc | ctg | acc | agc | ggc | gtg | cac | acc | ttc | ccg | gct | gtc | 528 |
| Trp | Asn | Ser | Gly | Ala | Leu | Thr | Ser | Gly | Val | His | Thr | Phe | Pro | Ala | Val | |
| | | | | 165 | | | | | 170 | | | | | 175 | | |

| | | | | | | | | | | | | | | | | |
|---|---|---|---|---|---|---|---|---|---|---|---|---|---|---|---|---|
| cta | cag | tcc | tca | gga | ctc | tac | tcc | ctc | agc | agc | gtg | gtg | acc | gtg | ccc | 576 |
| Leu | Gln | Ser | Ser | Gly | Leu | Tyr | Ser | Leu | Ser | Ser | Val | Val | Thr | Val | Pro | |
| | | | 180 | | | | | 185 | | | | | 190 | | | |

| | | | | | | | | | | | | | | | | |
|---|---|---|---|---|---|---|---|---|---|---|---|---|---|---|---|---|
| tcc | agc | agc | ttg | ggc | acc | cag | acc | tac | atc | tgc | aac | gtg | aat | cac | aag | 624 |
| Ser | Ser | Ser | Leu | Gly | Thr | Gln | Thr | Tyr | Ile | Cys | Asn | Val | Asn | His | Lys | |
| | | 195 | | | | | 200 | | | | | 205 | | | | |

| | | | | | | | | | | | | | | | | |
|---|---|---|---|---|---|---|---|---|---|---|---|---|---|---|---|---|
| ccc | agc | aac | acc | aag | gtg | gac | aag | aaa | gtt | gag | ccc | aaa | tct | tgt | gac | 672 |
| Pro | Ser | Asn | Thr | Lys | Val | Asp | Lys | Lys | Val | Glu | Pro | Lys | Ser | Cys | Asp | |
| | 210 | | | | | 215 | | | | | 220 | | | | | |

| | | | | | | | | | | | | | | | | |
|---|---|---|---|---|---|---|---|---|---|---|---|---|---|---|---|---|
| aaa | act | cac | aca | tgc | cca | ccg | tgc | cca | gca | cct | gaa | ctc | ctg | ggg | gga | 720 |
| Lys | Thr | His | Thr | Cys | Pro | Pro | Cys | Pro | Ala | Pro | Glu | Leu | Leu | Gly | Gly | |
| 225 | | | | | 230 | | | | | 235 | | | | | 240 | |

| | | | | | | | | | | | | | | | | |
|---|---|---|---|---|---|---|---|---|---|---|---|---|---|---|---|---|
| ccg | tca | gtc | ttc | ctc | ttc | ccc | cca | aaa | ccc | aag | gac | acc | ctc | atg | atc | 768 |
| Pro | Ser | Val | Phe | Leu | Phe | Pro | Pro | Lys | Pro | Lys | Asp | Thr | Leu | Met | Ile | |
| | | | | 245 | | | | | 250 | | | | | 255 | | |

| | | | | | | | | | | | | | | | | |
|---|---|---|---|---|---|---|---|---|---|---|---|---|---|---|---|---|
| tcc | cgg | acc | cct | gag | gtc | aca | tgc | gtg | gtg | gtg | gac | gtg | agc | cac | gaa | 816 |
| Ser | Arg | Thr | Pro | Glu | Val | Thr | Cys | Val | Val | Val | Asp | Val | Ser | His | Glu | |
| | | | 260 | | | | | 265 | | | | | 270 | | | |

| | | | | | | | | | | | | | | | | |
|---|---|---|---|---|---|---|---|---|---|---|---|---|---|---|---|---|
| gac | cct | gag | gtc | aag | ttc | aac | tgg | tac | gtg | gac | ggc | gtg | gag | gtg | cat | 864 |

```
                  Asp Pro Glu Val Lys Phe Asn Trp Tyr Val Asp Gly Val Glu Val His
                          275                 280                 285 aat gcc aag aca aag ccg cgg gag gag cag tac aac agc acg tac cgt       912
Asn Ala Lys Thr Lys Pro Arg Glu Glu Gln Tyr Asn Ser Thr Tyr Arg
        290                 295                 300 gtg gtc agc gtc ctc acc gtc ctg cac cag gac tgg ctg aat ggc aag       960
Val Val Ser Val Leu Thr Val Leu His Gln Asp Trp Leu Asn Gly Lys
305                 310                 315                 320 gag tac aag tgc aag gtc tcc aac aaa gcc ctc cca gcc ccc atc gag      1008
Glu Tyr Lys Cys Lys Val Ser Asn Lys Ala Leu Pro Ala Pro Ile Glu
                325                 330                 335 aaa acc atc tcc aaa gcc aaa ggg cag ccc cga gaa cca cag gtg tac      1056
Lys Thr Ile Ser Lys Ala Lys Gly Gln Pro Arg Glu Pro Gln Val Tyr
                340                 345                 350 acc ctg ccc cca tcc cgg gat gag ctg acc aag aac cag gtc agc ctg      1104
Thr Leu Pro Pro Ser Arg Asp Glu Leu Thr Lys Asn Gln Val Ser Leu
                355                 360                 365 acc tgc ctg gtc aaa ggc ttc tat ccc agc gac atc gcc gtg gag tgg      1152
Thr Cys Leu Val Lys Gly Phe Tyr Pro Ser Asp Ile Ala Val Glu Trp
370                 375                 380 gag agc aat ggg cag ccg gag aac aac tac aag acc acg cct ccc gtg      1200
Glu Ser Asn Gly Gln Pro Glu Asn Asn Tyr Lys Thr Thr Pro Pro Val
385                 390                 395                 400 ctg gac tcc gac ggc tcc ttc ttc ctc tac agc aag ctc acc gtg gac      1248
Leu Asp Ser Asp Gly Ser Phe Phe Leu Tyr Ser Lys Leu Thr Val Asp
                405                 410                 415 aag agc agg tgg cag cag ggg aac gtc ttc tca tgc tcc gtg atg cat      1296
Lys Ser Arg Trp Gln Gln Gly Asn Val Phe Ser Cys Ser Val Met His
                420                 425                 430 gag gct ctg cac aac cac tac acg cag aag agc ctc tcc ctg tct ccg      1344
Glu Ala Leu His Asn His Tyr Thr Gln Lys Ser Leu Ser Leu Ser Pro
                435                 440                 445 ggt aaa                                                               1350
Gly Lys
    450

<210> SEQ ID NO 8
<211> LENGTH: 450
<212> TYPE: PRT
<213> ORGANISM: Artificial sequence
<220> FEATURE:
<223> OTHER INFORMATION: Synthetic Construct

<400> SEQUENCE: 8

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Thr Asp Tyr
            20                  25                  30

Tyr Met Asp Trp Val Arg Gln Ala Pro Gly Lys Gly Leu Glu Trp Val
        35                  40                  45

Ser Arg Ile Ser Pro Gly Gly Asp Val Thr Trp Tyr Ala Asp Ser Val
    50                  55                  60

Lys Gly Arg Phe Thr Ile Ser Arg Asp Asn Ala Gln Asn Thr Leu Tyr
65                  70                  75                  80

Leu Gln Met Asn Ser Leu Arg Ala Glu Asp Thr Ala Val Tyr Phe Cys
                85                  90                  95

Ala Arg Asp Asp Ile Val Val Ser Arg Ile Phe Asp Asp Trp Gly Gln
            100                 105                 110

Gly Val Leu Val Thr Val Ser Ser Ala Ser Thr Lys Gly Pro Ser Val
        115                 120                 125
```

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 9
<211> LENGTH: 387
<212> TYPE: DNA
<213> ORGANISM: Macaca fascicularis
<220> FEATURE:
<221> NAME/KEY: CDS
<222> LOCATION: (1)..(387)

<400> SEQUENCE: 9 atg gac atg agg gtc ccc gct cag ctc ctg ggg ctt ctg ctg ctc tgg      48
Met Asp Met Arg Val Pro Ala Gln Leu Leu Gly Leu Leu Leu Leu Trp
1               5                   10                  15 ctc cca ggt gcc aga tgt gag ctc cag atg aca cag tct cca tcc tcc      96

```
Leu Pro Gly Ala Arg Cys Glu Leu Gln Met Thr Gln Ser Pro Ser Ser
            20                  25                  30 ctg tct gca tct gta gga gac aga gtc acc atc act tgt cgg gca agt    144
Leu Ser Ala Ser Val Gly Asp Arg Val Thr Ile Thr Cys Arg Ala Ser
        35                  40                  45 cag agc att aga agt tat tta gcc tgg tat cag cag aaa cca ggg aaa    192
Gln Ser Ile Arg Ser Tyr Leu Ala Trp Tyr Gln Gln Lys Pro Gly Lys
    50                  55                  60 gcc cct aag ctc ctg atc tat gat gca gcc cat ttg caa agt ggg gtc    240
Ala Pro Lys Leu Leu Ile Tyr Asp Ala Ala His Leu Gln Ser Gly Val
65                  70                  75                  80 cca tca agg ttc agc ggc agt gga tct ggg aca gaa ttc agt ctc acc    288
Pro Ser Arg Phe Ser Gly Ser Gly Ser Gly Thr Glu Phe Ser Leu Thr
                85                  90                  95 atc agc agc ctg caa cct gaa gat ttt gca gtt tat tac tgt caa cag    336
Ile Ser Ser Leu Gln Pro Glu Asp Phe Ala Val Tyr Tyr Cys Gln Gln
            100                 105                 110 cgt aat agt tat cct ctg act ttc ggc gga ggg acc aag gtg gag atc    384
Arg Asn Ser Tyr Pro Leu Thr Phe Gly Gly Gly Thr Lys Val Glu Ile
        115                 120                 125 aaa                                                                 387
Lys

<210> SEQ ID NO 10
<211> LENGTH: 129
<212> TYPE: PRT
<213> ORGANISM: Macaca fascicularis

<400> SEQUENCE: 10

Met Asp Met Arg Val Pro Ala Gln Leu Leu Gly Leu Leu Leu Leu Trp
1               5                   10                  15

Leu Pro Gly Ala Arg Cys Glu Leu Gln Met Thr Gln Ser Pro Ser Ser
            20                  25                  30

Leu Ser Ala Ser Val Gly Asp Arg Val Thr Ile Thr Cys Arg Ala Ser
        35                  40                  45

Gln Ser Ile Arg Ser Tyr Leu Ala Trp Tyr Gln Gln Lys Pro Gly Lys
    50                  55                  60

Ala Pro Lys Leu Leu Ile Tyr Asp Ala Ala His Leu Gln Ser Gly Val
65                  70                  75                  80

Pro Ser Arg Phe Ser Gly Ser Gly Ser Gly Thr Glu Phe Ser Leu Thr
                85                  90                  95

Ile Ser Ser Leu Gln Pro Glu Asp Phe Ala Val Tyr Tyr Cys Gln Gln
            100                 105                 110

Arg Asn Ser Tyr Pro Leu Thr Phe Gly Gly Gly Thr Lys Val Glu Ile
        115                 120                 125

Lys

<210> SEQ ID NO 11
<211> LENGTH: 417
<212> TYPE: DNA
<213> ORGANISM: Macaca fascicularis
<220> FEATURE:
<221> NAME/KEY: CDS
<222> LOCATION: (1)..(417)

<400> SEQUENCE: 11 atg aaa cat ctg tgg ttc ttc ctt ctc ctg gtg gca gct ccc aga tgg    48
Met Lys His Leu Trp Phe Phe Leu Leu Leu Val Ala Ala Pro Arg Trp
1               5                   10                  15 gtc ctg tcc cag gtg cag ctg gtg gag tcg ggg ggc ggc ttg gta aag    96
```

```
                Val Leu Ser Gln Val Gln Leu Val Glu Ser Gly Gly Leu Val Lys
                         20                  25                  30 cct ggg ggg tcc ctg aga ctc tcc tgc gca gcc tcc gga ttc acc ttc         144
Pro Gly Gly Ser Leu Arg Leu Ser Cys Ala Ala Ser Gly Phe Thr Phe
         35                  40                  45 act gac tac tac atg gac tgg gtc cgc cag gct cca ggg aag ggg ctg         192
Thr Asp Tyr Tyr Met Asp Trp Val Arg Gln Ala Pro Gly Lys Gly Leu
 50                  55                  60 gag tgg gtc tca cgt att agc cct ggt ggt gat gtc aca tgg tac gca         240
Glu Trp Val Ser Arg Ile Ser Pro Gly Gly Asp Val Thr Trp Tyr Ala
 65                  70                  75                  80 gac tcc gtg aag ggc aga ttt acc atc tcc aga gac aac gcc cag aac         288
Asp Ser Val Lys Gly Arg Phe Thr Ile Ser Arg Asp Asn Ala Gln Asn
                 85                  90                  95 aca ctg tat ctt caa atg aac agc ctg aga gct gag gac acg gct gtc         336
Thr Leu Tyr Leu Gln Met Asn Ser Leu Arg Ala Glu Asp Thr Ala Val
                100                 105                 110 tat ttc tgt gcg aga gat gat ata gtg gtg tcc aga att ttt gat gac         384
Tyr Phe Cys Ala Arg Asp Asp Ile Val Val Ser Arg Ile Phe Asp Asp
            115                 120                 125 tgg ggc cag gga gtc ctg gtc acc gtc tcc tca                             417
Trp Gly Gln Gly Val Leu Val Thr Val Ser Ser
130                 135
```

<210> SEQ ID NO 12
<211> LENGTH: 139
<212> TYPE: PRT
<213> ORGANISM: Macaca fascicularis

<400> SEQUENCE: 12

```
Met Lys His Leu Trp Phe Phe Leu Leu Leu Val Ala Ala Pro Arg Trp
 1               5                  10                  15

Val Leu Ser Gln Val Gln Leu Val Glu Ser Gly Gly Gly Leu Val Lys
                 20                  25                  30

Pro Gly Gly Ser Leu Arg Leu Ser Cys Ala Ala Ser Gly Phe Thr Phe
         35                  40                  45

Thr Asp Tyr Tyr Met Asp Trp Val Arg Gln Ala Pro Gly Lys Gly Leu
 50                  55                  60

Glu Trp Val Ser Arg Ile Ser Pro Gly Gly Asp Val Thr Trp Tyr Ala
 65                  70                  75                  80

Asp Ser Val Lys Gly Arg Phe Thr Ile Ser Arg Asp Asn Ala Gln Asn
                 85                  90                  95

Thr Leu Tyr Leu Gln Met Asn Ser Leu Arg Ala Glu Asp Thr Ala Val
                100                 105                 110

Tyr Phe Cys Ala Arg Asp Asp Ile Val Val Ser Arg Ile Phe Asp Asp
            115                 120                 125

Trp Gly Gln Gly Val Leu Val Thr Val Ser Ser
130                 135
```

<210> SEQ ID NO 13
<211> LENGTH: 708
<212> TYPE: DNA
<213> ORGANISM: Artificial sequence
<220> FEATURE:
<223> OTHER INFORMATION: Hybride homme/macaque
<220> FEATURE:
<221> NAME/KEY: CDS
<222> LOCATION: (1)..(708)

<400> SEQUENCE: 13

```
atg gac atg agg gtc ccc gct cag ctc ctg ggg ctt ctg ctg ctc tgg         48
```

```
Met Asp Met Arg Val Pro Ala Gln Leu Leu Gly Leu Leu Leu Leu Trp
1               5                   10                  15 ctc cca ggt gcc aga tgt gag ctc cag atg aca cag tct cca tcc tcc      96
Leu Pro Gly Ala Arg Cys Glu Leu Gln Met Thr Gln Ser Pro Ser Ser
            20                  25                  30 ctg tct gca tct gta gga gac aga gtc acc atc act tgt cgg gca agt     144
Leu Ser Ala Ser Val Gly Asp Arg Val Thr Ile Thr Cys Arg Ala Ser
                35                  40                  45 cag agc att aga agt tat tta gcc tgg tat cag cag aaa cca ggg aaa     192
Gln Ser Ile Arg Ser Tyr Leu Ala Trp Tyr Gln Gln Lys Pro Gly Lys
        50                  55                  60 gcc cct aag ctc ctg atc tat gat gca gcc cat ttg caa agt ggg gtc     240
Ala Pro Lys Leu Leu Ile Tyr Asp Ala Ala His Leu Gln Ser Gly Val
65                  70                  75                  80 cca tca agg ttc agc ggc agt gga tct ggg aca gaa ttc agt ctc acc     288
Pro Ser Arg Phe Ser Gly Ser Gly Ser Gly Thr Glu Phe Ser Leu Thr
                85                  90                  95 atc agc agc ctg caa cct gaa gat ttt gca gtt tat tac tgt caa cag     336
Ile Ser Ser Leu Gln Pro Glu Asp Phe Ala Val Tyr Tyr Cys Gln Gln
            100                 105                 110 cgt aat agt tat cct ctg act ttc ggc gga ggg acc aag gtg gag atc     384
Arg Asn Ser Tyr Pro Leu Thr Phe Gly Gly Gly Thr Lys Val Glu Ile
        115                 120                 125 aaa cga act gtg gct gca cca agt gtc ttc atc ttc ccg cca tct gat     432
Lys Arg Thr Val Ala Ala Pro Ser Val Phe Ile Phe Pro Pro Ser Asp
    130                 135                 140 gag cag ttg aaa tct gga act gcc tct gtt gtg tgc ctg ctg aat aac     480
Glu Gln Leu Lys Ser Gly Thr Ala Ser Val Val Cys Leu Leu Asn Asn
145                 150                 155                 160 ttc tat ccc aga gag gcc aaa gta cag tgg aag gtg gat aac gcc ctc     528
Phe Tyr Pro Arg Glu Ala Lys Val Gln Trp Lys Val Asp Asn Ala Leu
                165                 170                 175 caa tcg ggt aac tcc cag gag agt gtc aca gag cag gac agc aag gac     576
Gln Ser Gly Asn Ser Gln Glu Ser Val Thr Glu Gln Asp Ser Lys Asp
            180                 185                 190 agc acc tac agc ctc agc agc acc ctg acg ctg agc aaa gca gac tac     624
Ser Thr Tyr Ser Leu Ser Ser Thr Leu Thr Leu Ser Lys Ala Asp Tyr
        195                 200                 205 gag aaa cac aaa gtc tac gcc tgc gaa gtc acc cat cag ggc ctg agc     672
Glu Lys His Lys Val Tyr Ala Cys Glu Val Thr His Gln Gly Leu Ser
    210                 215                 220 tcg ccc gtc aca aag agc ttc aac agg gga gag tgt                     708
Ser Pro Val Thr Lys Ser Phe Asn Arg Gly Glu Cys
225                 230                 235
```

<210> SEQ ID NO 14
<211> LENGTH: 236
<212> TYPE: PRT
<213> ORGANISM: Artificial sequence
<220> FEATURE:
<223> OTHER INFORMATION: Synthetic Construct

<400> SEQUENCE: 14

```
Met Asp Met Arg Val Pro Ala Gln Leu Leu Gly Leu Leu Leu Leu Trp
1               5                   10                  15

Leu Pro Gly Ala Arg Cys Glu Leu Gln Met Thr Gln Ser Pro Ser Ser
            20                  25                  30

Leu Ser Ala Ser Val Gly Asp Arg Val Thr Ile Thr Cys Arg Ala Ser
                35                  40                  45

Gln Ser Ile Arg Ser Tyr Leu Ala Trp Tyr Gln Gln Lys Pro Gly Lys
        50                  55                  60
```

```
Ala Pro Lys Leu Leu Ile Tyr Asp Ala Ala His Leu Gln Ser Gly Val
 65                  70                  75                  80

Pro Ser Arg Phe Ser Gly Ser Gly Ser Gly Thr Glu Phe Ser Leu Thr
                 85                  90                  95

Ile Ser Ser Leu Gln Pro Glu Asp Phe Ala Val Tyr Tyr Cys Gln Gln
            100                 105                 110

Arg Asn Ser Tyr Pro Leu Thr Phe Gly Gly Gly Thr Lys Val Glu Ile
            115                 120                 125

Lys Arg Thr Val Ala Ala Pro Ser Val Phe Ile Phe Pro Pro Ser Asp
130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
            195                 200                 205

Glu Lys His Lys Val Tyr Ala Cys Glu Val Thr His Gln Gly Leu Ser
210                 215                 220

Ser Pro Val Thr Lys Ser Phe Asn Arg Gly Glu Cys
225                 230                 235

<210> SEQ ID NO 15
<211> LENGTH: 1407
<212> TYPE: DNA
<213> ORGANISM: Artificial sequence
<220> FEATURE:
<223> OTHER INFORMATION: Hybride homme/macaque
<220> FEATURE:
<221> NAME/KEY: CDS
<222> LOCATION: (1)..(1407)

<400> SEQUENCE: 15 atg aaa cat ctg tgg ttc ttc ctt ctc ctg gtg gca gct ccc aga tgg      48
Met Lys His Leu Trp Phe Phe Leu Leu Leu Val Ala Ala Pro Arg Trp
  1               5                  10                  15 gtc ctg tcc cag gtg cag ctg gtg gag tcg ggg ggc ggc ttg gta aag      96
Val Leu Ser Gln Val Gln Leu Val Glu Ser Gly Gly Gly Leu Val Lys
             20                  25                  30 cct ggg ggg tcc ctg aga ctc tcc tgc gca gcc tcc gga ttc acc ttc     144
Pro Gly Gly Ser Leu Arg Leu Ser Cys Ala Ala Ser Gly Phe Thr Phe
         35                  40                  45 act gac tac tac atg gac tgg gtc cgc cag gct cca ggg aag ggg ctg     192
Thr Asp Tyr Tyr Met Asp Trp Val Arg Gln Ala Pro Gly Lys Gly Leu
     50                  55                  60 gag tgg gtc tca cgt att agc cct ggt ggt gat gtc aca tgg tac gca     240
Glu Trp Val Ser Arg Ile Ser Pro Gly Gly Asp Val Thr Trp Tyr Ala
 65                  70                  75                  80 gac tcc gtg aag ggc aga ttt acc atc tcc aga gac aac gcc cag aac     288
Asp Ser Val Lys Gly Arg Phe Thr Ile Ser Arg Asp Asn Ala Gln Asn
                 85                  90                  95 aca ctg tat ctt caa atg aac agc ctg aga gct gag gac acg gct gtc     336
Thr Leu Tyr Leu Gln Met Asn Ser Leu Arg Ala Glu Asp Thr Ala Val
            100                 105                 110 tat ttc tgt gcg aga gat gat ata gtg gtg tcc aga att ttt gat gac     384
Tyr Phe Cys Ala Arg Asp Asp Ile Val Val Ser Arg Ile Phe Asp Asp
            115                 120                 125 tgg ggc cag gga gtc ctg gtc acc gtc tcc tca gcc tcc acc aag ggc     432
```

|   |   |   |   |   |   |   |   |   |   |   |   |   |   |   |
|---|---|---|---|---|---|---|---|---|---|---|---|---|---|---|
| Trp | Gly | Gln | Gly | Val | Leu | Val | Thr | Val | Ser | Ser | Ala | Ser | Thr | Lys | Gly |
|   |   | 130 |   |   |   | 135 |   |   |   | 140 |   |   |   |   |

| cca | tcg | gtc | ttc | ccc | ctg | gca | ccc | tcc | tcc | aag | agc | acc | tct | ggg | ggc | 480 |
|---|---|---|---|---|---|---|---|---|---|---|---|---|---|---|---|---|
| Pro | Ser | Val | Phe | Pro | Leu | Ala | Pro | Ser | Ser | Lys | Ser | Thr | Ser | Gly | Gly |   |
| 145 |   |   |   |   | 150 |   |   |   |   | 155 |   |   |   |   | 160 |   |

| aca | gcg | gcc | ctg | ggc | tgc | ctg | gtc | aag | gac | tac | ttc | ccc | gaa | ccg | gtg | 528 |
|---|---|---|---|---|---|---|---|---|---|---|---|---|---|---|---|---|
| Thr | Ala | Ala | Leu | Gly | Cys | Leu | Val | Lys | Asp | Tyr | Phe | Pro | Glu | Pro | Val |   |
|   |   |   |   | 165 |   |   |   |   | 170 |   |   |   |   | 175 |   |   |

| acg | gtg | tcg | tgg | aac | tca | ggc | gcc | ctg | acc | agc | ggc | gtg | cac | acc | ttc | 576 |
|---|---|---|---|---|---|---|---|---|---|---|---|---|---|---|---|---|
| Thr | Val | Ser | Trp | Asn | Ser | Gly | Ala | Leu | Thr | Ser | Gly | Val | His | Thr | Phe |   |
|   |   |   | 180 |   |   |   |   | 185 |   |   |   |   | 190 |   |   |   |

| ccg | gct | gtc | cta | cag | tcc | tca | gga | ctc | tac | tcc | ctc | agc | agc | gtg | gtg | 624 |
|---|---|---|---|---|---|---|---|---|---|---|---|---|---|---|---|---|
| Pro | Ala | Val | Leu | Gln | Ser | Ser | Gly | Leu | Tyr | Ser | Leu | Ser | Ser | Val | Val |   |
|   |   |   | 195 |   |   |   |   | 200 |   |   |   |   | 205 |   |   |   |

| acc | gtg | ccc | tcc | agc | agc | ttg | ggc | acc | cag | acc | tac | atc | tgc | aac | gtg | 672 |
|---|---|---|---|---|---|---|---|---|---|---|---|---|---|---|---|---|
| Thr | Val | Pro | Ser | Ser | Ser | Leu | Gly | Thr | Gln | Thr | Tyr | Ile | Cys | Asn | Val |   |
|   | 210 |   |   |   |   | 215 |   |   |   |   | 220 |   |   |   |   |   |

| aat | cac | aag | ccc | agc | aac | acc | aag | gtg | gac | aag | aaa | gtt | gag | ccc | aaa | 720 |
|---|---|---|---|---|---|---|---|---|---|---|---|---|---|---|---|---|
| Asn | His | Lys | Pro | Ser | Asn | Thr | Lys | Val | Asp | Lys | Lys | Val | Glu | Pro | Lys |   |
| 225 |   |   |   |   | 230 |   |   |   |   | 235 |   |   |   |   | 240 |   |

| tct | tgt | gac | aaa | act | cac | aca | tgc | cca | ccg | tgc | cca | gca | cct | gaa | ctc | 768 |
|---|---|---|---|---|---|---|---|---|---|---|---|---|---|---|---|---|
| Ser | Cys | Asp | Lys | Thr | His | Thr | Cys | Pro | Pro | Cys | Pro | Ala | Pro | Glu | Leu |   |
|   |   |   |   | 245 |   |   |   |   | 250 |   |   |   |   | 255 |   |   |

| ctg | ggg | gga | ccg | tca | gtc | ttc | ctc | ttc | ccc | cca | aaa | ccc | aag | gac | acc | 816 |
|---|---|---|---|---|---|---|---|---|---|---|---|---|---|---|---|---|
| Leu | Gly | Gly | Pro | Ser | Val | Phe | Leu | Phe | Pro | Pro | Lys | Pro | Lys | Asp | Thr |   |
|   |   |   | 260 |   |   |   |   | 265 |   |   |   |   | 270 |   |   |   |

| ctc | atg | atc | tcc | cgg | acc | cct | gag | gtc | aca | tgc | gtg | gtg | gtg | gac | gtg | 864 |
|---|---|---|---|---|---|---|---|---|---|---|---|---|---|---|---|---|
| Leu | Met | Ile | Ser | Arg | Thr | Pro | Glu | Val | Thr | Cys | Val | Val | Val | Asp | Val |   |
|   |   |   | 275 |   |   |   |   | 280 |   |   |   |   | 285 |   |   |   |

| agc | cac | gaa | gac | cct | gag | gtc | aag | ttc | aac | tgg | tac | gtg | gac | ggc | gtg | 912 |
|---|---|---|---|---|---|---|---|---|---|---|---|---|---|---|---|---|
| Ser | His | Glu | Asp | Pro | Glu | Val | Lys | Phe | Asn | Trp | Tyr | Val | Asp | Gly | Val |   |
|   | 290 |   |   |   |   | 295 |   |   |   |   | 300 |   |   |   |   |   |

| gag | gtg | cat | aat | gcc | aag | aca | aag | ccg | cgg | gag | gag | cag | tac | aac | agc | 960 |
|---|---|---|---|---|---|---|---|---|---|---|---|---|---|---|---|---|
| Glu | Val | His | Asn | Ala | Lys | Thr | Lys | Pro | Arg | Glu | Glu | Gln | Tyr | Asn | Ser |   |
| 305 |   |   |   |   | 310 |   |   |   |   | 315 |   |   |   |   | 320 |   |

| acg | tac | cgt | gtg | gtc | agc | gtc | ctc | acc | gtc | ctg | cac | cag | gac | tgg | ctg | 1008 |
|---|---|---|---|---|---|---|---|---|---|---|---|---|---|---|---|---|
| Thr | Tyr | Arg | Val | Val | Ser | Val | Leu | Thr | Val | Leu | His | Gln | Asp | Trp | Leu |   |
|   |   |   |   | 325 |   |   |   |   | 330 |   |   |   |   | 335 |   |   |

| aat | ggc | aag | gag | tac | aag | tgc | aag | gtc | tcc | aac | aaa | gcc | ctc | cca | gcc | 1056 |
|---|---|---|---|---|---|---|---|---|---|---|---|---|---|---|---|---|
| Asn | Gly | Lys | Glu | Tyr | Lys | Cys | Lys | Val | Ser | Asn | Lys | Ala | Leu | Pro | Ala |   |
|   |   |   | 340 |   |   |   |   | 345 |   |   |   |   | 350 |   |   |   |

| ccc | atc | gag | aaa | acc | atc | tcc | aaa | gcc | aaa | ggg | cag | ccc | cga | gaa | cca | 1104 |
|---|---|---|---|---|---|---|---|---|---|---|---|---|---|---|---|---|
| Pro | Ile | Glu | Lys | Thr | Ile | Ser | Lys | Ala | Lys | Gly | Gln | Pro | Arg | Glu | Pro |   |
|   |   | 355 |   |   |   |   | 360 |   |   |   |   | 365 |   |   |   |   |

| cag | gtg | tac | acc | ctg | ccc | cca | tcc | cgg | gat | gag | ctg | acc | aag | aac | cag | 1152 |
|---|---|---|---|---|---|---|---|---|---|---|---|---|---|---|---|---|
| Gln | Val | Tyr | Thr | Leu | Pro | Pro | Ser | Arg | Asp | Glu | Leu | Thr | Lys | Asn | Gln |   |
|   | 370 |   |   |   |   | 375 |   |   |   |   | 380 |   |   |   |   |   |

| gtc | agc | ctg | acc | tgc | ctg | gtc | aaa | ggc | ttc | tat | ccc | agc | gac | atc | gcc | 1200 |
|---|---|---|---|---|---|---|---|---|---|---|---|---|---|---|---|---|
| Val | Ser | Leu | Thr | Cys | Leu | Val | Lys | Gly | Phe | Tyr | Pro | Ser | Asp | Ile | Ala |   |
| 385 |   |   |   |   | 390 |   |   |   |   | 395 |   |   |   |   | 400 |   |

| gtg | gag | tgg | gag | agc | aat | ggg | cag | ccg | gag | aac | aac | tac | aag | acc | acg | 1248 |
|---|---|---|---|---|---|---|---|---|---|---|---|---|---|---|---|---|
| Val | Glu | Trp | Glu | Ser | Asn | Gly | Gln | Pro | Glu | Asn | Asn | Tyr | Lys | Thr | Thr |   |
|   |   |   |   | 405 |   |   |   |   | 410 |   |   |   |   | 415 |   |   |

| cct | ccc | gtg | ctg | gac | tcc | gac | ggc | tcc | ttc | ttc | ctc | tac | agc | aag | ctc | 1296 |
|---|---|---|---|---|---|---|---|---|---|---|---|---|---|---|---|---|
| Pro | Pro | Val | Leu | Asp | Ser | Asp | Gly | Ser | Phe | Phe | Leu | Tyr | Ser | Lys | Leu |   |
|   |   |   | 420 |   |   |   |   | 425 |   |   |   |   | 430 |   |   |   |

| acc | gtg | gac | aag | agc | agg | tgg | cag | cag | ggg | aac | gtc | ttc | tca | tgc | tcc | 1344 |
|---|---|---|---|---|---|---|---|---|---|---|---|---|---|---|---|---|
| Thr | Val | Asp | Lys | Ser | Arg | Trp | Gln | Gln | Gly | Asn | Val | Phe | Ser | Cys | Ser |   |
|   |   | 435 |   |   |   |   | 440 |   |   |   |   | 445 |   |   |   |   |

| gtg | atg | cat | gag | gct | ctg | cac | aac | cac | tac | acg | cag | aag | agc | ctc | tcc | 1392 |
|---|---|---|---|---|---|---|---|---|---|---|---|---|---|---|---|---|

```
Val Met His Glu Ala Leu His Asn His Tyr Thr Gln Lys Ser Leu Ser
        450                 455                 460 ctg tct ccg ggt aaa                                                    1407
Leu Ser Pro Gly Lys
465

<210> SEQ ID NO 16
<211> LENGTH: 469
<212> TYPE: PRT
<213> ORGANISM: Artificial sequence
<220> FEATURE:
<223> OTHER INFORMATION: Synthetic Construct

<400> SEQUENCE: 16

Met Lys His Leu Trp Phe Phe Leu Leu Leu Val Ala Ala Pro Arg Trp
1               5                   10                  15

Val Leu Ser Gln Val Gln Leu Val Glu Ser Gly Gly Gly Leu Val Lys
            20                  25                  30

Pro Gly Gly Ser Leu Arg Leu Ser Cys Ala Ala Ser Gly Phe Thr Phe
        35                  40                  45

Thr Asp Tyr Tyr Met Asp Trp Val Arg Gln Ala Pro Gly Lys Gly Leu
    50                  55                  60

Glu Trp Val Ser Arg Ile Ser Pro Gly Gly Asp Val Thr Trp Tyr Ala
65                  70                  75                  80

Asp Ser Val Lys Gly Arg Phe Thr Ile Ser Arg Asp Asn Ala Gln Asn
                85                  90                  95

Thr Leu Tyr Leu Gln Met Asn Ser Leu Arg Ala Glu Asp Thr Ala Val
            100                 105                 110

Tyr Phe Cys Ala Arg Asp Asp Ile Val Val Ser Arg Ile Phe Asp Asp
        115                 120                 125

Trp Gly Gln Gly Val Leu Val Thr Val Ser Ser Ala Ser Thr Lys Gly
    130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Ser Leu Gly Thr Gln Thr Tyr Ile Cys Asn Val
    210                 215                 220

Asn His Lys Pro Ser Asn Thr Lys Val Asp Lys Lys Val Glu Pro Lys
225                 230                 235                 240

Ser Cys Asp Lys Thr His Thr Cys Pro Pro Cys Pro Ala Pro Glu Leu
                245                 250                 255

Leu Gly Gly Pro Ser Val Phe Leu Phe Pro Pro Lys Pro Lys Asp Thr
            260                 265                 270

Leu Met Ile Ser Arg Thr Pro Glu Val Thr Cys Val Val Val Asp Val
        275                 280                 285

Ser His Glu Asp Pro Glu Val Lys Phe Asn Trp Tyr Val Asp Gly Val
    290                 295                 300

Glu Val His Asn Ala Lys Thr Lys Pro Arg Glu Glu Gln Tyr Asn Ser
305                 310                 315                 320

Thr Tyr Arg Val Val Ser Val Leu Thr Val Leu His Gln Asp Trp Leu
                325                 330                 335
```

```
Asn Gly Lys Glu Tyr Lys Cys Lys Val Ser Asn Lys Ala Leu Pro Ala
            340                 345                 350

Pro Ile Glu Lys Thr Ile Ser Lys Ala Lys Gly Gln Pro Arg Glu Pro
            355                 360                 365

Gln Val Tyr Thr Leu Pro Pro Ser Arg Asp Glu Leu Thr Lys Asn Gln
            370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
            405                 410                 415

Pro Pro Val Leu Asp Ser Asp Gly Ser Phe Phe Leu Tyr Ser Lys Leu
            420                 425                 430

Thr Val Asp Lys Ser Arg Trp Gln Gln Gly Asn Val Phe Ser Cys Ser
            435                 440                 445

Val Met His Glu Ala Leu His Asn His Tyr Thr Gln Lys Ser Leu Ser
            450                 455                 460

Leu Ser Pro Gly Lys
465

<210> SEQ ID NO 17
<211> LENGTH: 57
<212> TYPE: DNA
<213> ORGANISM: Artificial Sequence
<220> FEATURE:
<223> OTHER INFORMATION: sequence leader
<220> FEATURE:
<221> NAME/KEY: CDS
<222> LOCATION: (1)..(57)

<400> SEQUENCE: 17 atg aaa cat ctg tgg ttc ttc ctt ctc ctg gtg gca gct ccc aga tgg    48
Met Lys His Leu Trp Phe Phe Leu Leu Leu Val Ala Ala Pro Arg Trp
1               5                   10                  15 gtc ctg tcc                                                        57
Val Leu Ser <210> SEQ ID NO 18
<211> LENGTH: 19
<212> TYPE: PRT
<213> ORGANISM: Artificial Sequence
<220> FEATURE:
<223> OTHER INFORMATION: Synthetic Construct

<400> SEQUENCE: 18

Met Lys His Leu Trp Phe Phe Leu Leu Leu Val Ala Ala Pro Arg Trp
1               5                   10                  15

Val Leu Ser

<210> SEQ ID NO 19
<211> LENGTH: 66
<212> TYPE: DNA
<213> ORGANISM: Artificial Sequence
<220> FEATURE:
<223> OTHER INFORMATION: sequence leader
<220> FEATURE:
<221> NAME/KEY: CDS
<222> LOCATION: (1)..(66)

<400> SEQUENCE: 19 atg gac atg agg gtc ccc gct cag ctc ctg ggg ctt ctg ctg ctc tgg    48
Met Asp Met Arg Val Pro Ala Gln Leu Leu Gly Leu Leu Leu Leu Trp
1               5                   10                  15 ctc cca ggt gcc aga tgt                                            66
```

Leu Pro Gly Ala Arg Cys
            20

<210> SEQ ID NO 20
<211> LENGTH: 22
<212> TYPE: PRT
<213> ORGANISM: Artificial Sequence
<220> FEATURE:
<223> OTHER INFORMATION: Synthetic Construct

<400> SEQUENCE: 20

Met Asp Met Arg Val Pro Ala Gln Leu Leu Gly Leu Leu Leu Leu Trp
1               5                   10                  15

Leu Pro Gly Ala Arg Cys
            20

<210> SEQ ID NO 21
<211> LENGTH: 10763
<212> TYPE: DNA
<213> ORGANISM: Artificial sequence
<220> FEATURE:
<223> OTHER INFORMATION: Vecteur d'expression

<400> SEQUENCE: 21

```
gatctcccga tccctatgg tgcactctca gtacaatctg ctctgatgcc gcatagttaa      60
gccagtatct gctccctgct tgtgtgttgg aggtcgctga gtagtgcgcg agcaaaattt    120
aagctacaac aaggcaaggc ttgaccgaca attgcatgaa gaatctgctt agggttaggc    180
gttttgcgct gcttcgcgat gtacgggcca gatatacgcg tatctgaggg gactagggtg    240
tgtttaggcg aaaagcgggg cttcggttgt acgcggttag gagtcccctc aggatatagt    300
agtttcgctt ttgcataggg aggggggaaat gtagtcttat gcaatactct tgtagtcttg    360
caacatggta acgatgagtt agcaacatgc cttacaagga gagaaaaagc accgtgcatg    420
ccgattggtg gaagtaaggt ggtacgatcg tgccttatta ggaaggcaac agacgggtct    480
gacatggatt ggacgaacca ctgaattccg cattgcagag atattgtatt taagtgccta    540
gctcgataca ataaacgcca tttgaccatt caccacattg gtgtgcacct ccaagcttgg    600
taccgagctc ggatccacta gagcagaagt tggtcgtgag gcactgggca ggtaagtatc    660
aaggttacaa gacaggtta aggagaccaa tagaaactgg gcttgtcgag acagagaaga    720
ctcttgcgtt tctgatggc acctattggt cttactgaca tccactttgc ctttctctcc    780
acaggtgtcc actcccagtt caattacagc tcttgctagc gccgccacca tgaaacatct    840
gtggttcttc cttctcctgg tggcagctcc cagatgggtc ctgtcccagg tgcagctggt    900
ggagtcgggg gcggcttgg taaagcctgg gggtccctg agactctcct gcgcagcctc    960
cggattcacc ttcactgact actacatgga ctgggtccgc caggctccag ggaaggggct   1020
ggagtgggtc tcacgtatta gcctggtgg tgatgtcaca tggtacgcag actccgtgaa   1080
gggcagattt accatctcca gagacaacgc ccagaacaca ctgtatcttc aaatgaacag   1140
cctgagagct gaggacacgg ctgtctattt ctgtgcgaga gatgatatag tggtgtccag   1200
aattttttgat gactggggcc agggagtcct ggtcaccgtc tcctcagcct ccaccaaggg   1260
cccatcggtc ttccccctgg caccctcctc aagagcacc tctggggca gcggccct     1320
gggctgcctg gtcaaggact acttccccga accggtgacg gtgtcgtgga actcaggcgc   1380
cctgaccagc ggcgtgcaca ccttcccggc tgtcctacag tcctcaggac tctactccct   1440
cagcagcgtg gtgaccgtgc cctccagcag cttgggcacc cagacctaca tctgcaacgt   1500
gaatcacaag cccagcaaca ccaaggtgga caagaaagtt gagcccaaat cttgtgacaa   1560
```

```
aactcacaca tgcccaccgt gcccagcacc tgaactcctg gggggaccgt cagtcttcct    1620 cttccccca aaacccaagg acaccctcat gatctcccgg accoctgagg tcacatgcgt    1680 ggtggtggac gtgagccacg aagaccctga ggtcaagttc aactggtacg tggacggcgt    1740
ggaggtgcat aatgccaaga caaagccgcg ggaggagcag tacaacagca cgtaccgtgt    1800
ggtcagcgtc ctcaccgtcc tgcaccagga ctggctgaat ggcaaggagt acaagtgcaa    1860
ggtctccaac aaagccctcc cagccoccat cgagaaaacc atctccaaag ccaaagggca    1920
gccccgagaa ccacaggtgt acaccctgcc cccatcccgg gatgagctga ccaagaacca    1980
ggtcagcctg acctgcctgg tcaaaggctt ctatcccagc gacatcgccg tggagtggga    2040
gagcaatggg cagccggaga caactacaa gaccacgcct cccgtgctgg actccgacgg    2100
ctccttcttc ctctacagca agctcaccgt ggacaagagc aggtggcagc aggggaacgt    2160
cttctcatgc tccgtgatgc atgaggctct gcacaaccac tacacgcaga gagcctctc    2220 cctgtctccg ggtaaatgat agggcgcgcc gctagagagg atcccgggtg gcatccctgt    2280 gaccoctccc cagtgcctct cctggccctg gaagttgcca ctccagtgcc caccagcctt    2340
gtcctaataa aattaagttg catcattttg tctgactagg tgtccttcta taatattatg    2400
gggtggaggg gggtggtatg gagcaagggg caagttggga agacaacctg tagggcctgc    2460
ggggtctatt gggaaccaag ctggagtgca gtggcacaat cttggctcac tgcaatctcc    2520
gcctcctggg ttcaagcgat tctcctgcct cagcctcccg agttgttggg attccaggca    2580
tgcatgacca ggctcagcta attttgtttt ttttggtaga cggggttt caccatattg     2640 gccaggctgg tctccaactc ctaatctcag gtgatctacc caccttggcc tcccaaattg    2700
ctgggattac aggcgtgaac cactgctccc ttccctgtcc ttctgattt aaaataacta    2760 taccagcagg aggacgtcca gacacagcat aggctacctg gccatgccca accggtggga    2820
catttgagtt gcttgcttgg cactgtcctc tcatgcgttg ggtccactca gtagatgcct    2880
gttcatatgc tcgagatctc ccgatcccct atggtgcact ctcagtacaa tctgctctga    2940
tgccgcatag ttaagccagt atctgctccc tgcttgtgtg ttggaggtcg ctgagtagtg    3000
cgcgagcaaa atttaagcta caacaaggca aggcttgacc gacaattgca tgaagaatct    3060
gcttagggtt aggcgttttg cgctgcttcg cgatgtacgg gccagatata cgcgtatctg    3120
aggggactag ggtgtgttta ggcgaaaagc ggggcttcgg ttgtacgcgg ttaggagtcc    3180
cctcaggata tagtagtttc gcttttgcat agggaggggg aaatgtagtc ttatgcaata    3240
ctcttgtagt cttgcaacat ggtaacgatg agttagcaac atgccttaca aggagagaaa    3300
aagcaccgtg catgccgatt ggtggaagta aggtggtacg atcgtgcctt attaggaagg    3360
caacagacgg gtctgacatg gattggacga accactgaat tccgcattgc agagatattg    3420
tatttaagtg cctagctcga tacaataaac gccatttgac cattcaccac attggtgtgc    3480
acctccaagc ttggtaccga gctcggatcc actagagcag aagttggtcg tgaggcactg    3540
ggcaggtaag tatcaaggtt acaagacagg tttaaggaga ccaatagaaa ctgggcttgt    3600
cgagacagag aagactcttg cgtttctgat aggcacctat ggtcttact gacatccact    3660 ttgcctttct ctccacaggt gtccactccc agttcaatta cagctcttac tagtgccgcc    3720
accatggaca tgagggtccc cgctcagctc ctggggcttc tgctgctctg ctcccaggt    3780 gccagatgtg agctccagat gacacagtct ccatcctccc tgtctgcatc tgtaggagac    3840
agagtcacca tcacttgtcg ggcaagtcag agcattagaa gttatttagc ctggtatcag    3900
cagaaaccag ggaaagcccc taagctcctg atctatgatg cagcccattt gcaaagtggg    3960
```

```
gtcccatcaa ggttcagcgg cagtggatct gggacagaat tcagtctcac catcagcagc   4020
ctgcaacctg aagattttgc agtttattac tgtcaacagc gtaatagtta tcctctgact   4080
ttcggcggag ggaccaaggt ggagatcaaa cgaactgtgg ctgcaccaag tgtcttcatc   4140
ttcccgccat ctgatgagca gttgaaatct ggaactgcct ctgttgtgtg cctgctgaat   4200
aacttctatc ccagagaggc caaagtacag tggaaggtgg ataacgccct ccaatcgggt   4260
aactcccagg agagtgtcac agagcaggac agcaaggaca gcacctacag cctcagcagc   4320
accctgacgc tgagcaaagc agactacgag aaacacaaag tctacgcctg cgaagtcacc   4380
catcagggcc tgagctcgcc cgtcacaaag agcttcaaca ggggagagtg ttagtgaact   4440
ctagagctcg ctgatcagcc tcgactgtgc cttctagttg ccagccatct gttgtttgcc   4500
cctcccccgt gccttccttg acccggaag gtgccactcc cactgtcctt tcctaataaa   4560
atgaggaaat tgcatcgcat tgtctgagta ggtgtcattc tattctgggg ggtggggtgg   4620
ggcaggacag caaggggag gattgggaag acaaatagcag gcatgctggg gacatatgat   4680
ttaaatactg gggctcgact gtggaatgtg tgtcagttag ggtgtggaaa gtccccaggc   4740
tccccagcag gcagaagtat gcaaagcatg catctcaatt agtcagcaac caggtgtgga   4800
aagtccccag gctccccagc aggcagaagt atgcaaagca tgcatctcaa ttagtcagca   4860
accatagtcc cgcccctaac tccgcccatc ccgcccctaa ctccgcccag ttccgcccat   4920
tctccgcccc atggctgact aattttttt atttatgcag aggccgaggc cgcctcggcc   4980
tctgagctat tccagaagta gtgaggaggc ttttttggag gcctaggctt ttgcaaaaag   5040
cttggggggg gggacagctc agggctgcga tttcgcgcca aacttgacgg caatcctagc   5100
gtgaaggctg gtaggatttt atccccgctg ccatcatggt tcgaccattg aactgcatcg   5160
tcgccgtgtc ccaaaatatg gggattggca agaacggaga cctaccctgg cctccgctca   5220
ggaacgagtt caagtacttc caaagaatga ccacaacctc ttcagtggaa ggtaaacaga   5280
atctggtgat tatgggtagg aaaacctggt tctccattcc tgagaagaat cgacctttaa   5340
aggacagaat taatatagtt ctcagtagag aactcaaaga accaccacga ggagctcatt   5400
ttcttgccaa aagtttggat gatgccttaa gacttattga acaaccggaa ttggcaagta   5460
aagtagacat ggtttggata gtcggaggca gttctgttta ccaggaagcc atgaatcaac   5520
caggccacct cagactcttt gtgacaagga tcatgcagga atttgaaagt gacacgtttt   5580
tcccagaaat tgatttgggg aaatataaac ttctcccaga atacccaggc gtcctctctg   5640
aggtccagga ggaaaaaggc atcaagtata agtttgaagt ctacgagaag aaagactaac   5700
aggaagatgc tttcaagttc tctgctcccc tcctaaagct atgcattttt ataagaccat   5760
gggacttttg ctggctttag atcgatcttt gtgaaggaac cttacttctg tggtgtgaca   5820
taattggaca aactacctac agagatttaa agctctaagg taaatataaa attttaagt   5880 gtataatgtg ttaaactact gattctaatt gtttgtgtat tttagattcc aacctatgga   5940
actgatgaat gggagcagtg gtggaatgcc tttaatgagg aaaacctgtt ttgctcagaa   6000
gaaatgccat ctagtgatga tgaggctact gctgactctc aacattctac tcctccaaaa   6060
aagaagagaa aggtagaaga ccccaaggac tttccttcag aattgctaag ttttttgagt   6120
catgctgtgt ttagtaatag aactcttgct tgctttgcta tttacaccac aaaggaaaaa   6180
gctgcactgc tatacaagaa aattatggaa aaatattctg taacctttat aagtaggcat   6240
aacagttata atcataacat actgtttttt cttactccac acaggcatag agtgtctgct   6300
attaataact atgctcaaaa attgtgtacc tttagctttt taatttgtaa aggggttaat   6360
```

```
aaggaatatt tgatgtatag tgccttgact agagatcata atcagccata ccacatttgt    6420
agaggtttta cttgctttaa aaaacctccc acacctcccc ctgaacctga aacataaaat    6480
gaatgcaatt gttgttgtta acttgtttat tgcagcttat aatggttaca aataaagcaa    6540
tagcatcaca aatttcacaa ataaagcatt tttttcactg cattctagtt gtggtttgtc    6600
caaactcatc aatgtatctt atcatgtctg gatccgcgta tggtgcactc tcagtacaat    6660
ctgctctgat gccgcatagt taagccagcc ccgacacccg ccaacacccg ctgacgcgcc    6720
ctgacgggct tgtctgctcc cggcatccgc ttacagacaa gctgtgaccg tctccgggag    6780
ctgcatgtgt cagaggtttt caccgtcatc accgaaacgc gcgagacgaa agggcctcgt    6840
gatacgccta ttttataggt taatgtcat gataataatg gtttcttaga gatctcgagg     6900
gtgggccatc gccctgatag acggttttc gcccttgac gttggagtcc acgttcttta     6960
atagtggact cttgttccaa actgaacaa cactcaaccc tatctcggtc tattcttttg     7020 attttataagg gattttgccg atttcggcct attggttaaa aaatgagctg atttaacaaa   7080
aatttaacgc gaattttaac aaaatattaa cgcttacaat ttcctgatgc ggtattttct    7140
ccttacgcat ctgtgcggta tttcacaccg catacgcgga tctgcgcagc accatggcct    7200
gaaataacct ctgaaagagg aacttggtta ggtaccttct gaggcggaaa gaaccagctg    7260
tggaatgtgt gtcagttagg gtgtggaaag tccccaggct ccccagcagg cagaagtatg    7320
caaagcatgc atctcaatta gtcagcaacc aggtgtggaa agtccccagg ctccccagca    7380
ggcagaagta tgcaaagcat gcatctcaat tagtcagcaa ccatagtccc gcccctaact    7440
ccgcccatcc cgcccctaac tccgcccagt tccgcccatt ctccgcccca tggctgacta    7500 attttttttta tttatgcaga ggccgaggcc gcctcggcct ctgagctatt ccagaagtag    7560
tgaggaggct ttttggagg cctaggcttt tgcaaaaagc ttgattcttc tgacacaaca    7620
gtctcgaact taaggctaga gccaccatga ttgaacaaga tggattgcac gcaggttctc    7680
cggccgcttg ggtggagagg ctattcggct atgactgggc acaacagaca atcggctgct    7740
ctgatgccgc cgtgttccgg ctgtcagcgc aggggcgccc ggttcttttt gtcaagaccg    7800
acctgtccgg tgccctgaat gaactgcagg acgaggcagc gcggctatcg tggctggcca    7860
cgacgggcgt tccttgcgca gctgtgctcg acgttgtcac tgaagcggga agggactggc    7920
tgctattggg cgaagtgccg gggcaggatc tcctgtcatc tcaccttgct cctgccgaga    7980
aagtatccat catggctgat gcaatgcggc ggctgcatac gcttgatccg gctacctgcc    8040
cattcgacca ccaagcgaaa catcgcatcg agcgagcacg tactcggatg gaagccggtc    8100
ttgtcgatca ggatgatctg gacgaagagc atcaggggct cgcgccagcc gaactgttcg    8160
ccaggctcaa ggcgcgcatg cccgacggcg aggatctcgt cgtgacccat ggcgatgcct    8220
gcttgccgaa tatcatggtg gaaaatggcc gcttttctgg attcatcgac tgtggccggc    8280
tgggtgtggc ggaccgctat caggacatag cgttggctac ccgtgatatt gctgaagagc    8340
ttggcggcga atgggctgac cgcttcctcg tgctttacgg tatcgccgct cccgattcgc    8400
agcgcatcgc cttctatcgc cttcttgacg agttcttctg agcgggactc tggggttcga    8460
aatgaccgac caagcgacgc ccaacctgcc atcacgatgg ccgcaataaa atatctttat    8520
tttcattaca tctgtgtgtt ggttttttgt gtgaatcgat agcgataagg atcgatcctc    8580
tagctagagt cgatcgacct gcagggatcc gcgtatggtg cactctcagt acaatctgct    8640
ctgatgccga atagttaagc cagccccgac acccgccaac acccgctgac gcgccctgac    8700
gggcttgtct gctcccggca tccgcttaca gacaagctgt gaccgtctcc gggagctgca    8760
```

```
tgtgtcagag gttttcaccg tcatcaccga aacgcgcgag acgaaagggc ctcgtgatac    8820
gcctattttt ataggttaat gtcatgataa taatggtttc ttagagatct tagatccagt    8880
tgaactgcag ggaaatccgg acgtgtatac cagtttaaac atgttaatta agtcgacgcg    8940
gccgcaggtg gcacttttcg gggaaatgtg cgcggaaccc ctatttgttt attttttctaa   9000 atacattcaa atatgtatcc gctcatgaga caataaccct gataaatgct tcaataatat    9060
tgaaaaagga agagtatgag tattcaacat ttccgtgtcg cccttattcc cttttttgcg    9120 gcatttttgcc ttcctgtttt tgctcaccca gaaacgctgg tgaaagtaaa agatgctgaa    9180
gatcagttgg gtgcacgagt gggttacatc gaactggatc tcaacagcgg taagatcctt    9240
gagagtttcc gccccgaaga acgttttcca atgatgagca cttttaaagt tctgctatgt    9300
ggcgcggtga tatcccgtat tgacgccggg caagagcaac tcggtcgccg catacactat    9360
tctcagaatg acttggttga gtactcacca gtcacagaaa agcatcttac ggatggcatg    9420
acagtaagag aattatgcag tgctgccata accatgagtg ataacactgc ggccaactta    9480
cttctgacaa cgatcggagg accgaaggag ctaaccgctt ttttgcacaa catgggggat    9540
catgtaactc gccttgatcg ttgggaaccg gagctgaatg aagccatacc aaacgacgag    9600
cgtgacacca cgatgcctgt agcaatggca acaacgttgc gcaaactatt aactggcgaa    9660
ctacttactc tagcttcccg gcaacaatta atagactgga tggaggcgga taaagttgca    9720
ggaccacttc tgcgctcggc ccttccggct ggctggttta ttgctgataa atctggagcc    9780
ggtgagcgtg ggtctcgcgg tatcattgca gcactggggc cagatggtaa gccctcccgt    9840
atcgtagtta tctacacgac ggggagtcag gcaactatgg atgaacgaaa tagacagatc    9900
gctgagatag gtgcctcact gattaagcat tggtaactgt cagaccaagt ttactcatat    9960
atactttaga ttgatttaaa acttcatttt taatttaaaa ggatctaggt gaagatcctt   10020
tttgataatc tcatgaccaa aatcccttaa cgtgagtttt cgttccactg agcgtcagac   10080
cccgtagaaa agatcaaagg atcttcttga gatcctttttt ttctgcgcgt aatctgctgc   10140
ttgcaaacaa aaaaaccacc gctaccagcg gtggtttgtt tgccggatca agagctacca   10200
actctttttc cgaaggtaac tggcttcagc agagcgcaga taccaaatac tgtccttcta   10260
gtgtagccgt agttaggcca ccacttcaag aactctgtag caccgcctac atacctcgct   10320
ctgctaatcc tgttaccagt ggctgctgcc agtggcgata agtcgtgtct taccgggttg   10380
gactcaagac gatagttacc ggataaggcg cagcggtcgg gctgaacggg gggttcgtgc   10440
acacagccca gcttggagcg aacgacctac accgaactga gatacctaca gcgtgagcta   10500
tgagaaagcg ccacgcttcc cgaagggaga aaggcggaca ggtatccggt aagcggcagg   10560
gtcggaacag gagagcgcac gagggagctt ccagggggaa acgcctggta tctttatagt   10620
cctgtcgggt ttcgccacct ctgacttgag cgtcgatttt tgtgatgctc gtcaggggggg   10680 cggagcctat ggaaaaacgc cagcaacgcg gcctttttac ggttcctggc cttttgctgg   10740
ccttttgctc acatggctcg aca                                           10763
```

<210> SEQ ID NO 22
<211> LENGTH: 37
<212> TYPE: DNA
<213> ORGANISM: Artificial Sequence
<220> FEATURE:
<223> OTHER INFORMATION: amorce sens leader VH chaine lourde humaine

<400> SEQUENCE: 22
ctcagtgcta gcgccgccac catgaaacat ctgtggt                              37

<210> SEQ ID NO 23
<211> LENGTH: 26
<212> TYPE: DNA
<213> ORGANISM: Artificial Sequence
<220> FEATURE:
<223> OTHER INFORMATION: amorce antisens leader VH chaine lourde humaine

<400> SEQUENCE: 23
ccagctgcac ctgggacagg acccat                                         26

<210> SEQ ID NO 24
<211> LENGTH: 26
<212> TYPE: DNA
<213> ORGANISM: Artificial Sequence
<220> FEATURE:
<223> OTHER INFORMATION: amorce sens VH chaine lourde de macaque

<400> SEQUENCE: 24
atgggtcctg tcccaggtgc agctgg                                         26

<210> SEQ ID NO 25
<211> LENGTH: 40
<212> TYPE: DNA
<213> ORGANISM: Artificial Sequence
<220> FEATURE:
<223> OTHER INFORMATION: amorce antisens VH chaine lourde de macaque

<400> SEQUENCE: 25
accgatgggc ccttggtgga ggctgaggag acggtgacca                          40

<210> SEQ ID NO 26
<211> LENGTH: 40
<212> TYPE: DNA
<213> ORGANISM: Artificial Sequence
<220> FEATURE:
<223> OTHER INFORMATION: amorce sens leader VK chaine legere humaine

<400> SEQUENCE: 26
ctcagtacta gtgccgccac catggacatg agggtccccg                          40

<210> SEQ ID NO 27
<211> LENGTH: 30
<212> TYPE: DNA
<213> ORGANISM: Artificial Sequence
<220> FEATURE:
<223> OTHER INFORMATION: amorce antisens leader VK chaine legere humaine

<400> SEQUENCE: 27
tgtcatctgg agctcacatc tggcacctgg                                     30

<210> SEQ ID NO 28
<211> LENGTH: 30
<212> TYPE: DNA
<213> ORGANISM: Artificial Sequence
<220> FEATURE:
<223> OTHER INFORMATION: amorce sens VK chaine legere de macaque

<400> SEQUENCE: 28
ccaggtgcca gatgtgagct ccagatgaca                                     30

<210> SEQ ID NO 29
<211> LENGTH: 48
<212> TYPE: DNA
<213> ORGANISM: Artificial Sequence

```
<220> FEATURE:
<223> OTHER INFORMATION: amorce antisens VK chaine legere de macaque

<400> SEQUENCE: 29
tgaagacact tggtgcagcc acagttcgtt tgatctccac cttggtcc            48
```